United States Patent
Fruttarolo et al.

(10) Patent No.: US 9,409,864 B2
(45) Date of Patent: Aug. 9, 2016

(54) SULFONAMIDE TRPA1 RECEPTOR ANTAGONISTS

(71) Applicant: ARIO PHARMA LIMITED, Cambridge (GB)

(72) Inventors: Francesca Fruttarolo, Ferrara (IT); Maria Giovanna Pavani, Vigarano Mainarda (IT); Serena Bencivenni, Cento (IT); Raffaele Gatti, Ferrara (IT); Mauro Napoletano, Milan (IT)

(73) Assignee: ARIO PHARMA LIMITED, Cambridge (GB)

( * ) Notice: Subject to any disclaimer, the term of this patent is extended or adjusted under 35 U.S.C. 154(b) by 0 days.

(21) Appl. No.: 14/772,622

(22) PCT Filed: Mar. 6, 2014

(86) PCT No.: PCT/EP2014/054310
§ 371 (c)(1),
(2) Date: Sep. 3, 2015

(87) PCT Pub. No.: WO2014/135617
PCT Pub. Date: Sep. 12, 2014

(65) Prior Publication Data
US 2016/0024009 A1    Jan. 28, 2016

(30) Foreign Application Priority Data

Mar. 6, 2013 (EP) ..................................... 13158046

(51) Int. Cl.
| | | |
|---|---|---|
| *A61K 31/505* | (2006.01) | |
| *C07D 213/56* | (2006.01) | |
| *C07D 213/74* | (2006.01) | |
| *C07D 333/34* | (2006.01) | |
| *C07C 311/19* | (2006.01) | |
| *C07D 409/12* | (2006.01) | |
| *C07D 213/40* | (2006.01) | |
| *C07D 213/64* | (2006.01) | |
| *C07C 311/20* | (2006.01) | |
| *C07D 213/73* | (2006.01) | |
| *C07D 213/89* | (2006.01) | |
| *C07D 401/04* | (2006.01) | |
| *C07D 409/14* | (2006.01) | |

(52) U.S. Cl.
CPC ............ *C07D 213/56* (2013.01); *C07C 311/19* (2013.01); *C07C 311/20* (2013.01); *C07D 213/40* (2013.01); *C07D 213/64* (2013.01); *C07D 213/73* (2013.01); *C07D 213/74* (2013.01); *C07D 213/89* (2013.01); *C07D 333/34* (2013.01); *C07D 401/04* (2013.01); *C07D 409/12* (2013.01); *C07D 409/14* (2013.01)

(58) Field of Classification Search
CPC .. C07D 213/56; C07D 213/40; C07D 213/64; C07D 213/73; C07D 213/74; C07D 213/89; C07D 333/34; C07D 401/04; C07D 409/12; C07D 409/14; C07C 311/19; C07C 311/20
See application file for complete search history.

(56) References Cited

U.S. PATENT DOCUMENTS

| | | | |
|---|---|---|---|
| 2009/0170867 A1* | 7/2009 | Kurose ................. | C07D 401/04 514/253.01 |
| 2009/0264474 A1* | 10/2009 | Branum ............... | C07D 333/36 514/342 |
| 2010/0160289 A1* | 6/2010 | Macielag .............. | C07C 311/32 514/210.19 |
| 2014/0005393 A1* | 1/2014 | Tsuzuki ............... | C07D 217/22 544/333 |
| 2015/0197509 A1* | 7/2015 | Brotherton-Pleiss | C07D 231/18 514/255.05 |

FOREIGN PATENT DOCUMENTS

| | | |
|---|---|---|
| WO | WO 2010/141805 A1 | 12/2010 |
| WO | WO 2014/049047 | 4/2014 |

OTHER PUBLICATIONS

International Preliminary Report on Patentability and Written Opinion issued Sep. 8, 2015 in PCT/EP2014/054310.
International Search Report dated Jul. 1, 2014 in International Application No. PCT/EP2014/054310.
European Search Report dated Jul. 18, 2013 in Application No. EP 13158046.

* cited by examiner

*Primary Examiner* — Alexander R Pagano
(74) *Attorney, Agent, or Firm* — Baker Botts L.L.P.

(57) ABSTRACT

The invention discloses compounds of Formula (I). The compounds of formula (I) are TRPA1 antagonists and are useful as active ingredients of pharmaceutical compositions for the treatment of pain and other conditions ameliorated by the inhibition of TRPA1 receptors.

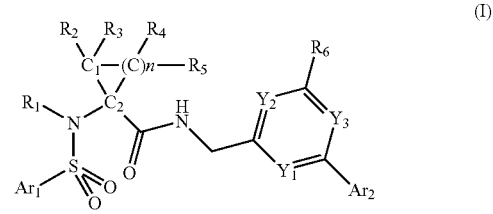

(I)

15 Claims, No Drawings

SULFONAMIDE TRPA1 RECEPTOR ANTAGONISTS

CROSS-REFERENCE TO RELATED APPLICATIONS

This application is a U.S. National Stage Patent Application under 35 U.S.C. §371 of International Application No. PCT/EP2014/054310, filed on Mar. 6, 2014, which claims priority to European Patent Application Serial No. 13158046.6 filed Mar. 6, 2013, each of which is incorporated by reference in its entirety herein, and priority to each of which is claimed.

FIELD OF THE INVENTION

The present invention concerns TRPA1 antagonists characterized by novel sulfonamide or cyclopropyl sulfonamide moieties and, when possible, pharmaceutically acceptable salts thereof along with the formulations containing them. The pharmaceutical compositions of the invention are useful in the treatment of pain, pulmonary diseases and other conditions ameliorated by the inhibition of the TRPA1 receptors.

BACKGROUND OF THE INVENTION

TRPA1 (ANKTM1, p120) is a non-selective cation channel that belongs to the Transient Receptor Potential (TRP) superfamily. TRPA1 was first identified as a transformation sensitive mRNA in cultured human lung fibroblasts (Jaquemar et al., *J. Bio. Chem.*, 1999, 274, 7325-7333). Subsequent studies indicated that TRPA1 is also highly expressed in sensory neurons of the dorsal root, trigeminal and nodose ganglia as well as in hair cells of the inner ear (Story et al., *Cell*, 2003, 112, 819-829; Corey et al., *Nature*, 2004, 432, 23730; Nagata et al., *J Neurosci.*, 2005, 25, 4052-4061; Diogenes et al., *J. Dent. Res.*, 2007, 86, 550-555). In sensory neurons, TRPA1 expression is most abundant in small diameter neurons where it co-localizes with markers of peptidergic nociceptors such as TRPV1, CGRP and substance P (Story et al., supra; Bautista et al., *PNAS*, 2005, 102, 12248-12252; Nagata et al., *J. Neurosci.*, 2005, 25, 4052-4061; Diogenes et al., *J. Dent. Res.*, 2007, 86, 550-555).

The finding that TRPA1 is expressed in small diameter nociceptors has led to the suggestion that this channel may be involved in pain sensation. Indeed a number of additional observations support this suggestion. For example, TRPA1 expression is increased by inflammatory mediators such as NGF (Diogenes et al., *J. Dent. Res.*, 2007, 86, 550-555) and following nerve injury or inflammation (Obata et al., *J. Clin. Invest.* 2005, 115, 2393-2401; Frederick et al., *Biochem. Biophys. Res. Commun.*, 2007, 358, 1058-1064). Bradykinin, a potent algogenic peptide released at sites of injury and inflammation, activates TRPA1 via G-protein coupled BK2 receptors (Bandell et al., *Neuron*, 2004, 41, 849-857). In addition, TRPA1 is activated by a range of pungent or irritant compounds per se eliciting pain in animals and humans, such as mustard oil (AITC), cinnamaldehyde, acreolin, allicin, and formalin (Bandell et al., supra; Namer et al., *Neuroreport*, 2005, 16, 955-959; Bautista et al., *Cell*, 2006, 124, 1269-1282; Fujita et al., *Br. J. Pharmacol.*, 2007, 151, 153-160; McNamara et al., *PNAS*, 2007, 104, 13525-13530).

Finally, TRPA1 may also be activated by noxious cold (Bandell et al., *Neuron*, 2004, 41, 849-857; Jordt et al., *Nature*, 2004, 427, 260-265; Nagata et al., *J. Neurosci.*, 2005, 25, 4052-4061) and the intra-thecal administration of TRPA1 anti-sense oligodeoxynucleotide suppresses inflammation as well as nerve injury, induced cold allodynia (Obata et al., *J. Clin. Invest.*, 2005, 115, 2393-2401). Likewise, mustard oil and bradykinin-induced acute pain and hyperalgesia is abolished in TRPA1−/− mice (Bautista et al., supra; Kwan et al., *Neuron*, 2006, 50, 277-289).

TRPA1 receptors also play a role in airway disorders. Treatment with cigarette smoke extracts (CSE) increases $Ca^{2+}$ influx in TRPA1-transfected cells, and promotes neuropeptide release from isolated guinea pig airway tissue. Furthermore, the effect of CSE on $Ca^{2+}$ influx in dorsal root ganglion neurons is abolished in TRPA1-deficient mice. These data suggest a role for TRPA1 in the pathogenesis of CSE-induced diseases such as chronic obstructive pulmonary disease (COPD) (Andre et al., *J. Clin. Invest.*, 2008, 118, 2574-2582).

Recent data highlighted the TRPA1 channel role in inflammation and bronchial hyperactivity in a murine asthma model. Other studies provided evidence that inhalation of TRPA1 stimulants elicited cough reflex in guinea pigs and human volunteers. (Facchinetti et Patacchini, *The Open Drug Discovery J.* 2010, 2, 71-80). TRPA1 antagonists could emerge as novel drugs for treatment of COPD, asthma and chronic cough.

TRPA1 is found also in bladder and urethra urothelium, epithelium and nerve fibers of the urothelium, sub-urothelial space, muscle layers and around blood vessels (Du et al., *Urology*, 2008, 72, 450-455; Andrade et al., *Biochem. Pharmacol.*, 2006, 72, 104-114; Gratzke et al., *Eur. Urology*, 2008, Apr. 30 e-pub; Streng et al., *Eur. Urology*, 2008, 53, 391-400). TRPA1 expression is increased in bladder mucosa from patients with bladder outlet obstruction (Du et al., *Urology*, 2008, 72, 450-455). Activation of TRPA1 increases micturition frequency and reduces voiding volume (Streng et al., supra).

Activation of TRPA1 in the bladder by reactive metabolites of cyclophosphamide (e.g., acrolein) may be responsible for cystitis that sometimes accompanies the use of chemotherapeutic agents (Bautista et al., supra). TRPA1 is also expressed in colonic afferents, is upregulated following induction of experimental colitis, and TRPA1 antisense oligonucleotides suppresses colitis-induced hyperalgesia to colonic distension (Yang et al., *Neurosci Lett.*, 2008, 440, 237-241). These data suggest a role for TRPA1 in the pathogenesis of visceral pain and dysfunction, such as bladder instability, urinary incontinence, cystitis and colitis.

DESCRIPTION OF THE INVENTION

The present invention relates to TRPA1 inhibitors of formula (I)

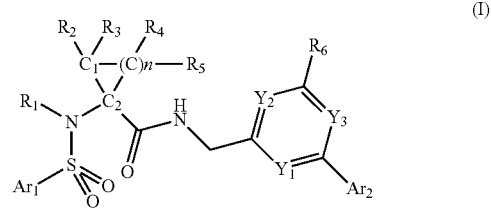

wherein:

$Ar_1$ is:

i) phenyl substituted with 0, 1, 2 or 3 substituents $R_a$; or ii) a 5- or 6-membered monocyclic aromatic heterocycle ring optionally substituted with one or two substituents $R_a$;

where each $R_a$ is independently halo, —$C_{1-4}$alkyl, —$OC_{1-4}$alkyl, —CN, —$CF_3$, —$OCF_3$, —$NO_2$, —$C(O)C_{1-4}$alkyl or —$CO_2H$;

$Ar_2$ is:

i) phenyl substituted with 0, 1, 2 or 3 substituents $R_b$; where each $R_b$ is independently halo, —$C_{1-4}$alkyl, —$C(O)NR_cR_d$, —$OC_{1-4}$alkyl, —$OC_{0-4}$alkylCF$_3$, —CN, —$CF_3$, —$OCF_2H$, —$NO_2$, —$NR_cR_d$, —$S(O)_{0-2}C_{1-4}$alkyl, —$C(O)C_{1-4}$alkyl, $S(O)(O)NH_2$, —$(CH_2)_{0-2}$-morpholinyl, piperidin-1-yl, piperazinyl, said piperazinyl being optionally substituted with a methyl, or two $R_b$ substituents on adjacent carbon atoms taken together form —$O(CH_2)_{1-2}O$—;

ii) pyridyl substituted with 0, 1 or 2 substituents $R_e$; where each $R_e$ is independently selected from halo, —$C_{1-4}$alkyl, —$OC_{1-4}$alkyl, —$CF_3$, —$NR_cR_d$ or 4-morpholinyl; or iii) a bicyclic 9-11-membered aromatic heterocycle optionally substituted with 1 substituent $R_f$; where $R_f$ is —$C_{1-4}$alkyl;

$R_c$ and $R_d$ are each independently selected from H or —$C_{1-4}$ alkyl;

$R_1$ is H, $C_{1-4}$alkyl-O—$C_{1-4}$alkyl, or $C_{1-4}$alkyl optionally substituted with halo;

$R_2$, $R_3$, $R_4$, and $R_5$ are each independently H, halo or —$C_{1-4}$alkyl;

n is 0 or 1 providing that when n is 1 the bond between C1 and C2 is single and when n is 0 the bond between C1 and C2 is double;

each $Y_1$, $Y_2$ and $Y_3$ is independently CH or N;

$R_6$ is i) H, —$C_{1-4}$alkyl, —$CF_3$, —$OR_z$ or —$NR_hR_i$;

where $R_h$ is selected from a) H, —$C_{0-4}$alkylCF$_3$, —$C_{1-4}$alkyl-N(CH$_3$)$_2$, saturated $C_{3-7}$cycloalkyl or —$C_{1-4}$alkyl-monocyclic heteroaryl ring;

b) —$C_{1-5}$alkyl optionally substituted with OH;

c) —$C_{1-4}$alkyl-heterocycloalkyl, said heterocycloalkyl being optionally substituted with —$C_{1-4}$alkyl; or d) —$C_{0-4}$alkyl-phenyl, said phenyl being optionally substituted with one or two $R_j$ moieties; where each $R_j$ is independently halo, —$OC_{1-4}$alkyl, $R_z$ is —$C_{1-4}$alkyl, —$C_{1-4}$alkylCF$_3$ or —$C_{1-4}$alkyl-heterocycloalkyl;

ii) 1-pyrrolidinyl optionally substituted with a moiety selected from the group consisting of —$NR_kR_i$ and —$C_{1-4}$alkyl, said —$C_{1-4}$alkyl being optionally substituted with —OH;

iii) 1-piperidinyl optionally substituted with —$C_{1-4}$alkyl, —$C(O)NH_2$, —$CO_2C_{1-4}$alkyl or —$C_{0-4}$alkyl-phenyl;

iv) piperazinyl optionally substituted with —$C_{1-5}$alkyl, —$OC_{1-4}$alkyl, —$C_{0-4}$alkylpyridyl, —$C_{0-4}$alkyl-1-methyl-piperidin-4-yl, —$C_{0-4}$alkylNR$_k$R$_i$ or —$C_{0-4}$alkyl-phenyl, said phenyl optionally substituted with one or two $R_T$ substituents; where each $R_T$ substituent is selected from the group consisting of halo, —$OCF_3$, —$C_{1-4}$alkyl, —$OC_{1-4}$alkyl, —$CO_2C_{1-4}$alkyl, —$C(O)C_{1-4}$alkyl and —$C_{0-4}$alkylNR$_k$R$_i$, or two $R_T$ substituents on adjacent carbon atoms taken together form —$O(CH_2)_{1-2}O$—;

v) phenyl optionally substituted with halo, —$CF_3$, —$OCF_3$;

vi) pyridyl;

vii) morpholin-yl;

$R_k$ is H, —$C_{1-4}$alkyl or —$C(O)_{1-2}C_{1-4}$alkyl;

$R_i$ is H or $C_{1-4}$alkyl.

When an asymmetrical carbon is present in a compound of the formula (I), such a compound may exist in optically active form or in the form of mixtures of optical isomers, e. g. in the form of racemic mixtures. The present invention refers to all optical isomers and their mixtures, including the racemic mixtures.

In a further aspect of the present invention, compounds of formula I bearing a basic nitrogen may be prepared in the form of a pharmaceutically acceptable salt, especially an acid addition salt.

For use in medicine, the salts of the compounds of formula I will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include addition salts which may, for example, be formed by mixing a solution of the compound according to the invention with a solution of a pharmaceutically acceptable acid such as hydrochloric acid, sulfuric acid, nitric acid, maleic acid, citric acid, tartaric acid, phosphoric acid, p-toluenesulfonic acid, benzenesulfonic acid. Preferred pharmaceuticals salts of the compounds of the present invention are those with the inorganic acids.

The salts may be formed by conventional means, such as by reacting the free base form of the suitable compounds of formula I with one or more equivalents of the appropriate acid in a solvent or medium in which the salt is insoluble or in a solvent such as water which is removed under vacuum.

The present invention also includes within its scope N-oxide of the compounds of formula I above. In general, such N-oxides may be formed on any available nitrogen atom. The N-oxides may be formed by conventional means, such as reacting the compound of formula I with peroxides in suitable solvents. The present invention includes within its scope prodrugs of the compounds of formula I above. In general, such prodrugs will be functional derivatives of the compounds of formula I which are readily convertible in vivo into the required compound of formula I. Conventional procedures for the selection and preparation o suitable prodrug derivatives are described, for example, in "Design of Prodrugs", ed. H. Bundgaard, Elsevier, 1985. A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulfate ester, or reduction or oxidation of a susceptible functionality.

Examples of 5- or 6-membered monocyclic aromatic heterocycle rings are furan, thiophene, pyrrole, imidazole, pyrazole, thiazole, isothiazole, oxazole, isoxazole, thiadiazole, tetrazole, pyridine, pyrazine, pyrimidine, pyridazine, triazine.

Examples of a bicyclic 9-11-membered aromatic heterocycles are benzothiazole, benzoisothiazole, benzoxazole, benzoisoxazole, benzimidazole, benzotriazole, benzothiadiazole, benzooxadiazole, quinoline, isoquinoline, naphthylidine, quinoxaline, phthalazine, cinnoline, indole, indazole, imidazopyridine, benzothiophene, benzofuran, dihydrobenzofuran, benzazepine, benzodiazepine.

Examples of —$C_{1-4}$alkyl-monocyclic heteroaryl rings are $C_{1-4}$alkylsubstituted furan, thiophene, pyrrole, imidazole, pyrazole, thiazole, isothiazole, oxazole, isoxazole, thiadiazole, pyridine, pyrazine, pyrimidine, pyridazine, Examples of —$C_{1-4}$alkyl-heterocycloalkyls are $C_{1-4}$alkyl-substituted tetrahydrofuran, pyran.

In one embodiment each $Y_1$, $Y_2$ are CH and $Y_3$ is N.
In another embodiment each $Y_1$, $Y_2$ and $Y_3$ are CH.
In certain embodiments each $Y_1$, $Y_2$ and $Y_3$ are as above defined and $Ar_1$ is:
  i) phenyl substituted with one substituent $R_a$; where $R_a$ is halo, preferably —Cl or —F, or —$C_{1-4}$alkyl, preferably methyl;
  ii) a thienyl ring optionally substituted with one substituents $R_a$: where $R_a$ is halo, preferably —Cl;
$Ar_2$ is:
  i) phenyl substituted with 1 substituent $R_b$; where $R_b$ is —$OC_{0-4}$alkyl$CF_3$, preferably $OCF_3$, or $R_b$ is —$CF_3$;
$R_1$ is H or $C_{1-4}$ alkyl optionally substituted with halo, preferably H, methyl or ethyl;
$R_2$, $R_3$, $R_4$, and $R_5$ are each independently H, or —$C_{1-4}$ alkyl, preferably H or methyl;
$R_6$ is:
  i) H;
  ii) 1-pyrrolidinyl;
  iii) phenyl optionally substituted with —$CF_3$ or —$OCF_3$;
  iv) morpholin-yl.

Examples of Compounds of Formula I are

2-[ethyl-(4-fluorophenyl)sulfonyl-amino]-N-[[2-[4-(trifluoromethyl)phenyl]-4-pyridyl]methyl]prop-2-enamide;
2-[(4-fluorophenyl)sulfonyl-methyl-amino]-N-[[2-[4-(trifluoromethoxy)phenyl]-4-pyridyl]methyl]prop-2-enamide;
2-[(4-fluorophenyl)sulfonyl-ethyl-amino]-N-[[2-[4-(trifluoromethoxy)phenyl]-4-pyridyl]methyl]prop-2-enamide;
2-[(4-chlorophenyl)sulfonyl-methyl-amino]-N-[[2-[4-(trifluoromethoxy)phenyl]-4-pyridyl]methyl]prop-2-enamide;
2-[(4-chlorophenyl)sulfonyl-ethyl-amino]-N-[[2-[4-(trifluoromethoxy)phenyl]-4-pyridyl]methyl]prop-2-enamide;
2-(methyl(p-tolylsulfonyl)amino)-N-[[2-[4-(trifluoromethoxy)phenyl]-4-pyridyl]-methyl]prop-2-enamide;
2-[(5-chloro-2-thienyl)sulfonyl-ethyl-amino]-N-[[2-[4-(trifluoromethoxy)phenyl]-4-pyridyl]methyl]prop-2-enamide;
2-[ethyl-(4-fluorophenyl)sulfonyl-amino]-N-[[3-[4-(trifluoromethyl)phenyl]-phenyl]-methyl]prop-2-enamide;
2-[(4-chlorophenyl)sulfonyl-methyl-amino]-N-[[3-[4-(trifluoromethyl)phenyl]-phenyl]methyl]prop-2-enamide;
2-[(4-chlorophenyl)sulfonyl-ethyl-amino]-N-[[3-[4-(trifluoromethyl)phenyl]-phenyl]methyl]prop-2-enamide;
2-[ethyl-(4-fluorophenyl)sulfonyl-amino]-N-[[3-[4-(trifluoromethoxy)phenyl]-phenyl]methyl]prop-2-enamide;
2-[(5-chloro-2-thienyl)sulfonyl-ethyl-amino]-N-[[2-[4-(trifluoromethyl)phenyl]-4-pyridyl]methyl]prop-2-enamide;
2-[(4-chlorophenyl)sulfonyl-methyl-amino]-N-[[2-pyrrolidin-1-yl-6-[4-(trifluoromethyl)phenyl]-4-pyridyl]methyl]prop-2-enamide;
2-[(4-chlorophenyl)sulfonyl-ethyl-amino]-N-[[2-pyrrolidin-1-yl-6-[4-(trifluoromethyl)phenyl]-4-pyridyl]methyl]prop-2-enamide;
2-[(5-chloro-2-thienyl)sulfonyl-ethyl-amino]-N-[[2-pyrrolidin-1-yl-6-[4-(trifluoromethyl)phenyl]-4-pyridyl]methyl]prop-2-enamide;
2-[(4-chlorophenyl)sulfonyl-methyl-amino]-N-[[2-morpholino-6-[4-(trifluoromethoxy)phenyl]-4-pyridyl]methyl]prop-2-enamide;
2-[(4-chlorophenyl)sulfonyl-ethyl-amino]-N-[[2-morpholino-6-[4-(trifluoromethoxy)phenyl]-4-pyridyl]methyl]prop-2-enamide;
2-[ethyl-(4-fluorophenyl)sulfonyl-amino]-N-[[2-pyrrolidin-1-yl-6-[4-(trifluoromethoxy)phenyl]-4-pyridyl]methyl]prop-2-enamide;
N-[[2,6-bis[4-(trifluoromethyl)phenyl]-4-pyridyl]methyl]-2-[(4-chlorophenyl)-sulfonyl-ethyl-amino]prop-2-enamide;
N-[[2,6-bis[4-(trifluoromethoxy)phenyl]-4-pyridyl]methyl]-2-[(4-chlorophenyl)-sulfonyl-methyl-amino]prop-2-enamide;
(Z)-2-[(4-fluorophenyl)sulfonyl-methyl-amino]-N-[[2-[4-(trifluoromethoxy)-phenyl]-4-pyridyl]methyl]but-2-enamide;
(Z)-2-[ethyl-(4-fluorophenyl)sulfonyl-amino]-N-[[2-[4-(trifluoromethoxy)phenyl]-4-pyridyl]methyl]but-2-enamide;
(Z)-2-[(4-chlorophenyl)sulfonyl-methyl-amino]-N-[[3-[4-(trifluoromethyl)-phenyl]-phenyl]methyl]but-2-enamide;
(Z)-2-[(4-chlorophenyl)sulfonyl-ethyl-amino]-N-[[3-[4-(trifluoromethyl)phenyl]-phenyl]methyl]but-2-enamide;
1-[ethyl-(4-fluorophenyl)sulfonyl-amino]-N-[[2-[4-(trifluoromethyl)phenyl]-4-pyridyl]methyl]cyclopropanecarboxamide;
1-[ethyl-(4-fluorophenyl)sulfonyl-amino]-N-[[2-[4-(trifluoromethoxy)phenyl]-4-pyridyl]methyl]cyclopropanecarboxamide;
1-[(4-chlorophenyl)sulfonyl-ethyl-amino]-N-[[2-[4-(trifluoromethoxy)phenyl]-4-pyridyl]methyl]cyclopropanecarboxamide;
1-[(5-chloro-2-thienyl)sulfonyl-ethyl-amino]-N-[[2-[4-(trifluoromethoxy)-phenyl]-4-pyridyl]methyl]cyclopropanecarboxamide;
1-[ethyl-(4-fluorophenyl)sulfonyl-amino]-N-[[3-[4-(trifluoromethyl)phenyl]-phenyl]methyl]cyclopropanecarboxamide;
1-[(4-chlorophenyl)sulfonyl-ethyl-amino]-N-[[3-[4-(trifluoromethyl)phenyl]-phenyl]methyl]cyclopropanecarboxamide;
1-[ethyl-(4-fluorophenyl)sulfonyl-amino]-N-[[3-[4-(trifluoromethoxy)phenyl]-phenyl]methyl]cyclopropanecarboxamide;
1-[(4-fluorophenyl)sulfonylamino]-N-[[2-pyrrolidin-1-yl-6-[4-(trifluoromethyl)-phenyl]-4-pyridyl]methyl]cyclopropanecarboxamide;
1-[(4-fluorophenyl)sulfonylamino]-N-[[2-pyrrolidin-1-yl-6-[4-(trifluoromethoxy)phenyl]-4-pyridyl]methyl]cyclopropanecarboxamide;
1-[(5-chloro-2-thienyl)sulfonyl-ethyl-amino]-N-[[2-pyrrolidin-1-yl-6-[4-(trifluoromethyl)phenyl]-4-pyridyl]methyl]cyclopropanecarboxamide;
2-[(3,4-difluorophenyl)sulfonyl-ethyl-amino]-N-[[2-[4-(trifluoromethyl)phenyl]-4-pyridyl]methyl]prop-2-enamide;
2-[(3-difluorophenyl)sulfonyl-ethyl-amino]-N-[[2-[4-(trifluoromethyl)phenyl]-4-pyridyl]methyl]prop-2-enamide;
N-[[2-dimethylamino-6-[4-(trifluoromethyl)phenyl]-4-pyridyl]methyl]-2-[ethyl-(4-fluorophenyl)sulfonyl-amino]prop-2-enamide;
2-[ethyl-(4-fluorophenyl)sulfonyl-amino]-N-[[2-pyrrolidin-1-yl-6-[4-(trifluoromethyl)phenyl]-4-pyridyl]methyl]prop-2-enamide;
2-[(5-chloro-2-thienyl)sulfonyl-ethyl-amino]-N-[[2-dimethylamino-6-[4-(trifluoromethyl)phenyl]-4-pyridyl]methyl]prop-2-enamide;
2-[ethyl-(4-fluorophenyl)sulfonyl-amino]-N-[[2-methoxy-6-[4-(trifluoromethyl)phenyl]-4-pyridyl]methyl]prop-2-enamide;
N-[[2-dimethylamino-6-[4-(trifluoromethyl)phenyl]-4-pyridyl]methyl]-2-(ethyl(2-thienylsulfonyl)amino)prop-2-enamide;

2-[ethyl-(4-fluorophenyl)sulfonyl-amino]-N-[[2-morpholino-6-[4-(trifluoromethyl)phenyl]-4-pyridyl]methyl]prop-2-enamide;

2-[(5-chloro-2-thienyl)sulfonyl-ethyl-amino]-N-[[2-morpholino-6-[4-(trifluoromethyl)phenyl]-4-pyridyl]methyl]prop-2-enamide;

2-[ethyl-(4-fluorophenyl)sulfonyl-amino]-N-[[2-isopropoxy-6-[4-(trifluoromethyl)phenyl]-4-pyridyl]methyl]prop-2-enamide;

N-[[2-dimethylamino-6-[4-(trifluoromethyl)phenyl]-4-pyridyl]methyl]-1-[ethyl-(4-fluorophenyl)sulfonyl-amino]cyclopropanecarboxamide;

1-[(5-chloro-2-thienyl)sulfonyl-ethyl-amino]-N-[[2-[4-(trifluoromethyl)phenyl]-4-pyridyl]methyl]cyclopropanecarboxamide;

1-[(5-chloro-2-thienyl)sulfonyl-ethyl-amino]-N-[[3-[4-(trifluoromethoxy)phenyl]phenyl]methyl]cyclopropanecarboxamide;

1-[ethyl-(4-fluorophenyl)sulfonyl-amino]-N-[[2-methoxy-6-[4-(trifluoromethyl)phenyl]-4-pyridyl]methyl]cyclopropanecarboxamide;

1-[ethyl-(4-fluorophenyl)sulfonyl-amino]-N-[[2-isopropoxy-6-[4-(trifluoromethyl)phenyl]-4-pyridyl]methyl]cyclopropanecarboxamide;

1-[(5-chloro-2-thienyl)sulfonyl-ethyl-amino]-N-[[2-methoxy-6-[4-(trifluoromethyl)phenyl]-4-pyridyl]methyl]cyclopropanecarboxamide;

1-[ethyl-(4-fluorophenyl)sulfonyl-amino]-N-[[2-pyrrolidin-1-yl-6-[4-(trifluoromethyl)phenyl]-4-pyridyl]methyl]cyclopropanecarboxamide;

N-[[2-ethoxy-6-[4-(trifluoromethyl)phenyl]-4-pyridyl]methyl]-1-[ethyl-(4-fluorophenyl)sulfonyl-amino]cyclopropanecarboxamide;

1-[(5-chloro-2-thienyl)sulfonyl-ethyl-amino]-N-[[2-ethoxy-6-[4-(trifluoromethyl)phenyl]-4-pyridyl]methyl]cyclopropanecarboxamide;

2-[ethyl-(4-fluorophenyl)sulfonyl-amino]-N-[[1-oxido-2-[4-(trifluoromethyl)phenyl]pyridin-1-ium-4-yl]methyl]prop-2-enamide;

2-[(5-chloro-2-thienyl)sulfonyl-ethyl-amino]-N-[[3-[4-(trifluoromethoxy)phenyl]phenyl]methyl]prop-2-enamide;

2-[(4-fluorophenyl)sulfonyl-methyl-amino]-N-[[2-[4-(trifluoromethyl)phenyl]-4-pyridyl]methyl]prop-2-enamide;

1-[(4-fluorophenyl)sulfonyl-methyl-amino]-N-[[3-[4-(trifluoromethoxy)phenyl]phenyl]methyl]cyclopropanecarboxamide;

1-[(4-fluorophenyl)sulfonyl-methyl-amino]-N-[[3-[4-(trifluoromethyl)phenyl]phenyl]methyl]cyclopropanecarboxamide;

1-[(5-chloro-2-thienyl)sulfonyl-ethyl-amino]-N-[[3-[4-(trifluoromethyl)phenyl]phenyl]methyl]cyclopropanecarboxamide;

1-[ethyl-(4-fluorophenyl)sulfonyl-amino]-N-[[4-[4-(trifluoromethyl)phenyl]-2-pyridyl]methyl]cyclopropanecarboxamide;

1-[ethyl-(4-fluorophenyl)sulfonyl-amino]-N-[[2-pyrrolidin-1-yl-6-[4-(trifluoromethoxy)phenyl]-4-pyridyl]methyl]cyclopropanecarboxamide;

1-[ethyl-(4-fluorophenyl)sulfonyl-amino]-N-[[2-morpholino-6-[4-(trifluoromethyl)phenyl]-4-pyridyl]methyl]cyclopropanecarboxamide;

N-[[2-[4-(cyclopropylmethyl)piperazin-1-yl]-6-[4-(trifluoromethoxy)phenyl]-4-pyridyl]methyl]-2-[ethyl-(4-fluorophenyl)sulfonyl-amino]prop-2-enamide;

N-[[2-[4-(cyclopropylmethyl)piperazin-1-yl]-6-[4-(trifluoromethyl)phenyl]-4-pyridyl]methyl]-1-[ethyl-(4-fluorophenyl)sulfonyl-amino]cyclopropanecarboxamide;

1-[(5-chloro-2-thienyl)sulfonyl-ethyl-amino]-N-[[2-[4-(cyclopropylmethyl)piperazin-1-yl]-6-[4-(trifluoromethyl)phenyl]-4-pyridyl]methyl]cyclopropanecarboxamide;

N-[[2-(4-cyclohexylpiperazin-1-yl)-6-[4-(trifluoromethyl)phenyl]-4-pyridyl]methyl]-1-[ethyl-(4-fluorophenyl)sulfonyl-amino]cyclopropanecarboxamide;

1-[(5-chloro-2-thienyl)sulfonyl-ethyl-amino]-N-[[2-(4-cyclohexylpiperazin-1-yl)-6-[4-(trifluoromethyl)phenyl]-4-pyridyl]methyl]cyclopropanecarboxamide.

Compounds of Formula (I) are amides that can be prepared by standard procedures, by the reaction of a compound of general formula i with the corresponding amine ii in the presence of an acidic function activator, preferably diethyl cyanophosphonate DEPC as illustrated in the following Scheme 1.

Scheme 1

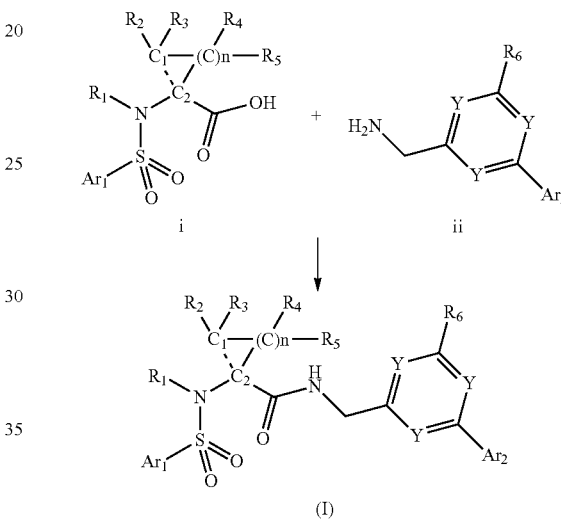

(I)

According to a first preferred embodiment, the invention relates to compounds of formula (IA)

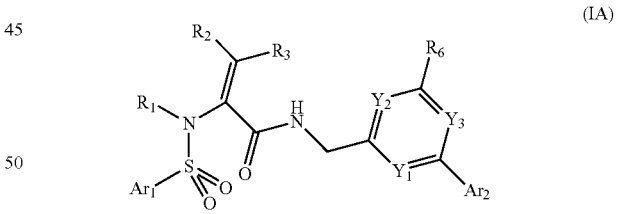

(IA)

wherein:

$Ar_1$ is:
i) phenyl substituted with 0, 1, 2 or 3 substituents $R_a$; or
ii) a 5-6-membered monocyclic aromatic heterocycle ring optionally substituted with one or two substituents $R_a$; where each $R_a$ is independently halo, —$C_{1-4}$alkyl, —$OC_{1-4}$alkyl, —CN, —$CF_3$, —$OCF_3$, —$NO_2$, —C(O)$C_{1-4}$alkyl or —$CO_2$H;

$Ar_2$ is:
i) phenyl substituted with 0, 1, 2 or 3 substituents $R_b$; where each $R_b$ is independently halo, —$C_{1-4}$alkyl, —C(O)$NR_cR_d$, —$OC_{1-4}$alkyl, —$OC_{0-4}$alkyl$CF_3$, —CN, —$CF_3$, —$CF_2$H, —$NO_2$, —$NR_cR_d$, $S(O)_{0-2}C_{1-4}$alkyl, —C(O)$C_{1-4}$alkyl, $S(O)(O)NH_2$, —$(CH_2)_{0-2}$-morpholinyl, piperidin-1-yl, piperazinyl, said piperazinyl optionally substituted with a methyl, or two $R_b$ substituents on adjacent carbon atoms taken together form —O(CH$_2$)$_{1-2}$O—;

ii) pyridyl substituted with 0, 1 or 2 substituents $R_e$; where each $R_e$ is independently selected from halo, —C$_{1-4}$alkyl, —OC$_{1-4}$alkyl, —CF$_3$, —NR$_c$R$_d$ or 4-morpholinyl;

iii) a bicyclic 9-11-membered aromatic heterocycle optionally substituted with 1 substituent $R_f$; where $R_f$ is —C$_{1-4}$alkyl;

$R_c$ and $R_d$ are each independently selected from H or —C$_{1-4}$alkyl;

$R_1$ is H, C$_{1-4}$alkyl-O—C$_{1-4}$alkyl, or C$_{1-4}$alkyl optionally substituted with halo;

$R_2$ and $R_3$ and are each independently H, halo or —C$_{1-4}$alkyl;

each $Y_1$, $Y_2$ and $Y_3$ is independently CH or N;

$R_6$ 1 S i) H, —C$_{1-4}$alkyl, —CF$_3$, —OR$_z$ or —NR$_h$R$_i$;

where $R_h$ is selected from a) H, —C$_{0-4}$alkylCF$_3$, —C$_{1-4}$alkyl-N(CH$_3$)$_2$, saturated C$_{3-7}$cycloalkyl or —C$_{1-4}$alkyl-monocyclic heteroaryl ring;

b) —C$_{1-5}$alkyl optionally substituted with OH;

c) —C$_{1-4}$alkyl-heterocycloalkyl, said heterocycloalkyl being optionally substituted with —C$_{1-4}$alkyl: or d) —C$_{0-4}$alkyl-phenyl, said phenyl optionally substituted with one or two N moieties; where each $R_j$ is independently halo, —OC$_{1-4}$alkyl, $R_Z$ is —C$_{1-4}$alkyl, —C$_{1-4}$alkylCF$_3$ or —C$_{1-4}$alkyl-heterocycloalkyl;

ii) 1-pyrrolidinyl optionally substituted with a moiety selected from the group consisting of —NR$_k$R$_i$ and —C$_{1-4}$alkyl, said —C$_{1-4}$alkyl optionally substituted with —OH;

iii) 1-piperidinyl optionally substituted with —C$_{1-4}$alkyl, —C(O)NH$_2$, —CO$_2$C$_{1-4}$alkyl or —C$_{0-4}$alkyl-phenyl;

iv) piperazinyl optionally substituted with —C$_{1-5}$alkyl, —OC$_{1-4}$alkyl, —C$_{0-4}$alkylpyridyl, —C$_{0-4}$alkyl-1-methyl-piperidin-4-yl, —C$_{0-4}$alkylNR$_k$R$_i$ or —C$_{0-4}$alkyl-phenyl, said phenyl optionally substituted with one or two $R_T$ substituents; where each $R_T$ substituent is selected from the group consisting of halo, —OCF$_3$, —C$_{1-4}$alkyl, —OC$_{1-4}$alkyl, —CO$_2$C$_{1-4}$alkyl, —C(O)C$_{1-4}$alkyl and —C$_{0-4}$alkylNR$_k$R$_i$, or two $R_T$ substituents on adjacent carbon atoms taken together form —O(CH$_2$)$_{1-2}$O—;

v) phenyl optionally substituted with halo, —CF$_3$, —OCF$_3$;

vi) pyridyl;

vii) morpholin-yl;

$R_k$ is H, —C$_{1-4}$alkyl or —C(O)$_{1-2}$C$_{1-4}$alkyl;

$R_i$ is H or C$_{1-4}$alkyl.

In one embodiment, in the compounds of formula (IA) each $Y_1$, $Y_2$ are CH and $Y_3$ is N.

In another embodiment in the compounds of formula (IA) each $Y_1$, $Y_2$ and $Y_3$ are CH In certain embodiments in the compounds of formula (IA) each $Y_1$, $Y_2$ and $Y_3$ are as above defined and $Ar_1$ is:

i) phenyl substituted with one substituent $R_a$; where $R_a$ is halo, preferably —Cl or —F, or —C$_{1-4}$alkyl, preferably methyl;

ii) a thienyl ring optionally substituted with one substituents $R_a$: where $R_a$ is halo, preferably —Cl;

$Ar_2$ is:

i) phenyl substituted with 1 substituent $R_b$; where $R_b$ is —OC$_{0-4}$alkylCF$_{3,}$ preferably OCF$_3$, or $R_b$ is —CF$_3$;

$R_1$ is H or C$_{1-4}$ alkyl optionally substituted with halo, preferably H, methyl or ethyl;

$R_2$, $R_3$, $R_4$, and $R_5$ are each independently H, or —C$_{1-4}$ alkyl, preferably H or methyl;

$R_6$ 1 S:

i) H;

ii) 1-pyrrolidinyl;

iii) phenyl optionally substituted with —CF$_3$ or —OCF$_3$;

iv) morpholin-yl.

Examples of Compounds of Formula (IA) are

2-[ethyl-(4-fluorophenyl)sulfonyl-amino]-N-[[2-[4-(trifluoromethyl)phenyl]-4-pyridyl]methyl]prop-2-enamide 2-[(4-fluorophenyl)sulfonyl-methyl-amino]-N-[[2-[4-(trifluoromethoxy)phenyl]-4-pyridyl]methyl]prop-2-enamide;

2-[(4-fluorophenyl)sulfonyl-ethyl-amino]-N-[[2-[4-(trifluoromethoxy)phenyl]-4-pyridyl]methyl]prop-2-enamide;

2-[(4-chlorophenyl)sulfonyl-methyl-amino]-N-[[2-[4-(trifluoromethoxy)phenyl]-4-pyridyl]methyl]prop-2-enamide;

2-[(4-chlorophenyl)sulfonyl-ethyl-amino]-N-[[2-[4-(trifluoromethoxy)phenyl]-4-pyridyl]methyl]prop-2-enamide;

2-(methyl(p-tolylsulfonyl)amino)-N-[[2-[4-(trifluoromethoxy)phenyl]-4-pyridyl]-methyl]prop-2-enamide;

2-[(5-chloro-2-thienyl)sulfonyl-ethyl-amino]-N-[[2-[4-(trifluoromethoxy)-phenyl]-4-pyridyl]methyl]prop-2-enamide;

2-[ethyl-(4-fluorophenyl)sulfonyl-amino]-N-[[3-[4-(trifluoromethyl)phenyl]-phenyl]-methyl]prop-2-enamide;

2-[(4-chlorophenyl)sulfonyl-methyl-amino]-N-[[3-[4-(trifluoromethyl)phenyl]-phenyl]methyl]prop-2-enamide;

2-[(4-chlorophenyl)sulfonyl-ethyl-amino]-N-[[3-[4-(trifluoromethyl)phenyl]-phenyl]methyl]prop-2-enamide;

2-[ethyl-(4-fluorophenyl)sulfonyl-amino]-N-[[3-[4-(trifluoromethoxy)phenyl]-phenyl]methyl]prop-2-enamide 2-[(5-chloro-2-thienyl)sulfonyl-ethyl-amino]-N-[[2-[4-(trifluoromethyl)phenyl]-4-pyridyl]methyl]prop-2-enamide 2-[(4-chlorophenyl)sulfonyl-methyl-amino]-N-[[2-pyrrolidin-1-yl-6-[4-(trifluoromethyl)phenyl]-4-pyridyl]methyl] prop-2-enamide;

2-[(4-chlorophenyl)sulfonyl-ethyl-amino]-N-[[2-pyrrolidin-1-yl-6-[4-(trifluoromethyl)phenyl]-4-pyridyl]methyl] prop-2-enamide 2-[(5-chloro-2-thienyl)sulfonyl-ethyl-amino]-N-[[2-pyrrolidin-1-yl-6-[4-(trifluoromethyl)phenyl]-4-pyridyl]methyl] prop-2-enamide 2-[(4-chlorophenyl)sulfonyl-methyl-amino]-N-[[2-morpholino-6-[4-(trifluoromethoxy)phenyl]-4-pyridyl]methyl]prop-2-enamide;

2-[(4-chlorophenyl)sulfonyl-ethyl-amino]-N-[[2-morpholino-6-[4-(trifluoromethoxy)phenyl]-4-pyridyl]methyl]prop-2-enamide;

2-[ethyl-(4-fluorophenyl)sulfonyl-amino]-N-[[2-pyrrolidin-1-yl-6-[4-(trifluoromethoxy)phenyl]-4-pyridyl]methyl] prop-2-enamide;

N-[[2,6-bis[4-(trifluoromethyl)phenyl]-4-pyridyl]methyl]-2-[(4-chlorophenyl)-sulfonyl-ethyl-amino]prop-2-enamide;

N-[[2,6-bis[4-(trifluoromethoxy)phenyl]-4-pyridyl]methyl]-2-[(4-chlorophenyl)-sulfonyl-methyl-amino]prop-2-enamide;

(Z)-2-[(4-fluorophenyl)sulfonyl-methyl-amino]-N-[[2-[4-(trifluoromethoxy)-phenyl]-4-pyridyl]methyl]but-2-enamide;

(Z)-2-[ethyl-(4-fluorophenyl)sulfonyl-amino]-N-[[2-[4-(trifluoromethoxy)-phenyl]-4-pyridyl]methyl]but-2-enamide;

(Z)-2-[(4-chlorophenyl)sulfonyl-methyl-amino]-N-[[3-[4-(trifluoromethyl)-phenyl]-phenyl]methyl]but-2-enamide;

(Z)-2-[(4-chlorophenyl)sulfonyl-ethyl-amino]-N-[[3-[4-(trifluoromethyl)phenyl]-phenyl]methyl]but-2-enamide;

2-[(3,4-difluorophenyl)sulfonyl-ethyl-amino]-N-[[2-[4-(trifluoromethyl)phenyl]-4-pyridyl]methyl]prop-2-enamide;
2-[(3-difluorophenyl)sulfonyl-ethyl-amino]-N-[[2-[4-(trifluoromethyl)phenyl]-4-pyridyl]methyl]prop-2-enamide;
N-[[2-dimethylamino-6-[4-(trifluoromethyl)phenyl]-4-pyridyl]methyl]-2-[ethyl-(4-fluorophenyl)sulfonyl-amino]prop-2-enamide;
2-[ethyl-(4-fluorophenyl)sulfonyl-amino]-N-[[2-pyrrolidin-1-yl-6-[4-(trifluoromethyl)phenyl]-4-pyridyl]methyl]prop-2-enamide;
2-[(5-chloro-2-thienyl)sulfonyl-ethyl-amino]-N-[[2-dimethylamino-6-[4-(trifluoromethyl)phenyl]-4-pyridyl]methyl]prop-2-enamide;
2-[ethyl-(4-fluorophenyl)sulfonyl-amino]-N-[[2-methoxy-6-[4-(trifluoromethyl)phenyl]-4-pyridyl]methyl]prop-2-enamide;
N-[[2-dimethylamino-6-[4-(trifluoromethyl)phenyl]-4-pyridyl]methyl]-2-(ethyl(2-thienylsulfonyl)amino)prop-2-enamide;
2-[ethyl-(4-fluorophenyl)sulfonyl-amino]-N-[[2-morpholino-6-[4-(trifluoromethyl)phenyl]-4-pyridyl]methyl]prop-2-enamide;
2-[(5-chloro-2-thienyl)sulfonyl-ethyl-amino]-N-[[2-morpholino-6-[4-(trifluoromethyl)phenyl]-4-pyridyl]methyl]prop-2-enamide;
2-[ethyl-(4-fluorophenyl)sulfonyl-amino]-N-[[2-isopropoxy-6-[4-(trifluoromethyl)phenyl]-4-pyridyl]methyl]prop-2-enamide;
2-[ethyl-(4-fluorophenyl)sulfonyl-amino]-N-[[1-oxido-2-[4-(trifluoromethyl)phenyl]pyridin-1-ium-4-yl]methyl]prop-2-enamide;
2-[(5-chloro-2-thienyl)sulfonyl-ethyl-amino]-N-[[3-[4-(trifluoromethoxy)phenyl]phenyl]methyl]prop-2-enamide;
2-[(4-fluorophenyl)sulfonyl-methyl-amino]-N-[[2-[4-(trifluoromethyl)phenyl]-4-pyridyl]methyl]prop-2-enamide;
N-[[2-[4-(cyclopropylmethyl)piperazin-1-yl]-6-[4-(trifluoromethoxy)phenyl]-4-pyridyl]methyl]-2-[ethyl-(4-fluorophenyl)sulfonyl-amino]prop-2-enamide.

According to a second preferred embodiment, the invention relates to compounds of formula (IB)

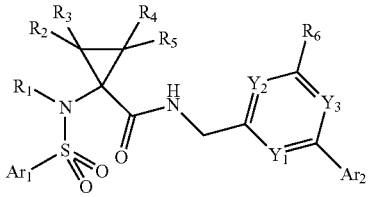

(IB)

wherein:

$Ar_1$ is:
i) phenyl substituted with 0, 1, 2 or 3 substituents $R_a$; or
ii) a 5- or 6-membered monocyclic aromatic heterocycle ring optionally substituted with one or two substituents $R_a$; where each $R_a$ is independently halo, —$C_{1-4}$alkyl, —$OC_{1-4}$alkyl, —CN, —$CF_3$, —$OCF_3$, —$NO_2$, —$C(O)C_{1-4}$alkyl or —$CO_2H$;

$Ar_2$ is:
i) phenyl substituted with 0, 1, 2 or 3 substituents $R_b$; where each $R_b$ is independently halo, —$C_{1-4}$alkyl, —$C(O)NR_cR_d$, —$OC_{1-4}$alkyl, —$OC_{0-4}$alkylCF$_3$, —CN, —$CF_3$, —$OCF_2H$, —$NO_2$, —$NR_cR_d$, —$S(O)_{0-2}C_{1-4}$alkyl, —$C(O)C_{1-4}$alkyl, $S(O)(O)NH_2$, —$(CH_2)_{0-2}$-morpholinyl, piperidin-1yl, piperazinyl, said piperazinyl optionally substituted with a methyl, or two $R_b$ substituents on adjacent carbon atoms taken together form —$O(CH_2)_{1-2}O$—;
ii) pyridyl substituted with 0, 1 or 2 substituents $R_e$; where each $R_e$ is independently selected from halo, —$C_{1-4}$alkyl, —$OC_{1-4}$alkyl, —$CF_3$, —$NR_eR_d$ or 4-morpholinyl; or iii) a bicyclic 9-11-membered aromatic heterocycle optionally substituted with 1 substituent $R_f$; where $R_f$ is —$C_{1-4}$alkyl;

$R_c$ and $R_d$ are each independently selected from H or —$C_{1-4}$alkyl;

$R_1$ is H, $C_{1-4}$alkyl-O—$C_{1-4}$alkyl, or $C_{1-4}$alkyl optionally substituted with halo; $R_2$, $R_3$, $R_4$, and $R_5$ are each independently H, halo or —$C_{1-4}$alkyl;

each $Y_1$, $Y_2$ and $Y_3$ is independently CH or N;

$R_6$ is
i) H, —$C_{1-4}$alkyl, —$CF_3$, —$OR_Z$ or —$NR_hR_i$;
where $R_h$ is selected from
a) H, —$C_{0-4}$alkylCF$_3$, —$C_{1-4}$alkyl-N(CH$_3$)$_2$, saturated $C_{3-7}$cycloalkyl or —$C_{1-4}$alkyl-monocyclic heteroaryl ring;
b) —$C_{1-5}$alkyl optionally substituted with OH;
c) —$C_{1-4}$alkyl-heterocycloalkyl, said heterocycloalkyl being optionally substituted with —$C_{1-4}$alkyl: or
d) —$C_{0-4}$alkyl-phenyl, said phenyl optionally substituted with one or two N moieties; where each $R_j$ is independently halo, —$OC_{1-4}$alkyl,
$R_Z$ is —$C_{1-4}$alkyl, —$C_{1-4}$alkylCF$_3$ or —$C_{1-4}$alkyl-heterocycloalkyl;
ii) 1-pyrrolidinyl optionally substituted with a moiety selected from the group consisting of —$NR_kR_i$ and —$C_{1-4}$alkyl, said —$C_{1-4}$alkyl optionally substituted with —OH;
iii) 1-piperidinyl optionally substituted with —$C_{1-4}$alkyl, —$C(O)NH_2$, —$CO_2C_{1-4}$alkyl or —$C_{0-4}$alkyl-phenyl;
iv) piperazinyl optionally substituted with —$C_{1-5}$alkyl, —$OC_{1-4}$alkyl, —$C_{0-4}$alkylpyridyl, —$C_{0-4}$alkyl-1-methyl-piperidin-4-yl, —$C_{0-4}$alkylNR$_k$R$_i$ or —$C_{0-4}$alkyl-phenyl, said phenyl optionally substituted with one or two $R_T$ substituents; where each $R_T$ substituent is selected from the group consisting of halo, —$OCF_3$, —$C_{1-4}$alkyl, —$OC_{1-4}$alkyl, —$CO_2$ $C_{1-4}$alkyl, —$C(O)$ $C_{1-4}$alkyl and —$C_{0-4}$alkylNR$_k$R$_i$, or two $R_T$ substituents on adjacent carbon atoms taken together form —$O(CH_2)_{1-2}O$—;
v) phenyl optionally substituted with halo, $CF_3$;
vi) pyridyl;
vii) morpholin-yl;

$R_k$ is H, —$C_{1-4}$alkyl or —$C(O)_{1-2}C_{1-4}$alkyl;
$R_i$ is H or $C_{1-4}$alkyl In one embodiment, in the compounds of formula (IB) each $Y_1$, $Y_2$ are CH and $Y_3$ is N.

In another embodiment in the compounds of formula (IB) each $Y_1$, $Y_2$ and $Y_3$ are CH.

In another embodiments, in the compounds of formula (IB) each $Y_1$, $Y_2$ and $Y_3$ are as above defined and
$Ar_1$ is:
i) phenyl substituted with one substituent $R_a$; where $R_a$ is halo, preferably —Cl or —F, or —$C_{1-4}$alkyl, preferably methyl;
ii) a thienyl ring optionally substituted with one substituents $R_a$: where $R_a$ is halo, preferably —Cl; $Ar_2$ is:
i) phenyl substituted with 1 substituent $R_b$; where $R_b$ is —$OC_{0-4}$alkylCF$_{3.5}$ preferably OCF$_3$, or $R_b$ is —$CF_3$;

$R_1$ is H or $C_{1-4}$ alkyl optionally substituted with halo, preferably H, methyl or ethyl; $R_2$, $R_3$, $R_4$, and $R_5$ are each independently H, or —$C_{1-4}$alkyl, preferably H or methyl;
$R_6$ is:
i) H;
ii) 1-pyrrolidinyl;
iii) phenyl optionally substituted with —$CF_3$ or —$OCF_3$;
iv) morpholin-yl.

Examples of Compounds of Formula (IB) are

1-[ethyl-(4-fluorophenyl)sulfonyl-amino]-N-[[2-[4-(trifluoromethyl)phenyl]-4-pyridyl]methyl]cyclopropanecarboxamide;

1-[ethyl-(4-fluorophenyl)sulfonyl-amino]-N-[[2-[4-(trifluoromethoxy)phenyl]-4-pyridyl]methyl]cyclopropanecarboxamide;
1-[(4-chlorophenyl)sulfonyl-ethyl-amino]-N-[[2-[4-(trifluoromethoxy)phenyl]-4-pyridyl]methyl]cyclopropanecarboxamide;
1-[(5-chloro-2-thienyl)sulfonyl-ethyl-amino]-N-[[2-[4-(trifluoromethoxy)-phenyl]-4-pyridyl]methyl]cyclopropanecarboxamide;
1-[ethyl-(4-fluorophenyl)sulfonyl-amino]-N-[[3-[4-(trifluoromethyl)phenyl]-phenyl]-methyl]cyclopropanecarboxamide;
1-[(4-chlorophenyl)sulfonyl-ethyl-amino]-N-[[3-[4-(trifluoromethyl)phenyl]-phenyl]methyl]cyclopropanecarboxamide;
1-[ethyl-(4-fluorophenyl)sulfonyl-amino]-N-[[3-[4-(trifluoromethoxy)phenyl]-phenyl]methyl]cyclopropanecarboxamide;
1-[(4-fluorophenyl)sulfonylamino]-N-[[2-pyrrolidin-1-yl-6-[4-(trifluoromethyl)-phenyl]-4-pyridyl]methyl]cyclopropanecarboxamide;
1-[(4-fluorophenyl)sulfonylamino]-N-[[2-pyrrolidin-1-yl-6-[4-(trifluoromethoxy)phenyl]-4-pyridyl]methyl]cyclopropanecarboxamide;
1-[(5-chloro-2-thienyl)sulfonyl-ethyl-amino]-N-[[2-pyrrolidin-1-yl-6-[4-(trifluoromethyl)phenyl]-4-pyridyl]methyl]cyclopropanecarboxamide;
N-[[2-dimethylamino-6-[4-(trifluoromethyl)phenyl]-4-pyridyl]methyl]-1-[ethyl-(4-fluorophenyl)sulfonyl-amino]cyclopropanecarboxamide;
1-[(5-chloro-2-thienyl)sulfonyl-ethyl-amino]-N-[[2-[4-(trifluoromethyl)phenyl]-4-pyridyl]methyl]cyclopropanecarboxamide;
1-[(5-chloro-2-thienyl)sulfonyl-ethyl-amino]-N-[[3-[4-(trifluoromethoxy)phenyl]phenyl]methyl]cyclopropanecarboxamide;
1-[ethyl-(4-fluorophenyl)sulfonyl-amino]-N-[[2-methoxy-6-[4-(trifluoromethyl)phenyl]-4-pyridyl]methyl]cyclopropanecarboxamide;
1-[ethyl-(4-fluorophenyl)sulfonyl-amino]-N-[[2-isopropoxy-6-[4-(trifluoromethyl)phenyl]-4-pyridyl]methyl]cyclopropanecarboxamide;
1-[(5-chloro-2-thienyl)sulfonyl-ethyl-amino]-N-[[2-methoxy-6-[4-(trifluoromethyl)phenyl]-4-pyridyl]methyl]cyclopropanecarboxamide;
1-[ethyl-(4-fluorophenyl)sulfonyl-amino]-N-[[2-pyrrolidin-1-yl-6-[4-(trifluoromethyl)phenyl]-4-pyridyl]methyl]cyclopropanecarboxamide;
N-[[2-ethoxy-6-[4-(trifluoromethyl)phenyl]-4-pyridyl]methyl]-1-[ethyl-(4-fluorophenyl)sulfonyl-amino]cyclopropanecarboxamide;
1-[(5-chloro-2-thienyl)sulfonyl-ethyl-amino]-N-[[2-ethoxy-6-[4-(trifluoromethyl)phenyl]-4-pyridyl]methyl]cyclopropanecarboxamide;
1-[(4-fluorophenyl)sulfonyl-methyl-amino]-N-[[3-[4-(trifluoromethoxy)phenyl]phenyl]methyl]cyclopropanecarboxamide;
1-[(4-fluorophenyl)sulfonyl-methyl-amino]-N-[[3-[4-(trifluoromethyl)phenyl]phenyl]methyl]cyclopropanecarboxamide;
1-[(5-chloro-2-thienyl)sulfonyl-ethyl-amino]-N-[[3-[4-(trifluoromethyl)phenyl]phenyl]methyl]cyclopropanecarboxamide;
1-[ethyl-(4-fluorophenyl)sulfonyl-amino]-N-[[4-[4-(trifluoromethyl)phenyl]-2-pyridyl]methyl]cyclopropanecarboxamide;
1-[ethyl-(4-fluorophenyl)sulfonyl-amino]-N-[[2-pyrrolidin-1-yl-6-[4-(trifluoromethoxy)phenyl]-4-pyridyl]methyl]cyclopropanecarboxamide;
1-[ethyl-(4-fluorophenyl)sulfonyl-amino]-N-[[2-morpholino-6-[4-(trifluoromethyl)phenyl]-4-pyridyl]methyl]cyclopropanecarboxamide;
N-[[2-[4-(cyclopropylmethyl)piperazin-1-yl]-6-[4-(trifluoromethyl)phenyl]-4-pyridyl]methyl]-1-[ethyl-(4-fluorophenyl)sulfonyl-amino]cyclopropanecarboxamide;
1-[(5-chloro-2-thienyl)sulfonyl-ethyl-amino]-N-[[2-[4-(cyclopropylmethyl)piperazin-1-yl]-6-[4-(trifluoromethyl)phenyl]-4-pyridyl]methyl]cyclopropanecarboxamide;
N-[[2-(4-cyclohexylpiperazin-1-yl)-6-[4-(trifluoromethyl)phenyl]-4-pyridyl]methyl]-1-[ethyl-(4-fluorophenyl)sulfonyl-amino]cyclopropanecarboxamide;
1-[(5-chloro-2-thienyl)sulfonyl-ethyl-amino]-N-[[2-(4-cyclohexylpiperazin-1-yl)-6-[4-(trifluoromethyl)phenyl]-4-pyridyl]methyl]cyclopropanecarboxamide.

Compounds of formula (IA) and (IB) are amides that can be prepared by standard procedures, by the reaction of a compound of general formula (IIa) or (IIb) with the corresponding amine (III) in the presence of an acidic function activator such as, for example, DEPC, as illustrated in the following Scheme 2.

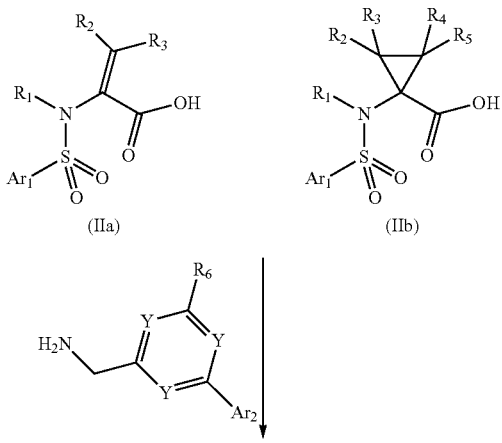

Scheme 2

-continued

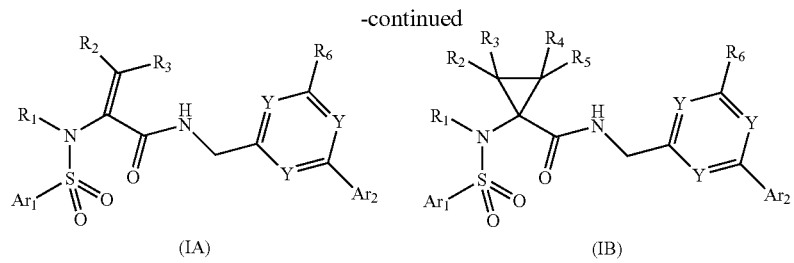

Reagents: DEPC, THF

Compositions of the Invention

The compounds of formula (IIa) or (IIb) and the compounds of formula (III) are known compounds that can be prepared according to well established procedures, as it will be illustrated in the Examples and in Schemes 3-7 accompanying the Examples.

Compositions of the Invention

The present invention also provides pharmaceutical compositions that comprise compounds of the present invention. The pharmaceutical compositions comprise compounds of the present invention that may be formulated together with one or more non-toxic pharmaceutically acceptable carriers.

The pharmaceutical compositions of this invention can be administered to humans and other mammals orally, rectally, parenterally, intracisternally, intravaginally, intraperitoneally, topically (as by powders, ointments or drops), buccally or as an oral or nasal spray.

Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents that delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly (anhydrides). Depot injectable formulations are also prepared by entrapping the drug in liposomes or microemulsions that are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragées, capsules, pills and granules can be prepared with coatings and shells such as enteric coatings and other coatings well-known in the pharmaceutical formulating art. They may optionally contain opacifying agents and may also be of a composition such that they release the active ingredient (s) only, or preferentially, in a certain part of the intestinal tract, optionally, in a delayed manner. Examples of embedding compositions that can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals, which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospho lipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants that may be required. Ophthalmic formulations, eye ointments, powders and solutions are also contemplated as being within the scope of this invention.

In the treatment of painful conditions such as those listed below, a suitable indicated dosage level is about 0.1 mg to 2000 mg/day, preferably from about 5 mg to 1000 mg per day. The compounds may be administered on a regimen of 1 to 4 times a day.

It will be appreciated that the amount of a compound of formula I required for use in any treatment will vary not only with the particular compounds or compositions selected but also with the route of administration, the nature of the condition being treated, and the age and condition of the patient.

The agents of invention are useful TRPA1 receptor antagonists for the treatment of pain of various genesis or etiology and as anti-inflammatory agents for the treatment of inflammatory reactions, diseases or conditions. They are useful for the treatment of inflammatory pain, for the treatment of hyperalgesia, and in particular for the treatment of severe chronic pain. They are, for example, useful for the treatment of neuropathic pain conditions such as diabetic neuropathy, chemotherapy-induced neuropathy and post-herpetic neuralgia; "non-painful" neuropathies, complex regional pain syndromes, pain associated with carcinoma, often referred to as cancer pain, central nervous system pain, such as pain due to spinal cord or brain stem damage, low back pain, sciatica and ankylosing spondylitis, inflammation consequential to trauma, e.g. associated with burns or subsequent to surgical intervention, e.g. as post-operative analgesics, as well as for the treatment of inflammatory pain of diverse genesis, e.g. for the treatment of osteoarthritis and rheumatoid arthritis.

Other forms of pain associated with the activity of TRPA1 are headache, dental pain, pelvic pain, migraine, mastalgia and visceral pain.

The disorders in which TRPA1 is involved are not limited to pain. Such diseases include: nerve-related diseases, e.g. neuropathies, nerve injury and stroke; irritable bowel syndrome; gastrointestinal disorders, e.g. gastro-oesophageal reflux disease, Crohn's disease; respiratory diseases, e.g. asthma, chronic obstructive pulmonary disease, cough;

urinary incontinence; urinary bladder hypersensitiveness; skin diseases, e.g. psoriasis, dermatitis; cardiac diseases e.g. myocardial ischemia; hair growth related disorders e.g. hirsutism, alopecia; rhinitis; pancreatitis; vulvodynia; psychiatric disorders, e.g. anxiety or fear; obesity.

The compounds of the present invention have potent analgesic effect and potential anti-inflammatory activity and their pharmaceutically formulations are thought to alleviate or to treat in particular neuropathic pain conditions such as diabetic neuropathy and post-herpetic neuralgia, urinary incontinence, COPD and cough.

The invention will be now illustrated by means of the following examples.

EXAMPLES

All commercially available compounds were purchased from Vendors and were used without further purification. Reaction courses were monitored by thin-layer chromatography on silica gel (precoated $F_{254}$ Merck plates), the spots were examined with UV light and visualized with aqueous $KMnO_4$. Flash chromatography was performed using Merck silica gel (230-240 mesh). $^1$H-NMR spectra were recorded on Varian 400 MHz spectrometer or Varian 200 MHz using TMS as internal standard. Mass spectra were obtained with a Waters-Micromass ZMD spectrometer.

Abbrev.: TEA (triethylamine), DMF (dimethylformamide), DEPC (diethylcyanophosphonate), TetrakisPd (tetrakistriphenylphosphine Palladium(O)), DME (Dimethoxyethane), XPhos (2-dicyclohexylphosphino-2',4',6'-triisopropylbiphenyl).

Example 1

2-[ethyl-(4-fluorophenyl)sulfonyl-amino]-N-[[2-[4-(trifluoromethyl)phenyl]-4-pyridyl]methyl]prop-2-enamide

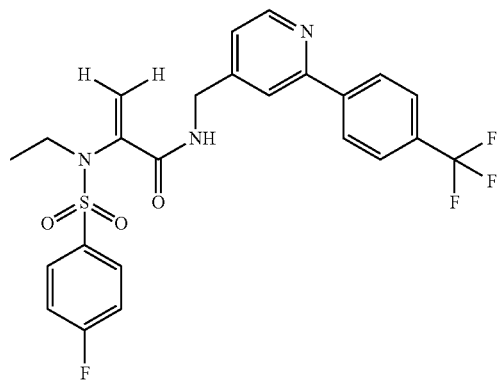 [SMILES: C=C(C(=O)NCc1ccnc(-c2ccc(C(F)(F)F)cc2)c1)N(CC)S(=O)(=O)c1ccc(F)cc1]

Synthesis of methyl (2S)-2-[(4-fluorophenyl)sulfonylamino]-3-hydroxy-propanoate 2A A suspension of L-serine-methyl ester hydrochloride 1 (5 g, 32.13 mmol) in $CH_2Cl_2$ (100 mL) was added with TEA (1.1 mol eq, 4.9 mL) and the mixture stirred at r.t. for 10 minutes. Then 4-fluorobenzensulfonyl chloride (1 mol eq, 6.26 g) and additional TEA (1.1 mol eq) were added and the resulting solution heated at 50° C. for 6 h. The solvent was removed under reduced pressure, water was added to the residue (100 mL) and the aqueous phase finally extracted with EtOAc (3×40 mL). The combined organic phases were dried over $Na_2SO_4$ and evaporated under reduced pressure. The residue was recrystallized from ethyl ether to afford 2A as white solid (7.10 g, 80% yield). $^1$HNMR (DMSO, 200 MHz) δ 3.48 (s, 3H), 3.53 (m, 2H), 3.86 (t, 1H), 5.07 (t, 1H), 7.41 (m, 2H), 7.83 (m, 2H), 8.33 (bs, 1H).

Synthesis of methyl (2S)-2-[ethyl-(4-fluorophenyl)sulfonyl-amino]-3-hydroxy-propanoate 3B A solution of 2A (1 g, 3.6 mmol) in DMF (15 mL) was added with an. $K_2CO_3$ (1.4 mol eq, 0.7 g) and, after few minutes, 2-iodoethane (1.2 mol eq, 0.45 ml) was added and the mixture heated at 50° C. for 5 h. The solvent was removed under reduced pressure, water was added to the residue (80 mL) and the aqueous phase extracted with EtOAc (3×30 mL). The combined organic phases were dried using $Na_2SO_4$ and evaporated under reduced pressure to obtain 3B as a pale yellow oil (1.1 g, quantitative yield). $^1$HNMR (DMSO, 200 MHz) δ 1.13 (t, 3H, J=8), 3.29 (q, 2H), 3.41 (s, 3H), 3.79 (m, 2H), 4.53 (t, 1H), 5.14 (t, 1H), 7.41 (t, 2H, J=10), 7.86 (m, 2H).

Synthesis of 2-[ethyl-(4-fluorophenyl)sulfonyl-amino]prop-2-enoic acid 4B

A solution of 3B (1.1 g, 3.6 mmol) in dioxane (25 mL) was added with 20% NaOH aq. solution (20 mL) and the mixture heated at 80° C. for 4 h. The organic solvent was removed under reduced pressure and the aqueous phase acidified with 10% HCl and extracted with $CH_2Cl_2$ (3×30 mL). The combined organic phases were dried using $Na_2SO_4$, evaporated under reduced pressure and then the resulting residue purified by flash chromatography (100% EtOAc) to obtain 4B as white solid (0.7 g, 66% yield). $^1$HNMR (DMSO, 200 MHz) δ 1.12 (t, 3H), 3.29 (q, 2H), 5.69 (s, 1H), 6.32 (s, 1H), 7.39 (m, 2H), 7.89 (m, 2H), 12.9 (bs, 1H).

Synthesis of 2-[4-(trifluoromethyl)phenyl]pyridine-4-carbonitrile 20A

2-Chloropyridine-4-carbonitrile 19 (2.96 g, 21.35 mmol) was dissolved in 100 ml of dimethoxyethane. The solution was added with 70 ml of water, sodium bicarbonate (3 equiv., 5.38 g), [4-(trifluoromethyl)phenyl]boronic acid (1.2 equiv., 4.87 g) and the mixture was then stirred at rt for 5'. The mixture was degassed and placed under argon. A catalytic amount of tetrakispalladium was added and the mixture heated at 100° C. overnight. The solvents were evaporated off and the resulting residue dissolved with ethyl acetate and then washed with water and brine. The organic phase was dried over sodium sulfate and concentrated under vacuum. The crude was crystallized from ethyl acetate and petroleum ether to give a beige solid. (2.5 g, 47% yield).

Synthesis of [2-[4-(trifluoromethyl)phenyl]-4-pyridyl]methanamine 21A

The nitrile 20A (3 g, 12 mmol) dissolved in 50 ml of diethyl ether was added dropwise to a mixture of $LiAlH_4$ (912 mg, 2 equiv.) in diethyl ether (80 mL) and stirred at 0° C. Then, the mixture was stirred at room temperature overnight. The excess of $LiAlH_4$ was destroyed by water addition at 0° C., the solid formed was filtered, washed with $Et_2O$ and the filtrate was dried over $Na_2SO_4$ and evaporated to dryness to obtain 2.5 g of the amine as a yellow oil. The amine was used for the following step without purification.

Preparation of 2-[ethyl-(4-fluorophenyl)sulfonyl-amino]-N-[[2-[4-(trifluoromethyl)phenyl]-4-pyridyl]methyl]prop-2-enamide Example 1

Acid 4B (273.28 mg, 1 mmol) was dissolved in 10 ml of THF and at rt DEPC (1.1 equiv, 0.15 ml) and [2-[4-(trifluoromethyl)phenyl]-4-pyridyl]methanamine 21A (1.1 equiv., 277.5 mg) were added to the solution. The mixture was stirred at rt overnight then evaporated. The residue was dissolved in AcOEt (30 ml) and washed with water (1×20 ml) and brine. The organic phase was dried over sodium sulfate and concentrated under vacuum. The purification of the crude by chromatographic column (EtOAc 1/petroleum ether 1) afforded 100 mg of a white solid. Yield=19% $^1$HNMR (DMSO, 400 MHz) δ 1.09 (3H, t, J=7.2 Hz), 3.39 (2H, q, J=6.8 Hz), 4.48 (2H, d, J=6 Hz), 5.15 (1H, s), 6.14 (1H, s), 7.36 (1H, dd, J=4.8 Hz, J'=1.2 Hz), 7.47 (2H, t, J=8.8 Hz), 7.84 (4H, m), 8.01 (1H, s), 8.30 (2H, d, J=8 Hz), 8.64 (1H, dd, J=5.2 Hz, J'=0.8 Hz), 8.89 (1H, bt) [M$^{+1}$] 508.7 ($C_{24}H_{21}F_4N_3O_3S$ requires 507.50).

Example 2

2-[(4-fluorophenyl)sulfonyl-methyl-amino]-N-[[2-[4-(trifluoromethoxy)phenyl]-4-pyridyl]methyl]prop-2-enamide

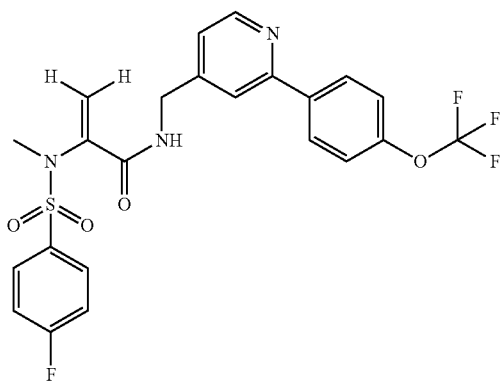 [SMILES: C=C(C(=O)NCc1ccnc(-c2ccc(OC(F)(F)F)cc2)c1)N(C)S(=O)(=O)c1ccc(F)cc1]

Synthesis of methyl (2S)-2-[(4-fluorophenyl)sulfonyl-methyl-amino]-3-hydroxy-propanoate 3A A solution of 2A (2 g, 7.2 mmol) in DMF (20 mL) was added with an. $K_2CO_3$ (1.5 mol eq, 1.49 g) and, after few minutes, iodomethane (1.2 mol eq, 0.8 ml) was added and the mixture heated at 50° C. for 12 h. The solvent was removed under reduced pressure, water was added to the residue (100 mL) and the aqueous phase extracted with EtOAc (3×40 mL). The combined organic phases were dried over $Na_2SO_4$ and evaporated under reduced pressure to obtain 3A as a pale yellow oil (2.3 g, quantitative yield). $^1$HNMR (DMSO, 200 MHz) δ 2.82 (s, 3H), 3.50 (s, 3H), 3.69 (m, 3H), 4.60 (t, 1H, J=6), 5.12 (t, 1H, J=6.1), 7.44 (m, 2H), 7.83 (m, 2H).

Synthesis of 2-[(4-fluorophenyl)sulfonyl-methyl-amino]prop-2-enoic acid 4A

A solution of 3A (2.3 g, 7.2 mmol) in dioxane (35 mL) was added with 20% NaOH aq. solution (20 mL) and the mixture was heated at 50° C. for 2 h. The organic solvent was removed under reduced pressure and the aqueous phase acidified with 10% HCl. The solid formed was collected by filtration, washed with water (2×20 mL) and dried to obtain 4A as white solid (1.05 g, 51% yield). $^1$HNMR (DMSO, 200 MHz) δ 2.92 (s, 3H), 5.57 (s, 1H), 6.09 (s, 1H), 7.50 (m, 2H), 7.85 (m, 2H), 13.01 (bs, 1H).

Synthesis of 2-[4-(trifluoromethoxy)phenyl]pyridine-4-carbonitrile 20B

A solution of 19 (2.5 g, 18 mmol) in DME (90 mL) was added 4-trifluoromethoxy phenyl boronic acid (1.1 mol eq, 4.46 g) and $NaHCO_3$ (3 mol eq, 4.66 g) suspended in water (50 mL). The mixture was degassed under vacuum, then Tetrakispalladium was added (catalytic amount) and the reaction stirred at 100° C. under inert atmosphere for 12 h. The solvent was removed under reduced pressure and water was added to the residue (100 mL). The aqueous phase was extracted with EtOAc (3×50 mL) and the combined organic layer was washed with brine (100 mL) and dried over $Na_2SO_4$. The solvent was evaporated under vacuum to obtain 20B as a pale yellow crystals (96% Yield, 4.6 g, 17.4 mmol). $^1$HNMR (DMSO, 200 MHz) δ 7.5 (dd, 2H, J=2), 7.84 (dd, 1H, J=1.8), 8.31 (d, 2H, J=9.8), 8.54 (d, 1H, J=2), 8.93 (dd, 1H, J=1.9).

Synthesis of [2-[4-(trifluoromethoxy)phenyl]-4-pyridyl]methanamine 21B

A solution of nitrile 20B (3 g, 11.3 mmol) in diethyl ether (30 mL) was added in small amounts to a mixture of $LiAlH_4$ (0.9 g, 2 mol eq) in diethyl ether (35 mL) and stirred at 0° C. After the addition was completed, the mixture was stirred at room temperature overnight. The excess of $LiAlH_4$ was destroyed at 0° C. by addition of small amount of water (30 mL), the solid formed was filtered off and the organic filtrate separated, washed with brine (50 mL) and dried over $Na_2SO_4$. The organic phase was evaporated under reduced pressure to obtain 21B as a yellow oil (3.1 g, quantitative yield). $^1$HNMR (DMSO, 200 MHz) δ 308 (s, 2H), 3.8 (bs, 2H), 7.33 (dd, 1H, J=1.8), 7.47 (dd, 2H, J=2), 7.96 (s, 1H), 8.20 (dd, 2H, J=1.8), 8.57 (dd, 1H, J=1.2).

Preparation of 2-[(4-fluorophenyl)sulfonyl-methyl-amino]-N-[[2-[4-(trifluoromethoxy)phenyl]-4-pyridyl]methyl]prop-2-enamide Example 2

A solution of acid 4A (0.26 g, 1 mmol) in THF (25 mL) was added with DEPC (0.18 mL, 1.3 mol eq) and the mixture was stirred at room temperature for about 5 minutes. Then [2-[4-(trifluoromethoxy)phenyl]-4-pyridyl]methanamine 21B (0.27 g, 1.1 mol eq) and a catalytic amount of TEA were added. The reaction mixture was then stirred at room temperature overnight. The solvent was removed under reduced pressure, the residue was suspended in EtOAc (30 mL) and washed with water (50 mL) and brine. The separated organic phase, after drying over $Na_2SO_4$, was evaporated under reduced pressure and the residue was purified by flash chromatography (8:2 EtOAc:Petroleum ether) to afford a pale yellow solid (0.1 g) after crystallization from a mixture of diethyl ether/petroleum ether. Yield=23%, $^1$HNMR (DMSO, 200 MHz) δ 2.95 (3H, s), 4.49 (d, 2H, J=6 Hz), 5.10 (s, 1H), 5.88 (s, 1H), 7.35 (dd, 1H), 7.47 (m, 4H), 7.48 (m, 2H), 7.96 (s, 1H), 8.21 (dd, 2H), 8.61 (d, 1H, J=4 Hz), 8.94 (t, 1H); $[M^{+1}]$ 509.47 ($C_{23}H_{19}F_4N_3O_4S$ requires 509.10).

Example 3

2-[(4-fluorophenyl)sulfonyl-ethyl-amino]-N-[[2-[4-(trifluoromethoxy)phenyl]-4-pyridyl]methyl]prop-2-enamide

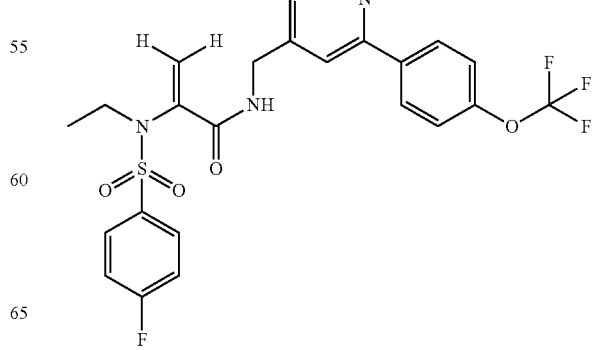

Preparation of 2-[(4-fluorophenyl)sulfonyl-ethyl-amino]-N-[[2-[4-(trifluoromethoxy)phenyl]-4-pyridyl]methyl]prop-2-enamide Example 3

A solution of acid 4B (0.25 g, 1 mmol) in THF (20 mL) was added with DEPC (0.17 mL, 1.3 mol eq) and the mixture was stirred at room temperature for about 5 minutes. Then [2-[4-(trifluoromethoxy)phenyl]-4-pyridyl]methanamine 21B (0.27 g, 1.1 mol eq) and a catalytic amount of TEA were added, then the reaction mixture was stirred at room temperature overnight. The solvent was removed under reduced pressure, the residue was suspended in EtOAc (30 mL) and washed with water (50 mL) and brine. The separated organic phase, after drying over $Na_2SO_4$, was evaporated under reduced pressure and the residue purified by flash chromatography (7:3 EtOAc:Petroleum ether) to afford a pale orange solid (0.12 g) after crystallization from a mixture of diethyl ether/petroleum ether.

Pale yellow solid. Yield=30%, $^1$HNMR (DMSO, 200 MHz) δ 1.08 (t, 3H, J=6.8 Hz), 3.40 (q, 2H), 4.48 (d, 2H, J=6), 5.15 (s, 1H), 6.14 (s, 1H), 7.29 (d, 1H), 7.43 (m, 4H), 7.86-7.88 (m, 3H), 8.21 (d, 2H), 8.58 (d, 1H), 8.85 (t, 1H); [M$^{+1}$] 523.50 ($C_{24}H_{21}F_4N_3O_4S$ requires 523.14).

Example 4

2-[(4-chlorophenyl)sulfonyl-methyl-amino]-N-[[2-[4-(trifluoromethoxy)phenyl]-4-pyridyl]methyl]prop-2-enamide

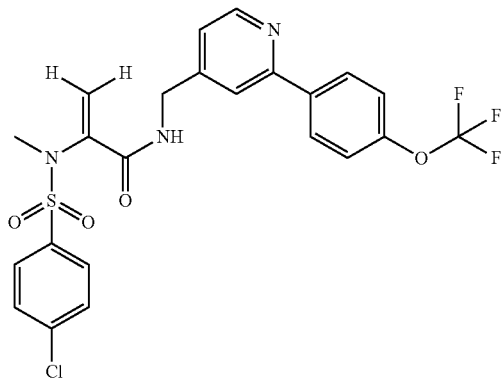 [SMILES: C=C(C(=O)NCc1ccnc(-c2ccc(OC(F)(F)F)cc2)c1)N(C)S(=O)(=O)c1ccc(Cl)cc1]

Synthesis of methyl (2S)-2-[(4-chlorophenyl)sulfonylamino]-3-hydroxy-propanoate 2C A suspension of L-serine-methyl ester hydrochloride (5 g, 32.13 mmol) in $CH_2Cl_2$ (100 mL) was added with TEA (1.1 mol eq, 4.9 mL) and the mixture was stirred at r.t. for 10 minutes. Then 4-chlorobenzensulfonyl chloride (1 mol eq, 6.81 g) and additional TEA (1.1 mol eq) were added and the solution hated at 50° C. for 5 h. The solvent was removed under reduced pressure, water was added to the residue (100 mL) and the aqueous phase extracted with EtOAc (3×40 mL). The combined organic phases were dried over $Na_2SO_4$ and evaporated to reduced pressure. The residue was recrystallized from ethyl ether to afford 2C as white solid (8.6 g, 91% yield). $^1$HNMR (DMSO, 200 MHz) δ 3.51 (s, 3H), 3.60 (m, 2H), 3.91 (t, 1H), 5.17 (t, 1H), 7.50 (d, 2H, J=8), 7.89 (d, 2H, J=7.8)), 8.35 (bs, 1H).

Synthesis of methyl (2S)-2-[(4-chlorophenyl)sulfonyl-methyl-amino]-3-hydroxy-propanoate 3C A solution of 2C (8.5 g, 28 mmol) in DMF (30 mL) was added with an. $K_2CO_3$ (1.5 mol eq, 5.99 g) and, after few minutes, iodomethane (1.2 mol eq, 3.21 mL) was added and the mixture heated at 50° C. for 12 h. The solvent was removed under reduced pressure, water was added to the residue (150 mL) and the aqueous phase extracted with EtOAc (3×60 mL). The combined organic phases were dried over $Na_2SO_4$ and evaporated under reduced pressure to afford 3C as a pale yellow oil (8.6 g, 97% yield). $^1$HNMR (DMSO, 200 MHz) δ 2.88 (s, 3H), 3.52 (s, 3H), 3.66 (m, 2H), 4.02 (q, 1H, J=6), 4.602 (t, 1H, J=6.1), 5.11 (t, 1H), 7.64 (d, 2H), 7.76 (d, 2H).

Synthesis of 2-[(4-chlorophenyl)sulfonyl-methyl-amino]prop-2-enoic acid 4C

A solution of 3C (8.5 g, 27.6 mmol) in dioxane (20 mL) was added with 20% NaOH aq. solution (30 mL) and the mixture heated at 80° C. for 5 h. The organic solvent was removed under reduced pressure and the aqueous phase acidified with 10% HCl and extracted with $CH_2Cl_2$ (3×50 mL). The combined organic phases were dried over $Na_2SO_4$ and evaporated under reduced pressure to afford 4C as a pale yellow deliquescent solid (4.3 g, 62% yield). $^1$HNMR (DMSO, 200 MHz) δ 2.91 (s, 3H), 5.58 (s, 1H), 6.09 (s, 1H), 7.72-7.60 (m, 4H), 13.05 (bs, 1H).

Preparation of 2-[(4-chlorophenyl)sulfonyl-methyl-amino]-N-[[2-[4-(trifluoromethoxy)phenyl]-4-pyridyl]methyl]prop-2-enamide Example 4

A solution of acid 4C (0.50 g, 1.8 mmol) in THF (30 mL) was added with DEPC (0.35 mL, 1.3 mol eq) and the mixture stirred at room temperature several minutes. Then [2-[4-(trifluoromethoxy)phenyl]-4-pyridyl]methanamine 21B (0.53 g, 1.1 mol eq) and a catalytic amount of TEA were added, then the reaction mixture was stirred at room temperature overnight. The solvent was removed under reduced pressure, the residue was suspended in EtOAc and washed with water and brine. The separated organic phase was dried over an. $Na_2SO_4$ and evaporated under reduced pressure. The residue was purified by flash chromatography (7:3 EtOAc:Petroleum ether) to afford a pale yellow viscous oil (0.17 g). Yield=18%, $^1$HNMR (DMSO, 200 MHz) δ 2.98 (s, 3H), 4.22 (d, 2H), 5.08 (s, 1H), 5.85 (s, 1H), 7.4 (m, 3H), 7.65 (dd, 4H, J=8), 7.95 (s, 1H), 8.2 (d, 2H), 8.58 (d, 1H), 8.95 (t, 1H); [M$^{+1}$] 525.93 ($C_{23}H_{19}ClF_3N_3O_4S$ requires 525.07).

Example 5

2-[(4-chlorophenyl)sulfonyl-ethyl-amino]-N-[[2-[4-(trifluoromethoxy)phenyl]-4-pyridyl]methyl]prop-2-enamide

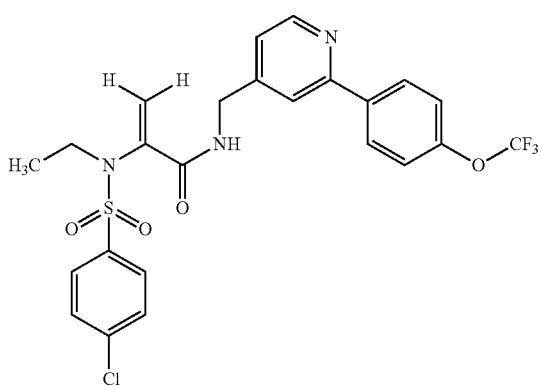 [SMILES: C=C(C(=O)NCc1ccnc(-c2ccc(OC(F)(F)F)cc2)c1)N(CC)S(=O)(=O)c1ccc(Cl)cc1]

Synthesis of ethyl (2S)-2-[(4-chlorophenyl)sulfonyl-ethyl-amino]-3-hydroxy-propanoate 3D Compound 2C (1.65 g, 5.6 mmol) dissolved in DMF (15 ml) was added with $K_2CO_3$ (1.1 equiv., 854 mg) and ethyl iodide (1.1 equiv., 0.63 ml) and the reaction was stirred at rt overnight. The reaction was diluted with ethyl acetate and washed several times with water and finally with Brine. The organic phase was dried over sodium sulfate and concentrated under vacuum. The purification of the crude residue by crystallization from ethyl ether and petroleum ether afforded 1.6 g of a semisolid. Yield=88%. $^1$HNMR (DMSO, 200 MHz) δ 1.00 (3H, d, J=6.2 Hz), 3.32 (3H, s), 3.34 (2H, m), 3.75 (2H, m), 4.42 (1H, t), 5.08 (1H, bs), 7.62 (2H, m), 7.76 (2H, m)

Synthesis of 2-[(4-chlorophenyl)sulfonyl-ethyl-amino]prop-2-enoic acid 4D

Compound 3D (1.4 g, 4.45 mmol) dissolved in THF (20 ml) and water (5 ml) was added with $LiOH.H_2O$ (3 equiv., 560 mg) and the reaction was stirred at rt 3 hours. The reaction was concentrated under vacuum. Water was added and 10% HCl till precipitation of the acid. The acid was extracted with ethyl acetate and the organic phase was washed with Brine, dried over sodium sulfate and concentrated under vacuum to give 1.3 g of a white solid. Yield=95%. $^1$HNMR (DMSO, 200 MHz) δ 1.17 (3H, t, J=7.8 Hz), 3.32 (2H, m), 3.76 (2H, m), 4.42 (1H, t), 5.08 (1H, bs), 7.61 (2H, m), 7.82 (2H, m), 12.85 (1H, bs). The intermediate acid (1.23 g, 4 mmol) dissolved in pyridine (10 ml) was added dropwise with acetyl chloride (1.4 equiv., 0.45 ml) at 0° C. and the reaction was then stirred at rt for 5 hours. The reaction was quenched by addition of 10% HCl and then extracted with ethyl acetate. The organic phase was washed 2 times with water, with brine, dried over sodium sulfate and concentrated under vacuum. The crude product was crystallized from diethyl ether and petroleum ether to give 500 mg of a beige solid. Yield=43%. $^1$HNMR (DMSO, 200 MHz) δ 1.00 (3H, t, J=7.2 Hz), 3.40 (2H, m), 5.72 (1H,$), 6.33 (1H, s), 7.72 (4H, m), 13.00 (1H, bs)

Preparation of 2-[(4-chlorophenyl)sulfonyl-ethyl-amino]-N-[[2-[4-(trifluoromethoxy)phenyl]-4-pyridyl]methyl]prop-2-enamide Example 5

Acid 4D (221.45 mg, 1 mmol) was dissolved in 10 ml of THF and at rt DEPC (1.1 equiv, 0.15 ml) and [2-[4-(trifluoromethoxy)phenyl]-4-pyridyl]methanamine 21B (1.1 equiv., 295 mg) were added to the solution. The mixture was stirred at rt overnight then evaporated. The residue was dissolved in EtOAc (30 ml) and washed with water (1×20 ml) and brine. The organic phase was dried over sodium sulfate and concentrated under vacuum. The purification of the crude by chromatographic column (3:7 EtOAc:petroleum ether) afforded 100 mg of a white solid. Yield=18.5% $^1$HNMR (DMSO, 400 MHz) δ 1.08 (3H, t), 3.40 (2H, q), 4.42 (2H, d), 5.20 (1H, s), 6.08 (1H, s), 7.23 (1H, d), 7.45 (2H, d), 7.72 (4H, dd), 7.85 (1H, s), 8.20 (2H, d), 8.60 (1H, d), 8.74 (1H, bt) [M$^{+1}$] 540.1 ($C_{24}H_{21}ClF_3N_3O_4S$ requires 539.95).

Example 6

2-(methyl(p-tolylsulfonyl)amino)-N-[[2-[4-(trifluoromethoxy)phenyl]-4-pyridyl]methyl]prop-2-enamide

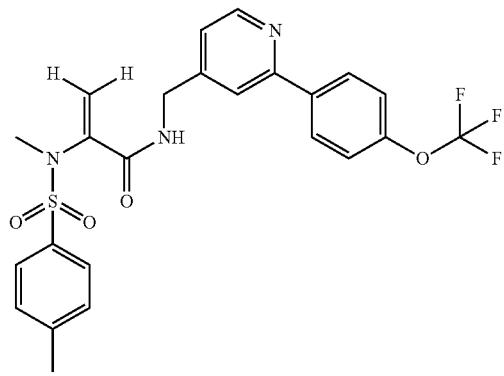 [SMILES: C=C(C(=O)NCc1ccnc(-c2ccc(OC(F)(F)F)cc2)c1)N(C)S(=O)(=O)c1ccc(C)cc1]

Synthesis of methyl (2S)-3-hydroxy-2-(p-tolylsulfonylamino)propanoate 2E

A suspension of L-serine-methyl ester hydrochloride 1 (5 g, 32.13 mmol) in $CH_2Cl_2$ (150 mL) was added with TEA (1.1 mol eq, 4.92 mL) and the mixture was stirred at r.t. for 10 minutes. Then p-tolylbenzensulfonyl chloride (1 mol eq, 6.14 g) and additional TEA (1.1 mol eq) were added and the solution was heated at 50° C. for 5 h. The solvent was removed under reduced pressure, water was added to the residue (150 mL) and the aqueous phase extracted with EtOAc (3×50 mL). The combined organic phases were dried over $Na_2SO_4$ and evaporated under reduced pressure to afford 2E as white solid (8.10 g, 90% yield).
$^1$HNMR (DMSO, 200 MHz) δ 2.37 (s, 3H), 3.44 (s, 3H), 3.50 (m, 2H), 3.81 (t, 1H), 5.04 (t, 1H, J=5.8), 7.38 (d, 2H, J=8), 7.66 (d, 2H, J=7.9), 8.15 (bd, 1H).

Synthesis of methyl (2S)-3-hydroxy-2-(methyl(p-tolylsulfonyl)amino)propanoate 3E A solution of 2E (2 g, 7.35 mmol) in DMF (15 mL) was added with an .$K_2CO_3$ (1.5 mol eq, 1.52 g) and, after few minutes, iodomethane (1.2 mol eq, 0.81 ml) was added and the mixture was heated at 50° C. overnight. The solvent was removed under reduced pressure, water was added to the residue (120 mL) and the aqueous phase was extracted with EtOAc (3×50 mL). The combined organic phases were dried over $Na_2SO_4$ and evaporated under reduced pressure to afford 3E as a pale yellow oil (2.1 g, quantitative yield). $^1$HNMR (DMSO, 200 MHz) δ 2.38 (s, 3H), 2.87 (s, 3H), 3.64 (s, 3H), 3.70 (t, 2H), 4.58 (t, 1H), 5.11 (t, 1H), 7.40 (d, 2H, J=8), 7.61 (d, 2H, J=8).

Synthesis of 2-(methyl(p-tolylsulfonyl)amino)prop-2-enoic acid 4E

A solution of 3E (1.4 g, 4.87 mmol) in dioxane (30 mL) was added with 20% NaOH aq. solution (30 mL) and the mixture was heated at 60° C. overnight. The organic solvent was removed under reduced pressure and the aqueous phase was acidified with 10% HCl and extracted with $CH_2Cl_2$ (3×50 mL). The combined organic phases were dried over $Na_2SO_4$ and evaporated under reduced pressure to afford 4E as a pale yellow solid (0.8 g, 65% yield). $^1$HNMR (DMSO, 200 MHz) δ 2.81 (s, 3H), 2.88 (s, 3H), 5.46 (s, 1H), 6.02 (s, 2H), 7.41 (d, 2H, J=7.8), 7.66 (d, 2H, H=8), 13.01 (bs, 1H).

Preparation of 2-(methyl(p-tolylsulfonyl)amino)-N-[[2-[4-(trifluoromethoxy)phenyl]-4-pyridyl]methyl]prop-2-enamide Example 6

A solution of acid 4E (0.57 g, 2.2 mmol) in THF (30 mL) was added with DEPC (0.43 mL, 1.3 mol eq) and the mixture was stirred at room temperature for about 5 minutes. Then [2-[4-(trifluoromethoxy)phenyl]-4-pyridyl]methanamine 21B (0.66 g, 1.1 mol eq) and a catalytic amount of TEA were added, then the reaction mixture was stirred at room temperature overnight. The solvent was removed under reduced pressure, the residue was suspended in EtOAc and washed with water and brine. The separated organic phase was evaporated under reduced pressure and the residue was purified by flash chromatography (7:3 EtOAc:Petroleum ether) to afford a pale yellow solid (0.27 g) after crystallization from a mixture of diethyl ether/petroleum ether. Yield=25%, $^1$HNMR (DMSO, 200 MHz) δ 2.48 (s, 3H), 2.86 (s, 3H), 4.49 (d, 2H, J=6), 5.00 (s, 1H), 5.85 (s, 1H), 7.35 (d, 1H), 7.42 (m, 4H), 7.71 (d, 2H, J=8.2), 7.97 (s, 1H), 8.21 (dd, 2H, J=2.2), 8.61 (d, 1H, J=4), 8.90 (t, 1H); [M$^{+1}$] 505.51 ($C_{24}H_{22}F_3N_3O_4S$ requires 505.12).

Example 7

2-[(5-chloro-2-thienyl)sulfonyl-ethyl-amino]-N-[[2-[4-(trifluoromethoxy)phenyl]-4-pyridyl]methyl]prop-2-enamide

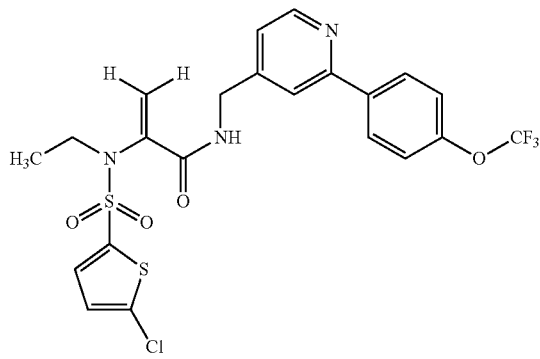 [SMILES: C=C(C(=O)NCc1ccnc(-c2ccc(OC(F)(F)F)cc2)c1)N(CC)S(=O)(=O)c1ccc(Cl)s1]

Synthesis of methyl (2S)-2-[(5-chloro-2-thienyl)sulfonylamino]-3-hydroxy-propanoate 5

L-Serine methyl ester hydrochloride (5 g, 32.13 mmol) dissolved in methylene chloride (200 ml) was added with TEA (2 equiv., 8.95 ml) and in one portion 5-chlorothiophene-2-sulfonyl chloride (1.0 equiv., 6.97 g). The reaction was refluxed for 4 hours. The solvent was evaporated and the crude was dissolved in AcOEt (100 ml) and washed with water (1×80 ml) and brine. The organic phase was dried over sodium sulfate and concentrated under vacuum. The purification of the crude residue by crystallization from diethyl ether and petroleum ether afforded 10 g of the white product. Yield=93% $^1$HNMR (DMSO, 200 MHz) δ 2.81 (2H, q, J=7.2 Hz), 3.52 (3H, s), 3.92 (1H, t), 5.06 (1H, bs), 7.24 (1H, dd, J=4.2 Hz), 7.45 (1H, dd, J=4 Hz), 8.92 (1H, bs)

Synthesis of methyl (2S)-2-[(5-chloro-2-thienyl)sulfonyl-ethyl-amino]-3-hydroxy-propanoate 6

Compound 5 (10 g, 30 mmol) dissolved in DMF (100 ml) was added with $K_2CO_3$ (1.1 equiv., 4.56 g) and ethyl iodide (1.1 equiv., 3.16 ml) and the reaction was stirred at rt overnight. The reaction was diluted with ethyl acetate and washed several times with water and finally with Brine. The organic phase was dried over sodium sulfate and concentrated under vacuum. The purification of the crude residue by crystallization from ethyl ether and petroleum ether afforded 10 g of a semisolid. Yield=93%. $^1$HNMR (DMSO, 200 MHz) δ 1.17 (3H, t, J=7 Hz), 3.40 (2H, q), 3.54 (3H, s), 3.80 (2H, t, J=5.8 Hz), 4.50 (1H, t), 5.00 (1H, bt), 7.28 (1H, dd, J=4 Hz, J'=1 Hz), 7.57 (1H, dd, J=4.2 Hz, J'=1 Hz).

Synthesis of 2-[(5-chloro-2-thienyl)sulfonyl-ethyl-amino]prop-2-enoic acid 7

Compound 6 (10 g, 28 mmol) dissolved in THF (100 ml) and water (50 ml) was added with $LiOH.H_2O$ (3 equiv., 3.52 g) and the reaction was stirred at rt 3 hours. The reaction was concentrated under vacuum. Water was added and 10% HCl till precipitation of the acid. The acid was extracted with ethyl acetate and the organic phase was washed with Brine, dried over sodium sulfate and concentrated under vacuum to give 8 g of a white solid. Yield=81.5%. $^1$HNMR (DMSO, 200 MHz) δ 1.17 (3H, t, J=5.6 Hz), 3.35 (2H, q), 4.04 (2H, q, J=7 Hz), 4.39 (1H, t), 5.96 (1H, bs), 7.26 (1H, dd, J=4 Hz, J'=0.6 Hz), 7.55 (1H, dd, J=3.8 Hz, J'=0.4 Hz), 12.98 (1H, bs). The intermediate acid (2.45 g, 7 mmol) dissolved in pyridine (10 ml) was added dropwise with acetyl chloride (1.4 equiv., 0.8 ml) at 0° C. and the reaction was then stirred at rt for 5 hours The reaction was quenched by addition of 10% HCl and then extracted with ethyl acetate. The organic phase was washed 2 times with water, with brine, dried over sodium sulfate and concentrated under vacuum. The crude product was crystallized from diethyl ether and petroleum ether to give 1 g of a beige solid. Yield=43%. $^1$HNMR (DMSO, 200 MHz) δ 1.04 (3H, t, J=7.4 Hz), 3.44 (2H, q), 5.82 (1H, s), 6.39 (1H, s), 7.31 (1H, d, J=4.2 Hz), 7.55 (1H, d, J=4 Hz), 13.05 (1H, bs)

Preparation of 2-[(5-chloro-2-thienyl)sulfonyl-ethyl-amino]N-[[2-[4-(trifluoromethoxy)phenyl]-4-pyridyl]methyl]prop-2-enamide Example 7

Acid 7 (665 mg, 2 mmol) was dissolved in 10 ml of THF and at rt DEPC (1.1 equiv, 0.3 ml) and [2-[4-(trifluoromethoxy)phenyl]-4-pyridyl]methanamine 21B (1.1 equiv., 590 mg) were added to the solution. The mixture was stirred at rt overnight then evaporated. The residue was dissolved in AcOEt (30 ml) and washed with water (1×20 ml) and brine. The organic phase was dried over sodium sulfate and concentrated under vacuum. The purification of the crude by chromatographic column (3:7 EtOAc:petroleum ether) afforded 200 mg of a pale yellow solid. Yield=18.3% $^1$HNMR (DMSO, 200 MHz) δ 1.12 (3H, t, J=7 Hz), 3.47 (2H, q, J=7.2 Hz), 4.48 (2H, d, J=6 Hz), 5.41 (1H, s), 6.25 (1H, s), 7.28 (2H, m), 7.48 (2H, d, J=7.8 Hz), 7.60 (1H, d, J=4.2 Hz), 7.90 (1H, bs), 8.19 (2H, dd, J=6.8 Hz), 8.61 (1H, d, J=5 Hz), 8.89 (1H, bt) [M$^{+1}$] 546.1 ($C_{22}H_{19}ClF_3N_3O_4S_2$ requires 545.98).

Example 8

2-[ethyl-(4-fluorophenyl)sulfonyl-amino]-N-[[3-[4-(trifluoromethyl)phenyl]phenyl]methyl]prop-2-enamide

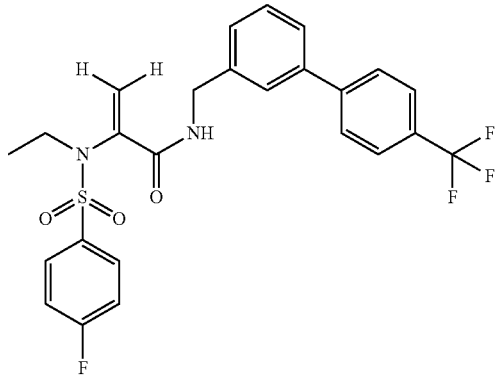 [SMILES: C=C(C(=O)NCc1cccc(-c2ccc(C(F)(F)F)cc2)c1)N(CC)S(=O)(=O)c1ccc(F)cc1]

Synthesis of [3-[4-(trifluoromethyl)phenyl]phenyl]methanamine 23A

A suspension of 3-bromobenzylamine hydrochloride 22 (1 g, 4.49 mmol) in DME (50 mL) was added with 4-trifluoromethyl phenyl boronic acid (1.2 mol eq, 1.0 g) and NaHCO$_3$ (3 mol eq, 1.13 g) suspended in water (30 mL). The mixture was degassed under vacuum, then Tetrakispalladium was added (catalytic amount) and the reaction was stirred at 100° C. under inert atmosphere for 12 h. The solvent was removed under reduced pressure and water was added to the residue (80 mL). The aqueous phase was extracted with EtOAc (3×40 mL) and the combined organic layer was washed with brine (50 mL) and dried over Na$_2$SO$_4$. The solvent was evaporated under vacuum to afford 23A as a pale brown oil (1.5 g, quantitative yield).

$^1$HNMR (DMSO, 400 MHz) δ 1.86 (bs, 2H), 3.79 (s, 2H), 7.39 (d, 1H), 7.44 (t, 1H), 7.56 (d, 1H), 7.71 (s, 1H), 7.82 (d, 2H), 7.90 (d, 2H).

Preparation of 2-[ethyl-(4-fluorophenyl)sulfonyl-amino]-N-[[3-[4-(trifluoromethyl)phenyl]phenyl]methyl]prop-2-enamide Example 8

A solution of acid 4B (0.30 g, 1.1 mmol) in THF (20 mL) was added with DEPC (0.22 mL, 1.3 mol eq) and the mixture stirred at room temperature for 10 minutes. Then [3-[4-(trifluoromethoxy)phenyl]phenyl]methanamine 23A (0.303 g, 1.1 mol eq) and a catalytic amount of TEA were added, then the reaction mixture was stirred at room temperature overnight. The solvent was removed under reduced pressure, the residue was suspended in EtOAc (45 mL) and washed with water (50 mL) and brine. The separated organic phase was dried over an. Na$_2$SO$_4$ and evaporated under reduced pressure. The residue was purified by flash chromatography (3:7 EtOAc:Petroleum ether) to afford a white solid (0.11 g). Yield=22%, $^1$HNMR (DMSO, 200 MHz) δ. 1.089 (t, 3H), 3.38 (m, 2H), 4.46 (d, 2H, J=4.2), 5.16 (s, 1H), 6.09 (s, 1H), 7.35 (d, 1H), 7.43 (m, 3H), 7.60 (d, 1H), 7.69 (s, 1H), 7.78 (d, 2H), 7.88 (m, 4H), 8.79 (bs, 1H). [M$^{+1}$] 506.51 (C$_{25}$H$_{22}$F$_4$N$_2$O$_3$S requires 506.12).

Example 9

2-[(4-chlorophenyl)sulfonyl-methyl-amino]-N-[[3-[4-(trifluoromethyl)phenyl]phenyl]methyl]prop-2-enamide

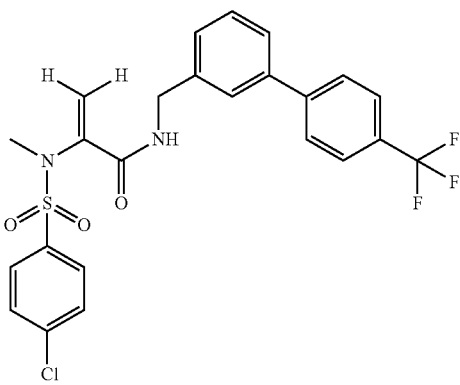 [SMILES: C=C(C(=O)NCc1cccc(-c2ccc(C(F)(F)F)cc2)c1)N(C)S(=O)(=O)c1ccc(Cl)cc1]

Preparation of 2-[(4-chlorophenyl)sulfonyl-methyl-amino]-N-[[3-[4-(trifluoromethyl)phenyl]phenyl]methyl]prop-2-enamide Example 9

Acid 4C (827 mg, 3 mmol) was dissolved in 10 ml of THF and at rt DEPC (1.1 equiv, 0.5 ml) and [3-[4-(trifluoromethyl)phenyl]phenyl]methanamine 23A (1.1 equiv., 835 mg) were added to the solution. The mixture was stirred at rt overnight then evaporated. The residue was dissolved in AcOEt (30 ml) and washed with water (1×20 ml) and brine. The organic phase was dried over sodium sulfate and concentrated under vacuum. The purification of the crude by chromatographic column (3:7 EtOAc:petroleum ether) afforded 200 mg of a beige solid. Yield=13% $^1$HNMR (DMSO, 200 MHz) δ 2.93 (3H, s), 4.44 (2H, d, J=5.8 Hz), 5.13 (1H, s), 5.85 (1H, s), 7.76 (12H, m), 8.82 (1H, bt) [M$^{+1}$] 509.1 (C$_{24}$H$_{20}$ClF$_3$N$_2$O$_3$S requires 508.94).

Example 10

2-[(4-chlorophenyl)sulfonyl-ethyl-amino]-N-[[3-[4-(trifluoromethyl)phenyl]phenyl]methyl]prop-2-enamide

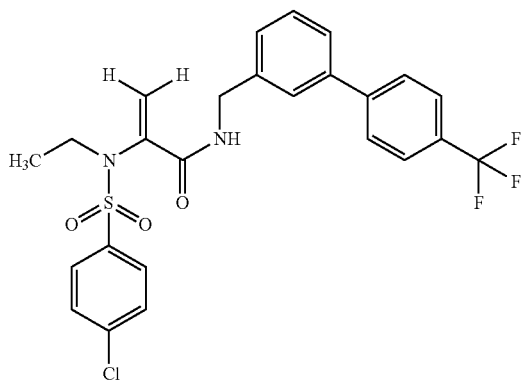 [SMILES: C=C(C(=O)NCc1cccc(-c2ccc(C(F)(F)F)cc2)c1)N(CC)S(=O)(=O)c1ccc(Cl)cc1]

Preparation of 2-[(4-chlorophenyl)sulfonyl-ethyl-amino]-N-[[3-[4-(trifluoromethyl)phenyl]phenyl]methyl]prop-2-enamide Example 10

Acid 4D (869 mg, 3 mmol) was dissolved in 10 ml of THF and at rt DEPC (1.1 equiv, 0.5 ml) and [3-[4-(trifluoromethyl)phenyl]phenyl]methanamine 23A (1.1 equiv., 835 mg) were added to the solution. The mixture was stirred at rt overnight then evaporated. The residue was dissolved in AcOEt (30 ml) and washed with water (1×20 ml) and brine. The organic phase was dried over sodium sulfate and concentrated under vacuum. The purification of the crude by chromatographic column (3:7 EtOAc:petroleum ether) afforded 200 mg of a beige solid. Yield=13% $^1$HNMR (DMSO, 200 MHz) δ 1.06 (3H, t, J=7 Hz), 3.39 (2H, q, J=7 Hz), 4.44 (2H, d, J=6 Hz), 5.20 (1H, s), 6.10 (1H, s), 7.40 (1H, d), 7.46 (1H, t, J=7.6 Hz), 7.76 (10H, m), 8.79 (1H, bt) [M$^{+1}$] 523.1 ($C_{25}H_{22}ClF_3N_2O_3S$ requires 522.97).

Example 11

2-[ethyl-(4-fluorophenyl)sulfonyl-amino]-N-[[3-[4-(trifluoromethoxy)phenyl]phenyl]methyl]prop-2-enamide

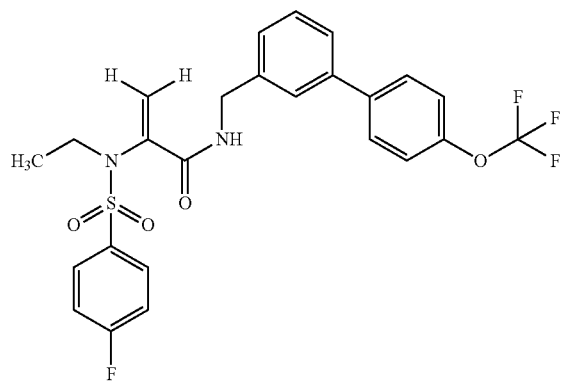 [SMILES: C=C(C(=O)NCc1cccc(-c2ccc(OC(F)(F)F)cc2)c1)N(CC)S(=O)(=O)c1ccc(F)cc1]

Synthesis of [3-[4-(trifluoromethyl)phenyl]phenyl]methanamine 23B

A suspension of 3-bromobenzylamine hydrochloride 22 (1 g, 4.49 mmol) in DME (50 mL) was added with 4-trifluoromethoxy phenyl boronic acid (1.2 mol eq, 1.11 g) and NaHCO$_3$ (3 mol eq, 1.13 g) suspended in water (30 mL). The mixture was degassed under vacuum, then Tetrakispalladium was added (catalytic amount) and the reaction was stirred at 100° C. under inert atmosphere for 12 h. The solvent was removed under reduced pressure and water was added to the residue (80 mL). The aqueous phase was extracted with EtOAc (3×40 mL) and the combined organic layer was washed with brine (50 mL) and dried over Na$_2$SO$_4$. The solvent was evaporated under vacuum to afford 23B as a pale brown oil (1.5 g, quantitative yield).
$^1$HNMR (DMSO, 200 MHz) δ 3.80 (bs, 2H), 3.77 (s, 2H), 7.42 (m, 2H), 7.52 (d, 1H), 7.68 (s, 1H), 7.79 (d, 2H), 7.89 (d, 2H)

Preparation of 2-[ethyl-(4-fluorophenyl)sulfonyl-amino]-N-[[3-[4-(trifluoromethoxy)phenyl]phenyl]methyl]prop-2-enamide Example 11

A solution of acid 4B (0.35 g, 1.28 mmol) in THF (25 mL) was added with DEPC (0.25 mL, 1.3 mol eq) and the mixture was stirred at room temperature for 10'. Then [3-[4-(trifluoromethoxy)phenyl]phenyl]methanamine 23B (0.376 g, 1.1 mol eq) and a catalytic amount of TEA were added, then the reaction mixture was stirred at room temperature overnight. The solvent was removed under reduced pressure, water (40 mL) was added to the residue that is extracted with EtOAc (3×25 mL) and washed with brine (1×40 mL). The separated organic phase was anydrified over Na$_2$SO$_4$, evaporated to dryness and the residue was purified by flash chromatography (1:1 EtOAc:Petroleum ether) to afford a white solid (0.15 g) after recrystallization from ethyl ether. Yield=24%, $^1$HNMR (DMSO, 200 MHz) δ 1.08 (t, 3H, J=8), 3.37 (q, 2H, J=7.5), 4.44 (d, 2H, J06.1), 5.16 (s, 1H), 6.09 (s, 1H), 7.32 (d, 1H), 7.46 (m, 5H), 7.53 (d, 1H), 7.62 (s, 1H), 7.76 (dd, 2H), 7.86 (m, 2H), 8.78 (t, 1H); [M$^{+1}$] 522.51 ($C_{25}H_{22}F_4N_2O_4S$ requires 522.12).

Example 12

2-[(5-chloro-2-thienyl)sulfonyl-ethyl-amino]-N-[[2-[4-(trifluoromethyl)phenyl]-4-pyridyl]methyl]prop-2-enamide

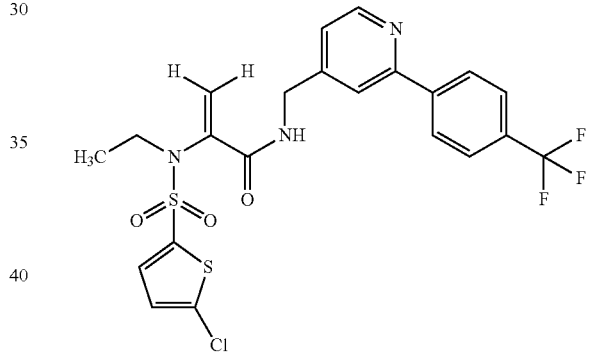

Preparation of 2-[(5-chloro-2-thienyl)sulfonyl-ethyl-amino]-N-[[2-[4-(trifluoromethyl)phenyl]-4-pyridyl]methyl]prop-2-enamide Example 12

Acid 7 (295.76 mg, 1 mmol) was dissolved in 10 ml of THF and at rt DEPC (1.1 equiv, 0.15 ml) and [2-[4-(trifluoromethyl)phenyl]-4-pyridyl]methanamine 21A (1.1 equiv., 277.5 mg) were added to the solution. The mixture was stirred at rt overnight then evaporated. The residue was dissolved in AcOEt (30 ml) and washed with water (1×20 ml) and brine. The organic phase was dried over sodium sulfate and concentrated under vacuum. The purification of the crude by chromatographic column (1:1 EtOAc:petroleum ether) afforded 100 mg of a beige solid. Yield=18.8% $^1$HNMR (DMSO, 200 MHz) δ 1.12 (3H, t, J=7 Hz), 3.47 (2H, q), 4.48 (2H, d, J=6.4 Hz), 5.41 (1H, s), 6.25 (1H, s), 7.34 (2H, m), 7.59 (1H, d, J=4 Hz), 7.84 (2H, d, J=8 Hz), 7.98 (1H, bs), 8.28 (2H, d, J=8 Hz), 8.63 (1H, d, J=5 Hz), 8.91 (1H, bt) [M$^{+1}$] 530.1 ($C_{22}H_{19}ClF_3N_3O_3S_2$ requires 529.98).

Example 13

2-[(4-chlorophenyl)sulfonyl-methyl-amino]-N-[[2-pyrrolidin-1-yl-6-[4-(trifluoromethyl)phenyl]-4-pyridyl]methyl]prop-2-enamide

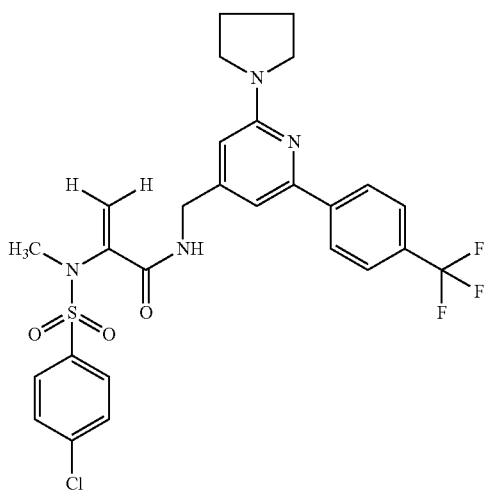 [SMILES: C=C(C(=O)NCc1cc(-c2ccc(C(F)(F)F)cc2)nc(N2CCCC2)c1)N(C)S(=O)(=O)c1ccc(Cl)cc1]

Synthesis of 2-chloro-6-pyrrolidin-1-yl-pyridine-4-carbonitrile 25A

A solution of 2,6-dichloropyridine-4-carbonitrile 24 (4 g, 23.5 mmol) in abs. EtOH (10 mL) was added with pyrrolidine (1.15 mL, 1 mol eq) and the mixture was heated at 70° C. for 6 h. The solvent was removed under reduced pressure, water was added to the residue and the aqueous phase was extracted with EtOAc (3×40 mL). The combined organic phase was washed with brine (1×60 mL), dried over $Na_2SO_4$ and evaporated to afford 25A as a pale yellow deliquescent solid (4.2 g, 20 mmol, 87% Yield). $^1$HNMR (DMSO, 400 MHz) δ 2.00 (m, 4H), 3.42 (m, 4H), 6.39 (s, 1H), 6.61 (s, 1H).

Synthesis of 2-pyrrolidin-1-yl-6-[4-(trifluoromethyl)phenyl]pyridine-4-carbonitrile 26A (Bertelot et al., PCT, WO2010/141805 A1)

The nitrile 25A (2.1 g, 10.3 mmol), 4-trifluoromethylphenylboronic acid (2.15 g, 1.1 mol eq), palladium acetate (45 mg, 0.02 mol eq), cesium carbonate (6.5 g, 2 mol eq), and XPhos (190 mg, 0.04 mol eq) were mixed, placed under a nitrogen atmosphere and dioxane (10 mL) was added. The mixture was heated at 100° C. overnight. After cooling, the mixture was filtered through a celite pad, washed with dioxane (2×20 mL) and concentrated under reduced pressure. The residue was purified by flash chromatography (9.5:0.5 petroleum ether:EtOAc) to afford 26A as a pale yellow semi-solid (2.8 g, 85% Yield). $^1$HNMR (DMSO, 200 MHz) δ 1.93 (m, 4H), 3.45 (m, 4H), 6.91 (s, 1H), 7.55 (s, 1H), 7.82 (d, 2H, J=8), 8.26 (d, 2H, J=8.1).

Synthesis of [2-pyrrolidin-1-yl-6-[4-(trifluoromethyl)phenyl]-4-pyridyl]methanamine 27A A solution of nitrile 26A (2.8 g, 8.8 mmol) in diethyl ether (30 mL) was added in small amounts to a mixture of $LiAlH_4$ (0.67 g, 2 mol eq) in diethyl ether (30 mL) stirred at 0° C. After the addition was completed, the mixture was stirred at room temperature overnight. The excess of $LiAlH_4$ was destroyed at 0° C. by addition of small amount of water (30 mL), the solid formed was filtered off and the organic filtrate was separated, washed with brine (50 mL) and dried over $Na_2SO_4$. The organic phase was evaporated under reduced pressure to afford 27A as a pale yellow oil (2.8 g, 87% yield). $^1$HNMR (DMSO, 200 MHz) δ 1.91 (m, 4H), 2.20 (bs, 2H), 3.37 (m, 4H), 3.70 (s, 2H), 6.48 (s, 1H), 7.20 (s, 1H), 7.78 (d, 2H, J=8), 8.23 (d, 2H, J=8).

Preparation of 2-[(4-chlorophenyl)sulfonyl-methyl-amino]-N-[[2-pyrrolidin-1-yl-6-[4-(trifluoromethyl)phenyl]-4-pyridyl]methyl]prop-2-enamide
Example 13

A solution of acid 4C (0.40 g, 1.45 mmol) in THF (20 mL) was added with DEPC (0.28 mL, 1.3 mol eq) and the mixture was stirred at room temperature several minutes. Then [2-pyrrolidin-1-yl-6-[4-(trifluoromethyl)phenyl]-4-pyridyl]methanamine 27A (0.51 g, 1.1 mol eq) and a catalytic amount of TEA were added, then the reaction mixture was stirred at room temperature overnight. The solvent was removed under reduced pressure, water was added to the residue that is extracted with EtOAc (3×25 mL) and washed with brine (1×40 mL). The separated organic phase was dried over $Na_2SO_4$, evaporated to dryness and the residue was purified by flash chromatography (1:1 EtOAc:Petroleum ether) to afford a white solid (0.18 g) after crystallization from ethyl ether. Yield=22%, $^1$HNMR (DMSO, 200 MHz) δ 1.95 (m, 4H), 2.95 (s, 3H), 3.46 (m, 4H), 4.36 (d, 2H), 5.12 (s, 1H), 5.86 (s, 1H), 6.52 (s, 1H), 7.22 (s, 1H), 7.73 (d, 2H, JO 7.9), 7.82-7.79 (m, 5H), 8.26 (d, 2H, J=7.8), 8.85 (t, 1H); [M$^{+1}$] 579.03 ($C_{27}H_{26}ClF_3N_4O_3S$ requires 578.13).

Example 14

2-[(4-chlorophenyl)sulfonyl-ethyl-amino]-N-[[2-pyrrolidin-1-yl-6-[4-(trifluoromethyl)phenyl]-4-pyridyl]methyl]prop-2-enamide

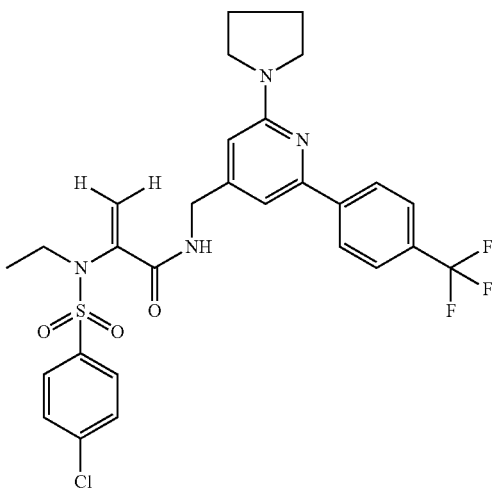 [SMILES: C=C(C(=O)NCc1cc(-c2ccc(C(F)(F)F)cc2)nc(N2CCCC2)c1)N(CC)S(=O)(=O)c1ccc(Cl)cc1]

Preparation of 2-[(4-chlorophenyl)sulfonyl-ethyl-amino]-N-[[2-pyrrolidin-1-yl-6-[4-(trifluoromethyl)phenyl]-4-pyridyl]methyl]prop-2-enamide
Example 14

Acid 4D (289.74 mg, 1 mmol) was dissolved in 10 ml of THF and at rt DEPC (1.1 equiv, 0.15 ml) and [2-pyrrolidin-1-yl-6-[4-(trifluoromethyl)phenyl]-4-pyridyl]methanamine 27A (1.1 equiv., 353.47 mg) were added to the solution. The mixture was stirred at rt overnight then evaporated. The residue was dissolved in AcOEt (30 ml) and washed with water (1×20 ml) and brine. The organic phase was dried over sodium sulfate and concentrated under vacuum. The purification of the crude by chromatographic column (3:7 EtOAc:petroleum ether) afforded 140 mg of a pale yellow solid. Yield=23.6% $^1$HNMR (DMSO, 200 MHz) δ 1.09 (3H, t), 1.91 (4H, m), 3.38 (6H, m), 4.40 (2H, d), 5.17 (1H, s), 6.11 (1H, d), 6.34 (1H, s), 7.19 (1H, s), 7.78 (6H, m), 8.28 (2H, d), 8.80 (1H, bt) [M$^{+1}$] 593.9 ($C_{28}H_{28}ClF_3N_4O_3S$ requires 593.06).

Example 15

2-[(5-chloro-2-thienyl)sulfonyl-ethyl-amino]-N-[[2-pyrrolidin-1-yl-6-[4-(trifluoromethyl)phenyl]-4-pyridyl]methyl]prop-2-enamide

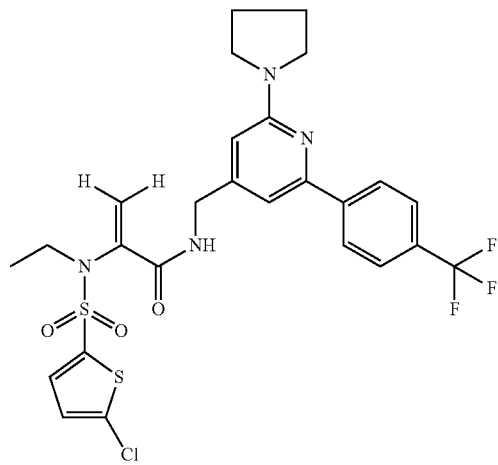 [SMILES: C=C(C(=O)NCc1cc(-c2ccc(C(F)(F)F)cc2)nc(N2CCCC2)c1)N(CC)S(=O)(=O)c1ccc(Cl)s1]

Preparation of 2-[(5-chloro-2-thienyl)sulfonyl-ethyl-amino]-N-[[2-pyrrolidin-1-yl-6-[4-(trifluoromethyl)phenyl]-4-pyridyl]methyl]prop-2-enamide
Example 15

Acid 7 (295.76 mg, 1 mmol) was dissolved in 10 ml of THF and at rt DEPC (1.1 equiv, 0.15 ml) and [2-pyrrolidin-1-yl-6-[4-(trifluoromethyl)phenyl]-4-pyridyl]methanamine 27A (1.1 equiv., 353.47 mg) were added to the solution. The mixture was stirred at rt overnight then evaporated. The residue was dissolved in AcOEt (30 ml) and washed with water (1×20 ml) and brine. The organic phase was dried over sodium sulfate and concentrated under vacuum. The purification of the crude by chromatographic column (3:7 EtOAc:petroleum ether) afforded 150 mg of a pale yellow solid. Yield=25% $^1$HNMR (DMSO, 200 MHz) δ 1.07 (3H, t), 1.94 (4H, m), 3.41 (6H, m), 4.37 (2H, d), 5.39 (1H, s), 6.21 (1H, s), 6.31 (1H, s), 7.20 (1H, s), 7.34 (1H, d, J=4.2 Hz), 7.57 (1H, d, J=4 Hz), 7.91 (2H, d), 8.48 (2H, d), 8.75 (1H, bt) [M$^{+1}$] 599.9 ($C_{26}H_{26}ClF_3N_4O_3S_2$ requires 599.09).

Example 16

2-[(4-chlorophenyl)sulfonyl-methyl-amino]-N-[[2-morpholino-6-[4-(trifluoromethoxy)phenyl]-4-pyridyl]methyl]prop-2-enamide

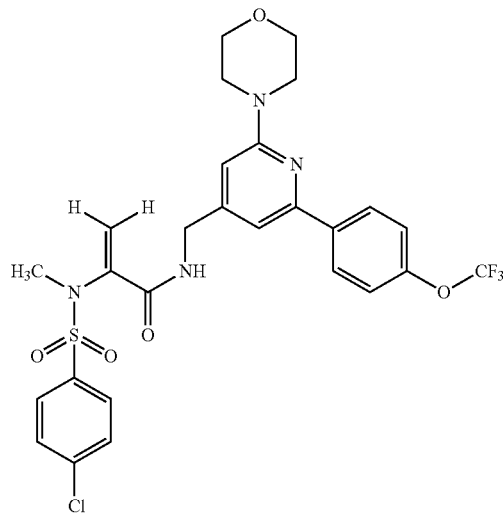 [SMILES: C=C(C(=O)NCc1cc(-c2ccc(OC(F)(F)F)cc2)nc(N2CCOCC2)c1)N(C)S(=O)(=O)c1ccc(Cl)cc1]

Synthesis of 2-chloro-6-morpholino-pyridine-4-carbonitrile 25B 2,6-dichloropyridine-4-carbonitrile 24 (4 gr, 23.13 mmol) was dissolved in 100 ml of ethanol. To the solution were added TEA (1 equiv., 3.22 ml), morpholine (1 equiv., 2 ml) and the mixture was stirred at 70° C. for 4 hours. (TLC AcOEt 3/petroleum ether 7). The solvent was evaporated and the residue was dissolved with ethyl acetate, washed with water and brine. The organic phase was dried over sodium sulfate and concentrated under vacuum. The crude was crystallized from ethyl acetate and petroleum ether to give a beige solid. (4.6 g, 89% yield) $^1$HNMR (DMSO, 400 MHz) δ 3.58 (4H, m), 3.64 (4H, m), 7.10 (1H, s), 7.32 (1H, s)

Synthesis of 2-morpholino-6-[4-(trifluoromethoxy)phenyl]pyridine-4-carbonitrile 26D The carbonitrile 25B (2.3 g, 10.28 mmol) was dissolved in 80 ml of dimethoxyethane. To the solution were added 40 ml of water, sodium bicarbonate (3 equiv., 2.6 g), [4-(trifluoromethoxy)phenyl]boronic acid (1.2 equiv., 2.54 g) and the mixture was stirred at rt for 5'. The mixture was degassed and put under argon. A catalytic amount of tetrakispalladium was added and the mixture was heated at 100° C. overnight. The solvents were evaporated off and the residue was dissolved with ethyl acetate, washed with water and brine. The organic phase was dried over sodium sulfate and concentrated under vacuum. The crude was crystallized from ethyl acetate and petroleum ether to give a beige solid. (2.0 g, 55.5% yield) $^1$HNMR (DMSO, 400 MHz) δ 3.61 (4H, m), 3.72 (4H, m), 7.20 (1H, s), 7.79 (1H, s), 7.82 (2H, d, J=8 Hz), 8.35 (2H, d, J=8 Hz)

Synthesis of [2-morpholino-6-[4-(trifluoromethoxy)phenyl]-4-pyridyl]methanamine 27D The nitrile 26D (2 g, 5.7 mmol) dissolved in 50 ml of diethyl ether was added dropwise to a mixture of LiAlH$_4$ (434 mg, 2 equiv.) in diethyl ether (60 mL) stirred at 0° C. Then the mixture was stirred at room temperature overnight. The excess of LiAlH$_4$ was destroyed by water addition at 0° C., the solid formed was filtered, washed with Et$_2$O and the filtrate was dried over Na$_2$SO$_4$ and evaporated to dryness to obtain 1.3 g of the amine 27D as a yellow oil. Yield=65% $^1$HNMR (DMSO, 400 MHz) δ 3.30 (2H, bs), 3.51 (4H, m), 3.76 (6H, m), 6.80 (1H, s), 7.29 (1H, s), 7.42 (2H, d, J=8 Hz), 8.18 (2H, dd)

Preparation of 2-[(4-chlorophenyl)sulfonyl-methyl-amino]-N-[[2-morpholino-6-[4-(trifluoromethoxy)phenyl]-4-pyridyl]methyl]prop-2-enamide
Example 16

A solution of acid 4C (0.40 g, 1.45 mmol) in THF (25 mL) was added with DEPC (0.28 mL, 1.3 mol eq) and the mixture was stirred at room temperature for about 5 minutes. Then [2-morpholino-6-[4-(trifluoromethoxy)phenyl]-4-pyridyl]methanamine 27D (0.56 g, 1.1 mol eq) and a catalytic amount of TEA were added, then the reaction mixture was stirred at room temperature overnight. The solvent was removed under reduced pressure, the residue was suspended in EtOAc and washed with water and brine. After drying over Na$_2$SO$_4$, the separated organic phase was evaporated under reduced pressure and the residue was purified by flash chromatography (7:3 EtOAc:Petroleum ether) to afford a pale yellow solid (0.24 g) after crystallization from a mixture of diethyl ether/petroleum ether. Yield=36%, $^1$HNMR (DMSO, 200 MHz) δ 2.95 (s, 3H), 3.55 (m, 4H), 3.70 (m, 4H), 4.40 (d, 2H, J=6), 5.12 (s, 1H), 5.87 (s, 1H), 6.82 (s, 1H), 7.29 (s, 1H), 7.43 (d, 2H, J=8.2), 7.83-7.74 (m, 4H), 8.17 (d, 2H, J=8), 8.86 (t, 1H); [M$^{+1}$] 611.03 (C$_{27}$H$_{26}$ClF$_3$N$_4$O$_5$S requires 610.13).

Example 17

2-[(4-chlorophenyl)sulfonyl-ethyl-amino]-N-[[2-morpholino-6-[4-(trifluoromethoxy)phenyl]-4-pyridyl]methyl]prop-2-enamide

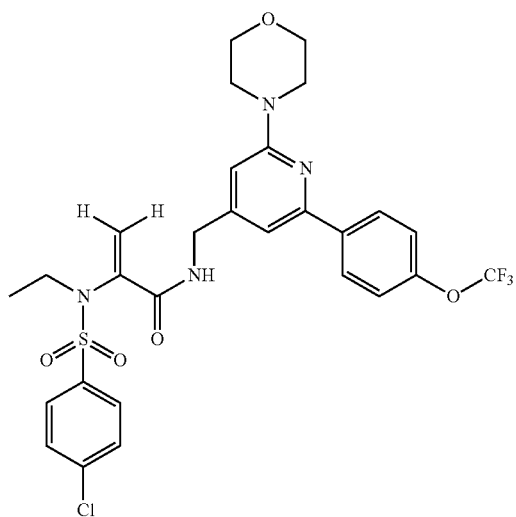 [SMILES: C=C(C(=O)NCc1cc(-c2ccc(OC(F)(F)F)cc2)nc(N2CCOCC2)c1)N(CC)S(=O)(=O)c1ccc(Cl)cc1]

Preparation of 2-[(4-chlorophenyl)sulfonyl-ethyl-amino]-N-[[2-morpholino-6-[4-(trifluoromethoxy)phenyl]-4-pyridyl]methyl]prop-2-enamide
Example 17

Acid 4D (289.74 mg, 1 mmol) was dissolved in 10 ml of THF and at rt DEPC (1.1 equiv, 0.15 ml) and [2-morpholino-6-[4-(trifluoromethoxy)phenyl]-4-pyridyl]methanamine 27D (1.1 equiv., 388 mg) were added to the solution. The mixture was stirred at rt overnight then evaporated. The residue was dissolved in AcOEt (30 ml) and washed with water (1×20 ml) and brine. The organic phase was dried over sodium sulfate and concentrated under vacuum. The purification of the crude by chromatographic column (3:7 EtOAc: petroleum ether) afforded 140 mg of a pale yellow solid. Yield=22% $^1$HNMR (DMSO, 400 MHz) δ 1.15 (3H, t), 3.38 (2H, q), 3.50 (4H, m), 3.70 (4H, m), 4.40 (2H, d), 5.20 (1H, s), 6.18 (1H, s), 6.80 (1H, s), 7.20 (1H, s), 7.42 (2H, d), 7.76 (2H, d), 7.82 (2H, d), 8.18 (2H, d), 8.89 (1H, bt) [M$^{+1}$] 626.9 (C$_{28}$H$_{28}$ClF$_3$N$_4$O$_5$S requires 625.06).

Example 18

2-[ethyl-(4-fluorophenyl)sulfonyl-amino]-N-[[2-pyrrolidin-1-yl-6-[4-(trifluoromethoxy)phenyl]-4-pyridyl]methyl]prop-2-enamide

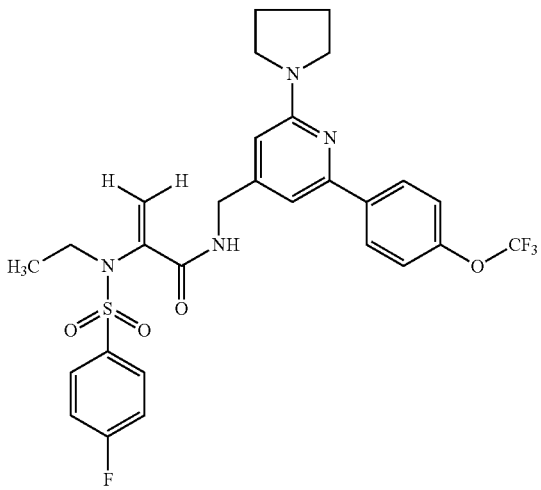 [SMILES: C=C(C(=O)NCc1cc(-c2ccc(OC(F)(F)F)cc2)nc(N2CCCC2)c1)N(CC)S(=O)(=O)c1ccc(F)cc1]

Synthesis of 2-pyrrolidin-1-yl-6-[4-(trifluoromethoxy)phenyl]pyridine-4-carbonitrile 26C A solution of nitrile 25A (2.58 g, 12.5 mmol) in DME (90 mL) was added with 4-trifluoromethoxy phenyl boronic acid (2.64 g, 1.0 mol eq,) and NaHCO3 (3.15 g, 3 mol eq,) suspended in water (45 mL). The mixture was degassed under vacuum, then Palladium Tetrakis was added (catalytic amount) and the reaction was stirred at 100° C. under inert atmosphere for 12 h. The solvent was removed under reduced pressure and water was added to the residue (80 mL). The aqueous phase was extracted with EtOAc (3×60 mL) and the combined organic layer was washed with brine (80 mL) and dried over Na$_2$SO$_4$. The solvent was evaporated under vacuum to afford 26C as deliquescent yellow solid (3.2 g, 9.6 mmol, 77% Yield). $^1$HNMR (DMSO, 400 MHz) δ 1.85 (m, 4H), 3.42 (m, 4H), 6.38 (s, 1H), 7.08 (s, 1H), 7.38 (d, 2H, J=8), 8.05 (d, 2H, J=8).

Synthesis of [2-pyrrolidin-1-yl-6-[4-(trifluoromethoxy)phenyl]-4-pyridyl]methanamine 27C A solution of nitrile 26C (1.1 g, 3.3 mmol) in diethyl ether (30 mL) was added in small amounts to a mixture of LiAlH$_4$ (0.25 g, 2 mol eq) in diethyl ether (30 mL) stirred at 0° C. After the addition was completed, the mixture was stirred at room temperature overnight. The excess of LiAlH$_4$ was destroyed at 0° C. by addition of small amount of water (30 mL), the solid formed was filtered off and the organic filtrate was separated, washed with brine (50 mL) and dried over Na$_2$SO$_4$. The organic phase was evaporated under reduced pressure and the residue was purified by flash chromatography (7:3 EtOAc:MeOH) to afford 27C as a pale yellow oil (0.87 g, 77% yield). $^1$HNMR (DMSO, 400 MHz) δ 1.97 (m, 4H), 3.48 (m, 4H), 3.68 (s, 2H), 4.15 (bs, 2H), 6.44 (s, 1H), 7.15 (s, 1H), 7.43 (d, 2H, J=8), 8.17 (d, 2H, J=8).

Preparation of 2-[ethyl-(4-fluorophenyl)sulfonyl-amino]-N-[[2-pyrrolidin-1-yl-6-[4-(trifluoromethoxy)phenyl]-4-pyridyl]methyl]prop-2-enamide Example 18

A solution of acid 4B (0.21 g, 0.76 mmol) in THF (20 mL) was added with DEPC (0.15 mL, 1.3 mol eq) and the mixture was stirred at room temperature for about 5 minutes. Then [2-pyrrolidin-1-yl-6-[4-(trifluoromethoxy)phenyl]-4-pyridyl]methanamine 27C (0.29 g, 1.1 mol eq) and a catalytic amount of TEA were added, then the reaction mixture was stirred at room temperature overnight. The solvent was removed under reduced pressure, the residue was suspended in EtOAc (30 mL) and washed with water (50 mL) and brine. The separated organic phase, after drying over Na$_2$SO$_4$, was evaporated under reduced pressure and the residue was purified by flash chromatography (7:3 Petroleum ether: EtOAc:) to afford a white solid after recrystallization from diethyl ether (0.10 g, 22%Yield). $^1$HNMR (DMSO, 200 MHz) δ 1.08 (t, 3H, J=6.8 Hz), 1.94 (m, 4H), 3.39 (m, 2H), 3.44 (m, 4H), 4.37 (d, 2H, J=6), 5.13 (s, 1H), 6.11 (s, 1H), 6.42 (s, 1H), 7.11 (s, 1H), 7.46-7.38 (m, 4H), 7.87 (m, 2H), 8.17 (d, 2H, J=9.6), 8.77 (t, 1H); [M$^{+1}$] 592.60 (C$_{28}$H$_{28}$F$_4$N$_4$O$_4$S requires 592.17).

Example 19

N-[[2,6-bis[4-(trifluoromethyl)phenyl]-4-pyridyl]methyl]-2-[(4-chlorophenyl)sulfonyl-ethyl-amino]prop-2-enamide

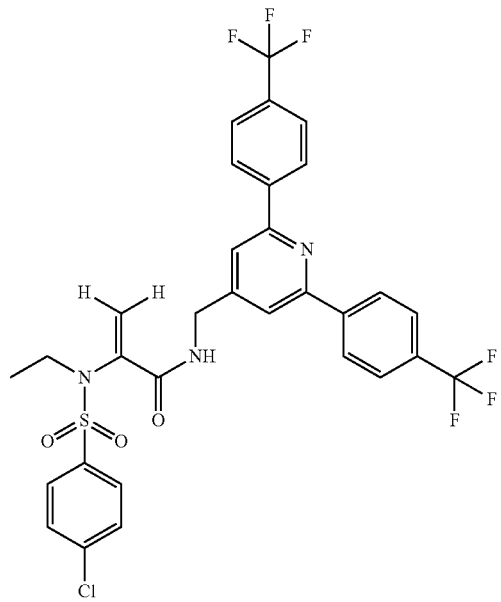 [SMILES: C=C(C(=O)NCc1cc(-c2ccc(C(F)(F)F)cc2)nc(-c2ccc(C(F)(F)F)cc2)c1)N(CC)S(=O)(=O)c1ccc(Cl)cc1]

Synthesis of 2,6-bis[4-(trifluoromethyl)phenyl]pyridine-4-carbonitrile 28A 2-6-dichloropyridine-4-carbonitrile 24 (3.7 g, 21.35 mmol) was dissolved in 100 ml of dimethoxyethane. To the solution were added 70 ml of water, sodium bicarbonate (3 equiv., 5.38 g), [4-(trifluoromethyl)phenyl]boronic acid (2.4 equiv., 9.74 g) and the mixture was stirred at rt for 5'. The mixture was degassed and put under argon. A catalytic amount of tetrakispalladium was added and the mixture was heated at 100° C. overnight. The solvents were evaporated off and the residue was dissolved with ethyl acetate, washed with water and brine. The organic phase was dried over sodium sulfate and concentrated under vacuum. The crude was crystallized from ethyl acetate and petroleum ether to give 28A as a beige solid. (2.5 g, 30% yield)

Synthesis of [2,6-bis[4-(trifluoromethyl)phenyl]-4-pyridyl]methanamine 29A

The nitrile 28A (4.7 g, 12 mmol) dissolved in 50 ml of diethyl ether was added dropwise to a mixture of LiAlH$_4$ (912 mg, 2 equiv.) in diethyl ether (80 mL) stirred at 0° C. Then the mixture was stirred at room temperature overnight. The excess of LiAlH$_4$ was destroyed by water addition at 0° C., the solid formed was filtered, washed with Et$_2$O and the filtrate was dried over Na$_2$SO$_4$ and evaporated to dryness to obtain 2.5 g of the amine 29A as yellow solid. Yield=52% $^1$HNMR (DMSO, 400 MHz) δ 2.25 (2H, bs), 3.90 (2H, s), 7.90 (4H, d, J=8 Hz), 8.11 (2H, s), 8.40 (4H, d, J=8 Hz)

Preparation of N-[[2,6-bis[4-(trifluoromethyl)phenyl]-4-pyridyl]methyl]-2-[(4-chlorophenyl)sulfonyl-ethyl-amino]prop-2-enamide Example 19

Acid 4D (289.74 mg, 1 mmol) was dissolved in 10 ml of THF and at rt DEPC (1.1 equiv, 0.15 ml) and [2,6-bis[4-(trifluoromethyl)phenyl]-4-pyridyl]methanamine 29A (1.1 equiv., 400 mg) were added to the solution. The mixture was stirred at rt overnight then evaporated. The residue was dissolved in AcOEt (30 ml) and washed with water (1×20 ml) and brine. The organic phase was dried over sodium sulfate and concentrated under vacuum. The purification of the crude by chromatographic column (3:7 EtOAc:petroleum ether) afforded 140 mg of a white solid. Yield=21% $^1$HNMR (DMSO, 400 MHz) δ 1.25 (3H, t), 3.40 (2H, q), 4.60 (2H, d), 5.18 (1H, s), 6.18 (1H, s), 7.70 (2H, d), 7.82 (2H, d), 7.86 (4H, d), 8.02 (2H, s), 8.40 (4H, d), 8.89 (1H, bt) [M$^{+1}$] 668.9 (C$_{31}$H$_{24}$ClF$_6$N$_3$O$_3$S requires 668.05).

Example 20

N-[[2,6-bis[4-(trifluoromethoxy)phenyl]-4-pyridyl]methyl]-2-[(4-chlorophenyl)sulfonyl-methyl-amino]prop-2-enamide

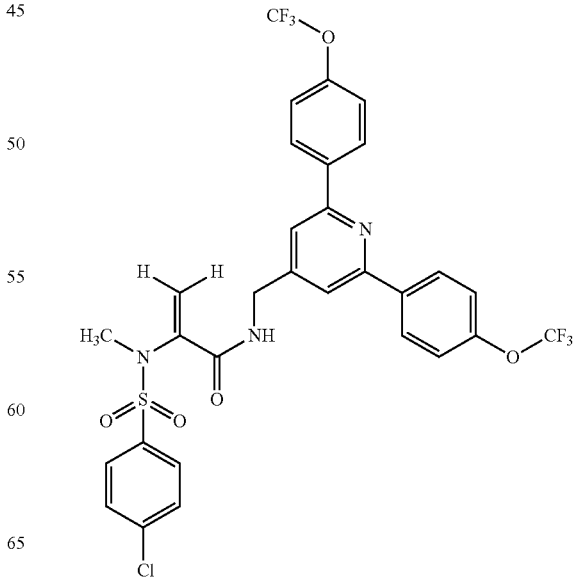

Synthesis of 2,6-bis[4-(trifluoromethoxy)phenyl] pyridine-4-carbonitrile 28B A solution of 24 (4.0 g, 19.4 mmol) in DME (120 mL) was added with 4-trifluoromethoxy phenyl boronic acid (1.1 mol eq, 4.2 g) and NaHCO3 (3 mol eq, 4.9 g) suspended in water (90 mL). The mixture was degassed under vacuum, then a catalytic amount of Tetrakispalladium was added and the reaction was stirred at 100° C. under inert atmosphere for 12 h. The solvent was removed under reduced pressure and water was added to the residue (100 mL). The aqueous phase was extracted with EtOAc (3×60 mL) and the combined organic layer was washed with brine (80 mL) and dried over $Na_2SO_4$. The solvent was evaporated under vacuum to afford 28B as deep yellow solid after recrystallization from diethyl ether/petroleum ether (68% Yield, 5.4 g, 13.8 mmol). $^1$HNMR (DMSO, 400 MHz) δ 7.53 (d, 4H, J=7.8), 8.38 (d, 4H, J=7.9), 8.48 (s, 2H).

Synthesis of [2,6-bis[4-(trifluoromethoxy)phenyl]-4-pyridyl]methanamine 29B

A solution of nitrile 28B (2.0 g, 5.1 mmol) in diethyl ether (40 mL) was added in small amounts to a mixture of $LiAlH_4$ (0.39 g, 2 mol eq) in diethyl ether (50 mL) stirred at 0° C. After the addition was completed, the mixture was stirred at room temperature overnight. The excess of $LiAlH_4$ was destroyed at 0° C. by addition of small amount of water (40 mL), the solid formed was filtered off and the organic filtrate was separated, washed with brine (50 mL) and dried over $Na_2SO_4$. The organic phase was evaporated under reduced pressure to afford 29B as a pale orange oil (83% yield, 1.67 g, 4.2 mmol,). $^1$HNMR (DMSO, 400 MHz) δ 3.321 (bs, 2H), 4.01 (s, 2H), 7.50 (d, 4H, J=7.9), 7.98 (s, 2H), 8.31 (d, 4H, J=8).

Preparation of N-[[2,6-bis[4-(trifluoromethoxy)phenyl]-4-pyridyl]methyl]-2-[(4-chlorophenyl)sulfonyl-methyl-amino]prop-2-enamide Example 20

A solution of acid 4C (0.50 g, 1.8 mmol) in THF (30 mL) was added with DEPC (0.35 mL, 1.3 mol eq) and the mixture was stirred at room temperature several minutes.
Then [2,6-bis[4-(trifluoromethoxy)phenyl]-4-pyridyl]methanamine 29B (0.66 g, 1.1 mol eq) and a catalytic amount of TEA were added, then the reaction mixture was stirred at room temperature overnight. The solvent was removed under reduced pressure, water was added to the residue that is extracted with EtOAc (3×30 mL) and washed with brine (1×50 mL). The separated organic phase was dried over $Na_2SO_4$, evaporated to dryness and the residue was purified by flash chromatography (6:4 EtOAc:Petroleum ether) to afford a white solid (0.22 g) after crystallization from diethyl ether. Yield=18%, $^1$HNMR (DMSO, 400 MHz) δ 2.96 (s, 3H), 4.55 (d, 2H, J=4), 5.13 (s, 1H), 5.90 (s, 1H), 7.49 (d, 4H), 7.25 (d, 2H), 7.79 (d, 2H), 7.96 (s, 2H), 8.31 (d, 4H, J=6.8), 9.00 (t, 1H); [M$^{+1}$] 686.02 ($C_{30}H_{22}ClF_6N_3O_5S$ requires 685.08).

Example 21

(Z)-2-[(4-fluorophenyl)sulfonyl-methyl-amino]-N-[[2-[4-(trifluoromethoxy)phenyl]-4-pyridyl]methyl]but-2-enamide

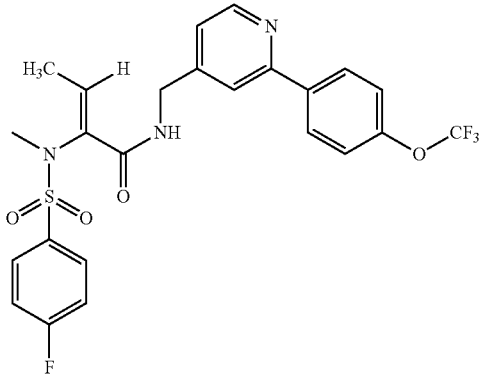 [SMILES: C/C=C(/C(=O)NCc1ccnc(-c2ccc(OC(F)(F)F)cc2)c1)N(C)S(=O)(=O)c1ccc(F)cc1]

Synthesis of methyl (2S)-2-[(4-fluorophenyl)sulfonylamino]-3-hydroxy-butanoate 9A To L-threonine methyl ester hydrochloride 8 (4.8 g, 28.33 mmol) dissolved in methylene chloride (200 ml) was added with TEA (2 equiv., 7.89 ml) and in one portion 4-fluorobenzenesulfonyl chloride (1.0 equiv., 28.79 mmol, 5.6 g). The reaction was refluxed for 4 hours. The solvent was evaporated and the crude was dissolved in AcOEt (100 ml) and washed with water (1×80 ml) and brine. The organic phase was dried over sodium sulfate and concentrated under vacuum. The purification of the crude residue by crystallization from diethyl ether and petroleum ether afforded 7.45 g of the white product 9A. Yield=90% $^1$HNMR (DMSO, 200 MHz) δ 1.01 (3H, d, J=6.2 Hz), 3.39 (3H, s), 3.78 (1H, bs), 3.96 (1H, m), 4.93 (1H, d, J=5.6 Hz), 7.39 (2H, m), 7.83 (2H, m), 8.12 (1H, bs)

Synthesis of methyl (2S)-2-[methyl-(4-fluorophenyl)sulfonyl-amino]-3-hydroxy-butanoate 10A Compound 9A (5.5 g, 19 mmol) dissolved in DMF (15 ml) was added with $K_2CO_3$ (1.1 equiv., 2.75 g) and methyl iodide (1.1 equiv., 1.94 ml) and the reaction was stirred at rt overnight. The reaction was diluted with ethyl acetate and washed several times with water and finally with Brine. The organic phase was dried over sodium sulfate and concentrated under vacuum. The purification of the crude residue by crystallization from ethyl ether and petroleum ether afforded 5 g of 10A as a semisolid. Yield=86%. $^1$HNMR (DMSO, 200 MHz) δ 1.10 (3H, d, J=6.2 Hz), 2.94 (3H, s), 3.46 (3H, s), 4.22 (1H, q, J=6.4 Hz), 4.39 (1H, d, J=5.2 Hz), 5.16 (1H, d, J=3.2 Hz), 7.40 (2H, m), 7.82 (2H, m)

Synthesis of (Z)-2-[methyl-(4-fluorophenyl)sulfonyl-amino]but-2-enoic acid 11A Compound 10A (4.576 g, 15 mmol) dissolved in THF (30 ml) and water (10 ml) was added with $LiOH.H_2O$ (3 equiv., 1.88 g) and the reaction was stirred at rt for 3 hours. The reaction was concentrated under vacuum. Water was added and then 10% HCl till precipitation of the acid. The acid was extracted with ethyl acetate and the organic phase was washed with Brine, dried over sodium sulfate and concentrated under vacuum to give 4 g of a white solid. Yield=93%. $^1$HNMR (DMSO, 200 MHz) δ 1.08 (3H, t, J=7 Hz), 2.95 (3H, s), 4.02 (1H, q), 4.26 (1H, bs), 5.08 (1H, bs), 7.43 (2H, m), 7.85 (2H, m), 12.84 (1H, bs). The intermediate acid (2 g, 9.7 mmol) dissolved in pyridine (10 ml) was added dropwise with acetyl chloride (1.4 equiv., 1.1 ml) at 0° C. and the reaction was then stirred at rt for 5 hours. The reaction was quenched by addition of 10% HCl and then extracted with ethyl acetate. The organic phase was washed 2 times with water, with brine, dried over sodium sulfate and concentrated under vacuum. The crude product was crystallized from diethyl ether and petroleum ether to give 1 g of a beige solid. Yield=50%. $^1$HNMR (DMSO, 200 MHz) δ 1.76 (3H, d, J=7 Hz), 2.95 (3H, s), 7.04 (1H, q, J=7 Hz), 7.45 (2H, m), 7.83 (2H, m), 12.74 (1H, bs)

Preparation of (Z)-2-[methyl-(4-fluorophenyl)sulfonyl-amino]-N-[[2-[4-(trifluoromethoxy)phenyl]-4-pyridyl]methyl]but-2-enamide Example 21

Acid 11A (515 mg, 2.5 mmol) was dissolved in 10 ml of THF and at rt DEPC (1.1 equiv, 0.38 ml) and [2-[4-(trifluoromethoxy)phenyl]-4-pyridyl]methanamine 21B (1.1 equiv., 737 mg) were added to the solution. The mixture was stirred at rt overnight then evaporated. The residue was dissolved in AcOEt (30 ml) and washed with water (1×20 ml) and brine. The organic phase was dried over sodium sulfate and concentrated under vacuum. The purification of the crude by chromatographic column (1:1 EtOAc:petroleum ether) afforded 200 mg of a pale yellow solid. Yield=15% $^1$HNMR (DMSO, 200 MHz) δ 1.74 (3H, d J=7.4 Hz), 3.06 (3H, s), 4.40 (2H, d, J=6 Hz), 6.83 (1H, q, J=7 Hz), 7.44 (5H, m), 7.83 (3H, m), 8.18 (2H, d, J=8.2 Hz), 8.59 (1H, d, J=5.2 Hz), 8.70 (1H, bt) [M$^{+1}$] 524.3 ($C_{24}H_{21}F_4N_3O_4S$ requires 523.50).

Example 22

(Z)-2-[ethyl-(4-fluorophenyl)sulfonyl-amino]-N-[[2-[4-(trifluoromethoxy)phenyl]-4-pyridyl]methyl]but-2-enamide

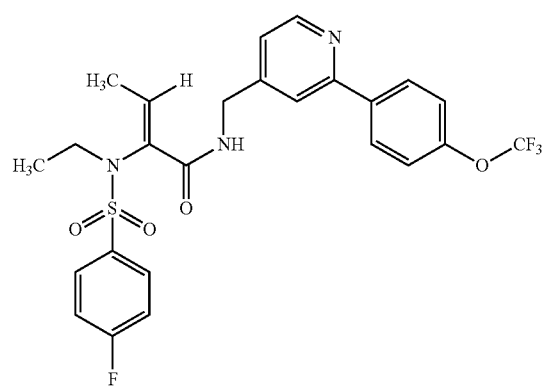 [SMILES: C/C=C(/C(=O)NCc1ccnc(-c2ccc(OC(F)(F)F)cc2)c1)N(CC)S(=O)(=O)c1ccc(F)cc1]

Synthesis of methyl (2S)-2-[ethyl-(4-fluorophenyl) sulfonyl-amino]-3-hydroxy-butanoate 10B Compound 9A (1 g, 3.0 mmol) dissolved in DMF (10 ml) was added with $K_2CO_3$ (1.1 equiv., 456 mg) and ethyl iodide (1.1 equiv., 0.316 ml) and the reaction was stirred at rt overnight. The reaction was diluted with ethyl acetate and washed several times with water and finally with Brine. The organic phase was dried over sodium sulfate and concentrated under vacuum. The purification of the crude residue by crystallization from ethyl ether and petroleum ether afforded 895 mg of a semisolid. Yield=93%. $^1$HNMR (DMSO, 200 MHz) δ 1.13 (3H, d, J=6.2 Hz), 1.26 (3H, t, J=7 Hz), 3.32 (3H, s), 3.41 (2H, q, J=7.8 Hz), 4.02 (1H, bs), 4.23 (1H, m), 5.13 (1H, d, J=4.6 Hz), 7.42 (2H, m), 7.84 (2H, m)

Synthesis of (Z)-2-[ethyl-(4-fluorophenyl)sulfonyl-amino]but-2-enoic acid 11B

Compound 10B (895 mg, 2.8 mmol) dissolved in THF (10 ml) and water (5 ml) was added with LiOH.H$_2$O (3 equiv., 352 mg) and the reaction was stirred at rt 3 hours. The reaction was concentrated under vacuum. Water was added and 10% HCl till precipitation of the acid. The acid was extracted with ethyl acetate and the organic phase was washed with Brine, dried over sodium sulfate and concentrated under vacuum to give 770 mg of a white solid. Yield=96%. $^1$HNMR (DMSO, 200 MHz) δ 1.00 (3H, t, J=7.2 Hz), 1.17 (3H, t, J=7 Hz), 3.34 (2H, q, J=7.8 Hz), 4.02 (1H, m), 4.21 (1H, bs), 5.13 (1H, bs), 7.43 (2H, m), 7.85 (2H, m), 12.84 (1H, bs). The intermediate acid (1.6 g, 7 mmol) dissolved in pyridine (10 ml) was added dropwise with acetyl chloride (1.4 equiv., 0.8 ml) at 0° C. and the reaction was then stirred at rt for 5 hours. The reaction was quenched by addition of 10% HCl and then extracted with ethyl acetate. The organic phase was washed 2 times with water, with brine, dried over sodium sulfate and concentrated under vacuum. The crude product was crystallized from diethyl ether and petroleum ether to give 650 mg of 11B as a beige solid. Yield=32%. $^1$HNMR (DMSO, 200 MHz) δ 1.00 (3H, t, J=7.4 Hz), 1.80 (3H, d J=7.2 Hz), 3.47 (2H, m), 7.18 (1H, q, J=6.6 Hz), 7.43 (2H, m), 7.83 (2H, m), 12.64 (1H, bs)

Preparation of (Z)-2-[ethyl-(4-fluorophenyl)sulfonyl-amino]-N-[[2-[4-(trifluoromethoxy)phenyl]-4-pyridyl]methyl]but-2-enamide Example 22

Acid 11B (574 mg, 2 mmol) was dissolved in 10 ml of THF and at rt DEPC (1.1 equiv, 0.3 ml) and [2-[4-(trifluoromethoxy)phenyl]-4-pyridyl]methanamine 21B (1.1 equiv., 590 mg) were added to the solution. The mixture was stirred at rt overnight then evaporated. The residue was dissolved in AcOEt (30 ml) and washed with water (1×20 ml) and brine. The organic phase was dried over sodium sulfate and concentrated under vacuum. The purification of the crude by chromatographic column (1:1 EtOAc:petroleum ether) afforded 195 mg of a white solid. Yield=18% $^1$HNMR (DMSO, 200 MHz) δ 1.00 (3H, t, J=7.2 Hz), 1.46 (3H, d J=7.4 Hz), 3.43 (2H, q, J=7 Hz), 4.40 (2H, d, J=6 Hz), 6.83 (1H, q, J=7 Hz), 7.25 (1H, dd, J=6.4 Hz), 7.42 (4H, m), 7.85 (3H, m), 8.18 (2H, d, J=8.2 Hz), 8.60 (1H, d, J=5 Hz), 8.74 (1H, bt) [M$^{+1}$] 538.1 ($C_{25}H_{23}F_4N_3O_4S$ requires 537.53).

Example 23

(Z)-2-[(4-chlorophenyl)sulfonyl-methyl-amino]-N-[[3-[4-(trifluoromethyl)phenyl]phenyl]methyl]but-2-enamide

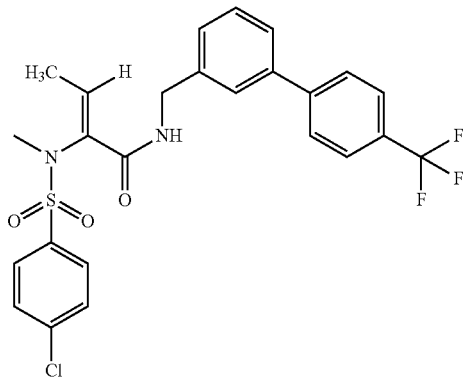 [SMILES: C/C=C(/C(=O)NCc1cccc(-c2ccc(C(F)(F)F)cc2)c1)N(C)S(=O)(=O)c1ccc(Cl)cc1]

Synthesis of methyl (2S)-2-[(4-chlorophenyl)sulfonylamino]-3-hydroxy-butanoate 9C L-Threonine methyl ester hydrochloride 8 (4.8 g, 28.33 mmol) dissolved in methylene chloride (200 ml) was added with TEA (2 equiv., 7.89 ml) and in one portion 4-chlorobenzenesulfonyl chloride (1.0 equiv., 5.97 g). The reaction was refluxed for 4 hours. The solvent was evaporated and the crude was dissolved in AcOEt (100 ml) and washed with water (1×80 ml) and brine. The organic phase was dried over sodium sulfate and concentrated under vacuum. The purification of the crude residue by crystallization from diethyl ether and petroleum ether afforded 9.6 g of the white product. Yield=98% $^1$HNMR (DMSO, 200 MHz) δ 1.00 (3H, d, J=6.4 Hz), 3.40 (3H, s), 3.78 (1H, d, J=4 Hz), 3.95 (1H, m), 4.96 (1H, d, J=5.6 Hz), 7.64 (2H, m), 7.77 (2H, m), 8.12 (1H, bs)

Synthesis of methyl (2S)-2-[methyl-(4-chlorophenyl)sulfonyl-amino]-3-hydroxy-butanoate 10C Compound 9C (3, 8.7 mmol) dissolved in DMF (10 ml) was added with $K_2CO_3$ (1.1 equiv., 1.3) and methyl iodide (1.1 equiv., 0.88 ml) and the reaction was stirred at rt overnight. The reaction was diluted with ethyl acetate and washed several times with water and finally with Brine. The organic phase was dried over sodium sulfate and concentrated under vacuum. The purification of the crude residue by crystallization from ethyl ether and petroleum ether afforded 2.85 g of 10C as a semisolid. Yield=93.7%.
$^1$HNMR (DMSO, 200 MHz) δ 1.08 (3H, d, J=6.4 Hz), 2.94 (3H, s), 3.46 (3H, s), 4.22 (1H, q), 4.41 (1H, d), 5.20 (1H, d), 7.65 (2H, m), 7.74 (2H, m)

Synthesis of (Z)-2-[methyl-(4-chlorophenyl)sulfonyl-amino]but-2-enoic acid 11C Compound 10C (2.85 g, 8.15 mmol) dissolved in THF (30 ml) and water (10 ml) was added with $LiOH.H_2O$ (3 equiv., 1.03 g) and the reaction was stirred at rt for 3 hours. The reaction was concentrated under vacuum. Water was added and then 10% HCl till precipitation of the acid. The acid was extracted with ethyl acetate and the organic phase was washed with Brine, dried over sodium sulfate and concentrated under vacuum to give 2.5 g of a white solid. Yield=91%. $^1$HNMR (DMSO, 200 MHz) δ 1.08 (3H, t, J=7 Hz), 2.73 (3H, s), 4.02 (1H, q), 4.26 (1H, bs), 5.02 (1H, bs), 7.63 (2H, m), 7.79 (2H, m), 12.09 (1H, bs) The intermediate acid (2.5 g, 7.45 mmol) dissolved in pyridine (10 ml) was added dropwise with acetyl chloride (1.4 equiv., 0.83 ml) at 0° C. and the reaction was then stirred at 50° C. for 5 hours. The reaction was quenched by addition of 10% HCl and then extracted with ethyl acetate. The organic phase was washed 2 times with water, with brine, dried over sodium sulfate and concentrated under vacuum. The crude product was crystallized from diethyl ether and petroleum ether to give 870 mg of 11C as a beige solid. Yield=40%. $^1$HNMR (DMSO, 200 MHz) δ 1.77 (3H, d, J=7.2 Hz), 3.32 (3H, s), 7.04 (1H, q, J=6.8 Hz), 7.64 (2H, m), 7.77 (2H, m), 12.74 (1H, bs)

Preparation of (Z)-2-[(4-chlorophenyl)sulfonyl-methyl-amino]-N-[[3-[4-(trifluoromethyl)phenyl]phenyl]methyl]but-2-enamide Example 23

Acid 11C (868 mg, 3 mmol) was dissolved in 10 ml of THF and at rt DEPC (1.1 equiv, 0.5 ml) and [3-[4-(trifluoromethyl)phenyl]phenyl]methanamine 23A (1.1 equiv., 837 mg) were added to the solution. The mixture was stirred at rt overnight then evaporated. The residue was dissolved in AcOEt (30 ml) and washed with water (1×20 ml) and brine. The organic phase was dried over sodium sulfate and concentrated under vacuum. The purification of the crude by chromatographic column (3:7 EtOAc:petroleum ether) afforded 200 mg of a pale yellow solid. Yield=13% $^1$HNMR (DMSO, 200 MHz) δ 1.47 (3H, d, J=7 Hz), 3.01 (3H, s), 4.27 (2H, d, J=6.2 Hz), 6.68 (1H, q), 7.60 (12H, m), 8.64 (1H, bt) [$M^{+1}$] 523.2 ($C_{25}H_{22}ClF_3N_2O_3S$ requires 522.97).

Example 24

(Z)-2-[(4-chlorophenyl)sulfonyl-ethyl-amino]-N-[[3-[4-(trifluoromethyl)phenyl]phenyl]methyl]but-2-enamide

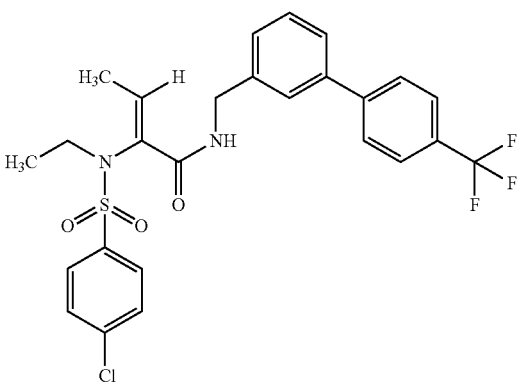 [SMILES: C/C=C(/C(=O)NCc1cccc(-c2ccc(C(F)(F)F)cc2)c1)N(CC)S(=O)(=O)c1ccc(Cl)cc1]

Synthesis of methyl (2S)-2-[ethyl-(4-chlorophenyl)sulfonyl-amino]-3-hydroxy-butanoate 10D Compound 9C (3 g, 8.94 mmol) dissolved in DMF (15 ml) was added with $K_2CO_3$ (1.1 equiv., 1.36 g) and ethyl iodide (1.1 equiv., 1 ml) and the reaction was stirred at rt overnight. The reaction was diluted with ethyl acetate and washed several times with water and finally with Brine. The organic phase was dried over sodium sulfate and concentrated under vacuum. The purification of the crude residue by crystallization from ethyl ether and petroleum ether afforded 2.8 g of a semisolid. Yield=97%. $^1$HNMR (DMSO, 200 MHz) δ 1.00 (3H, d, J=6.2 Hz), 1.26 (3H, t, J=7 Hz), 3.32 (3H, s), 3.34 (2H, m), 4.02 (1H, bs), 4.23 (1H, m), 5.14 (1H, d, J=4.4 Hz), 7.62 (2H, m), 7.76 (2H, m)

Synthesis of (Z)-2-[ethyl-(4-chlorophenyl)sulfonyl-amino]but-2-enoic acid 11D

Compound 10D (2.08 g, 6.2 mmol) dissolved in THF (20 ml) and water (5 ml) was added with LiOH.H$_2$O (3 equiv., 783 mg) and the reaction was stirred at rt 3 hours. The reaction was concentrated under vacuum. Water was added and 10% HCl till precipitation of the acid. The acid was extracted with ethyl acetate and the organic phase was washed with Brine, dried over sodium sulfate and concentrated under vacuum to give 1.75 g of a white solid. Yield=88%. $^1$HNMR (DMSO, 200 MHz) δ 1.02 (3H, t, J=6.4 Hz), 1.17 (3H, t, J=7 Hz), 3.31 (2H, m), 4.02 (1H, m), 4.21 (1H, bs), 5.13 (1H, bs), 7.63 (2H, m), 7.78 (2H, m), 12.88 (1H, bs). The intermediate acid (1.75 g, 5.44 mmol) dissolved in pyridine (10 ml) was added dropwise with acetyl chloride (1.4 equiv., 0.6 ml) at 0° C. and the reaction was then stirred at rt for 5 hours. The reaction was quenched by addition of 10% HCl and then extracted with ethyl acetate. The organic phase was washed 2 times with water, with brine, dried over sodium sulfate and concentrated under vacuum. The crude product was crystallized from diethyl ether and petroleum ether to give 600 mg of 11D as a beige solid. Yield=36%. $^1$HNMR (DMSO, 200 MHz) δ 1.00 (3H, t, J=7.2 Hz), 1.80 (3H, d, J=7 Hz), 3.45 (2H, m), 7.20 (1H, q), 7.63 (2H, d, J=8.6 Hz), 7.76 (2H, d, J=8.6 Hz), 12.64 (1H, bs)

Preparation of (Z)-2-[(4-chlorophenyl)sulfonyl-ethyl-amino]-N-[[3-[4-(trifluoromethyl)phenyl]phenyl]methyl]but-2-enamide Example 24

Acid 11D (600 mg, 1.97 mmol) was dissolved in 10 ml of THF and at rt DEPC (1.1 equiv, 0.3 ml) and [3-[4-(trifluoromethyl)phenyl]phenyl]methanamine 23A (1.1 equiv., 550 mg) were added to the solution. The mixture was stirred at rt overnight then evaporated. The residue was dissolved in AcOEt (30 ml) and washed with water (1×20 ml) and brine. The organic phase was dried over sodium sulfate and concentrated under vacuum. The purification of the crude by chromatographic column (3:7 EtOAc:petroleum ether) afforded 150 mg of a white solid. Yield=14% $^1$HNMR (DMSO, 200 MHz) δ 0.98 (3H, t, J=7.2 Hz), 1.53 (3H, d J=7.4 Hz), 3.36 (2H, q, J=7 Hz), 4.28 (2H, d, J=6 Hz), 6.80 (1H, q, J=7 Hz), 7.8 (12H, m), 8.60 (1H, bt) [M$^{+1}$] 537.1 (C$_{26}$H$_{24}$ClF$_3$N$_2$O$_3$S requires 536.99).

Example 25

1-[ethyl-(4-fluorophenyl)sulfonyl-amino]-N-[[2-[4-(trifluoromethyl)phenyl]-4-pyridyl]methyl]cyclopropanecarboxamide

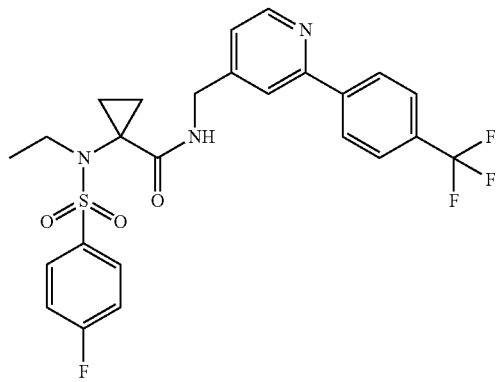 [SMILES: CCN(C1(C(=O)NCc2ccnc(-c3ccc(C(F)(F)F)cc3)c2)CC1)S(=O)(=O)c1ccc(F)cc1]

Synthesis of methyl 1-[(4-fluorophenyl)sulfonyl-amino]cyclopropanecarboxylate 13A A suspension of methyl-1-aminocyclopropane carboxylate hydrochloride 12 (0.6 g, 3.96 mmol) in CH$_2$Cl$_2$ (60 mL) was added with TEA (1.1 mol eq, 0.6 mL) and the mixture was stirred at r.t. for 10 minutes. Then 4-fluorobenzensulfonyl chloride (1 mol eq, 0.77 g) and additional TEA (1.1 mol eq) were added and the solution was heated at 60° C. overnight. The solvent was removed under reduced pressure, water was added to the residue (100 mL) and the aqueous phase was extracted with EtOAc (3×40 mL). The combined organic phases were dried over Na$_2$SO$_4$ and evaporated under reduced pressure to afford 13A as transparent oil (1.07 g, 99% yield). $^1$HNMR (DMSO, 200 MHz) δ 1.17 (m, 2H), 1.27 (m, 2H), 3.32 (s, 3H), 7.46 (t, 2H, J=9), 7.80 (m, 2H), 8.78 (bs, 1H).

Synthesis of methyl 1-[ethyl-(4-fluorophenyl)sulfonyl-amino]cyclopropanecarboxylate 14A A solution of 13A (1 g, 3.67 mmol) in DMF (15 mL) was added with an. K$_2$CO$_3$ (1.5 mol eq, 0.76 g) and, after few minutes, 2-iodoethane (1.2 mol eq, 0.45 ml) was added and the mixture was heated at 50° C. for 12 h. The solvent was removed under reduced pressure, water was added to the residue (60 mL) and the aqueous phase was extracted with EtOAc (3×30 mL). The combined organic phases were dried over Na$_2$SO$_4$ and evaporated under reduced pressure to afford 14A as a pale yellow oil (1.1 g, 98% yield). $^1$HNMR (DMSO, 200 MHz) δ 1.095 (t, 3H, J=8), 4.43 (bs, 4H), 2.88 (s, 3H), 3.32 (m, 2H), 7.42 (t, 2H, J=8.2), 7.87 (m, 2H).

Synthesis of 1-[ethyl-(4-fluorophenyl)sulfonyl-amino]cyclopropanecarboxylic acid 15A A solution of 14A (1.3 g, 4.33 mmol) in dioxane (40 mL) was added with 10% NaOH aq. solution (20 mL) and the mixture was heated at 50° C. overnight. The organic solvent was removed under reduced pressure and the aqueous phase was acidified with 10% HCl. The solid formed was collected by filtration, washed with water (2×20 mL) and dried to afford 15A as white solid (1.0 g, 81% yield). $^1$HNMR (DMSO, 200 MHz) δ 1.10 (t, 3H, J=7.2), 1.65 (bs, 4H), 7.39 (m, 2H), 7.84 (m, 2H), 12.90 (bs, 1H).

Preparation of 1-[ethyl-(4-fluorophenyl)sulfonyl-amino]-N-[[2-[4-(trifluoromethyl)phenyl]-4-pyridyl]methyl]cyclopropanecarboxamide Example 25

Acid 15A (303 mg, 1 mmol) was dissolved in 5 ml of THF and at rt DEPC (1.1 equiv, 0.17 ml) and [2-[4-(trifluoromethyl)phenyl]-4-pyridyl]methanamine 21A (1.1 equiv., 277.5 mg) were added to the solution. The mixture was stirred at rt overnight then evaporated. he residue was dissolved in AcOEt (30 ml) and washed with water (1×20 ml) and brine. The organic phase was dried over sodium sulfate and concentrated under vacuum. The purification of the crude by chromatographic column (1:1 EtOAc:Petroleum ether) afforded 140 mg of a white solid. Yield=26.8% $^1$HNMR (DMSO, 400 MHz) δ 1.09 (2H, bs), 1.23 (3H, t, J=7.2 Hz), 1.40 (2H, bs), 3.40 (2H, q, J=6.8 Hz), 4.41 (2H, bs), 7.26 (1H, dd), 7.42 (2H, t, J=8.8 Hz), 7.87 (4H, m), 7.98 (1H, bs), 8.30 (3H, bd), 8.64 (1H, dd, J=4.8 Hz) [M$^{+1}$] 521.9 (C$_{25}$H$_{23}$F$_4$N$_3$O$_3$S requires 521.53).

Example 26

1-[ethyl-(4-fluorophenyl)sulfonyl-amino]-N-[[2-[4-(trifluoromethoxy)phenyl]-4-pyridyl]methyl]cyclopropanecarboxamide

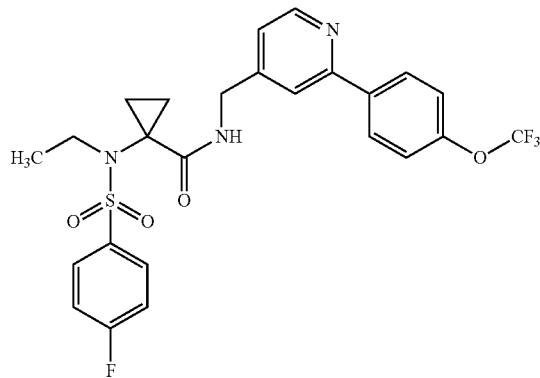 [SMILES: CCN(C1(C(=O)NCc2ccnc(-c3ccc(OC(F)(F)F)cc3)c2)CC1)S(=O)(=O)c1ccc(F)cc1]

Preparation of 1-[ethyl-(4-fluorophenyl)sulfonyl-amino]-N-[[2-[4-(trifluoromethoxy)phenyl]-4-pyridyl]methyl]cyclopropanecarboxamide Example 26

A solution of acid 15A (0.5 g, 1.7 mmol) in THF (30 mL) was added with DEPC (0.34 mL, 1.3 mol eq) and the mixture was stirred at room temperature for about 5 minutes. Then [2-[4-(trifluoromethoxy)phenyl]-4-pyridyl]methanamine 21B (0.51 g, 1.1 mol eq) and a catalytic amount of TEA were added, then the reaction mixture was stirred at room temperature overnight. The solvent was removed under reduced pressure, the residue was suspended in EtOAc (40 mL) and washed with water (50 mL) and brine. The separated organic phase was dried over Na$_2$SO$_4$ and evaporated under reduced pressure and the residue was purified by flash chromatography (7:3 EtOAc:Petroleum ether) to afford a white solid (0.18 g) after crystallization from diethyl ether. Yield=30%, $^1$HNMR (DMSO, 200 MHz) δ 1.09 (bs, 2H), 1.22 (t, 3H, J=8), 1.26 (bs, 2H), 3.41 (bs, 2H), 4.43 (d, 2H, J=6); 7.27 (d, 1H, J=4), 7.46-7.42 (m, 4H), 7.90 (m, 3H), 8.23 (m, 3H), 8.61 (d, 1H, J=5.2). [M$^{+1}$] 537.53 (C$_{25}$H$_{23}$F$_4$N$_3$O$_4$S requires 537.13).

Example 27

1-[(4-chlorophenyl)sulfonyl-ethyl-amino]-N-[[2-[4-(trifluoromethoxy)phenyl]-4-pyridyl]methyl]cyclopropanecarboxamide

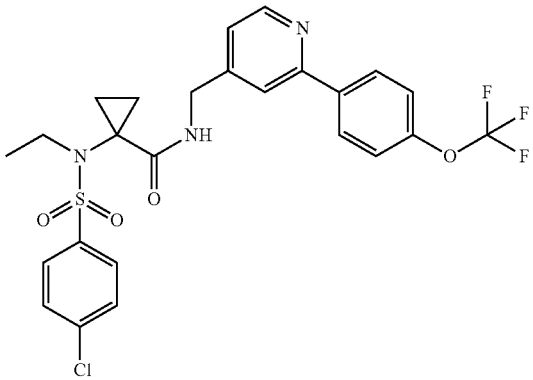 [SMILES: CCN(C1(C(=O)NCc2ccnc(-c3ccc(OC(F)(F)F)cc3)c2)CC1)S(=O)(=O)c1ccc(Cl)cc1]

Synthesis of methyl 1-[(4-chlorophenyl)sulfonylamino]cyclopropanecarboxylate 13B To methyl 1-aminocyclopropanecarboxylate hydrochloride 12 (500 mg, 3.298 mmol) dissolved in methylene chloride (20 ml) was added with TEA (2 equiv., 1 ml) and in one portion 4-chlorobenzenesulfonyl chloride (1.0 equiv., 765 mg). The reaction was refluxed for 4 hours. The solvent was evaporated and the crude was dissolved in EtOAc (50 ml) and washed with water (1×30 ml) and brine. The organic phase was dried over sodium sulfate and concentrated under vacuum. The purification of the crude residue by crystallization from diethyl ether and petroleum ether afforded 800 mg of the white product 13B. Yield=84% $^1$HNMR (DMSO, 200 MHz) δ 1.16 (2H, m), 1.30 (2H, m), 3.32 (3H, s), 7.70 (4H, m), 8.87 (1H, bs)

Synthesis of methyl 1-[(4-chlorophenyl)sulfonyl-ethyl-amino]cyclopropanecarboxylate 14B Compound 13B (800 mg, 2.76 mmol) dissolved in DMF (10 ml) was added with K$_2$CO$_3$ (1.1 equiv., 420 mg) and ethyl iodide (1.1 equiv., 0.3 ml) and the reaction was stirred at rt overnight. The reaction was diluted with ethyl acetate and washed several times with water and finally with Brine. The organic phase was dried over sodium sulfate and concentrated under vacuum. The purification of the crude residue by crystallization from ethyl ether and petroleum ether afforded 750 mg of 14B as a semisolid. Yield=85.5%. $^1$HNMR (DMSO, 200 MHz) δ 1.096 (3H, t, J=7.2 Hz), 1.17 (2H, m), 1.43 (2H, bs), 3.34 (2H, m), 3.43 (3H, s), 7.68 (2H, m), 7.79 (2H, m)

Synthesis of 1-[(4-chlorophenyl)sulfonyl-ethyl-amino]cyclopropanecarboxylic acid 15B Compound 14B (750 mg, 2.36 mmol) dissolved in THF (10 ml) and water (5 ml) was added with LiOH.H$_2$O (3 equiv., 297 mg) and the reaction was stirred at rt 3 hours. The reaction was concentrated under vacuum. Water was added and 10% HCl till precipitation of the acid. The acid was extracted with ethyl acetate and the organic phase was washed with Brine, dried over sodium sulfate and concentrated under vacuum to give 650 mg of 15B as a white solid. Yield=90%. $^1$HNMR (DMSO, 200 MHz) δ 1.06 (3H, t, J=7.2 Hz), 1.38 (2H, m), 1.35 (2H, bs), 3.33 (2H, m), 7.43 (2H, m), 7.77 (2H, m), 12.46 (1H, bs)

Preparation of 1-[(4-chlorophenyl)sulfonyl-ethyl-amino]-N-[[2-[4-(trifluoromethoxy)phenyl]-4-pyridyl]methyl]cyclopropanecarboxamide Example 27

Acid 15B (303 mg, 1 mmol) was dissolved in 5 ml of THF and at rt DEPC (1.1 equiv, 0.17 ml) and [2-[4-(trifluoromethoxy)phenyl]-4-pyridyl]methanamine 21B (1.1 equiv., 295 mg) were added to the solution. The mixture was stirred at rt overnight then evaporated. The residue was dissolved in AcOEt (30 ml) and washed with water (1×20 ml) and brine. The organic phase was dried over sodium sulfate and concentrated under vacuum. The purification of the crude by chromatographic column (3:7 EtOAc:Petroleum ether) afforded 100 mg of a white solid. Yield=18% $^1$HNMR (DMSO, 200 MHz) δ 1.12 (2H, bs), 1.22 (3H, t, J=7.2 Hz), 1.40 (2H, bs), 3.40 (2H, q, J=4.8 Hz), 4.41 (2H, d, J=5.4 Hz), 7.26 (1H, dd, J=3.8 Hz), 7.49 (2H, d, J=8 Hz), 7.65 (2H, dd, J=8.6 Hz), 7.84 (2H, dd, J=6.8 Hz, J'=1.6 Hz), 7.90 (1H, bs), 8.20 (2H, dd, J=6.8 Hz, J'=1.8 Hz), 8.28 (1H, t), 8.59 (1H, d, J=5.2 Hz) [M$^{+1}$] 553.9 (C$_{25}$H$_{23}$ClF$_3$N$_3$O$_4$S requires 553.98).

Example 28

1-[(5-chloro-2-thienyl)sulfonyl-ethyl-amino]-N-[[2-[4-(trifluoromethoxy)phenyl]-4-pyridyl]methyl]cyclopropanecarboxamide

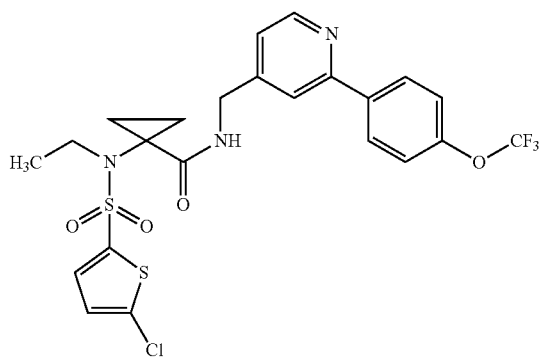 [SMILES: CCN(C1(C(=O)NCc2ccnc(-c3ccc(OC(F)(F)F)cc3)c2)CC1)S(=O)(=O)c1ccc(Cl)s1]

Synthesis of methyl 1-[(5-chloro-2-thienyl)sulfonylamino]cyclopropanecarboxylate 16

A suspension of methyl-1-aminocyclopropen carboxylate hydrochloride 12 (1 g, 1.43 mmol) in CH$_2$Cl$_2$ (100 mL) was added with TEA (1.1 mol eq, 1.01 mL) and the mixture was stirred at r.t. for 10 minutes. Then 5-chloro-thiophene-2-sulfonyl chloride (1 mol eq, 1.43 g) and additional TEA (1.1 mol eq) were added and the solution was heated at 50° C. overnight. The solvent was removed under reduced pressure, water was added to the residue (100 mL) and the aqueous phase was extracted with EtOAc (3×50 mL). The combined organic phases were dried over Na$_2$SO$_4$ and evaporated under reduced pressure to afford 16 as a pale orange oil (quantitative yield). $^1$HNMR (DMSO, 200 MHz) δ 1.23 (m, 2H), 1.35 (m, 2H), 1.98 (s, 3H), 7.23 (d, 1H, J=4), 7.73 (d, 1H, J=3.9), 9.12 (bs, 1H).

Synthesis methyl 1-[(5-chloro-2-thienyl)sulfonyl-ethyl-amino]cyclopropanecarboxylate 17

A solution of 16 (2 g, 6.7 mmol) in DMF (20 mL) was added with an. K$_2$CO$_3$ (1.5 mol eq, 1.4 g) and, after few minutes, 2-iodoethane (1.2 mol eq, 0.84 ml) was added and the mixture was heated at 50° C. for 4 h. The solvent was removed under reduced pressure, water was added to the residue (100 mL) and the aqueous phase was extracted with EtOAc (3×50 mL). The combined organic phases were dried over Na$_2$SO$_4$ and evaporated under reduced pressure to afford 17 as a pale yellow oil (2.1 g, 95% yield). $^1$HNMR (DMSO, 200 MHz) δ 1.18 (m, 2H), 1.25 (t, 3H), 1.37 (m, 2H), 1.98 (s, 3H), 3.45 (m, 2H), 7.28 (d, 1H, J=4), 7.78 (d, 1H, J=3.9)

Synthesis of 1-[(5-chloro-2-thienyl)sulfonyl-ethyl-amino]cyclopropanecarboxylic acid 18

A solution of 17 (2.1 g, 6.5 mmol) in dioxane (20 mL) was added with 10% NaOH aq. solution (20 mL) and the mixture was heated at 50° C. overnight. The organic solvent was removed under reduced pressure and the aqueous phase was acidified with 10% HCl.

The solid formed was collected by filtration, washed with water (2×20 mL) and dried to afford 18 as a pale yellow solid (1.6 g, 85% yield). $^1$HNMR (DMSO, 200 MHz) δ 1.13 (t, 3H, J=7.4), 1.39 (bs, 4H), 3.36 (m, 2H), 7.25 (d, 2H, J=4.1), 7.52 (d, 2H, H=4)), 12.90 (bs, 1H).

Preparation of 1-[(5-chloro-2-thienyl)sulfonyl-ethyl-amino]-N-[[2-[4-(trifluoromethoxy)phenyl]-4-pyridyl]methyl]cyclopropanecarboxamide Example 28

A solution of acid 18 (0.50 g, 1.62 mmol) in THF (25 mL) was added with DEPC (0.32 mL, 1.3 mol eq) and the mixture was stirred at room temperature for 10'. Then [2-[4-(trifluoromethoxy)phenyl]-4-pyridyl]methanamine 21B (0.47 g, 1.1 mol eq) and a catalytic amount of TEA were added, then the reaction mixture was stirred at room temperature overnight. The solvent was removed under reduced pressure, water (40 mL) was added to the residue that was extracted with EtOAc (3×25 mL) and washed with brine (1×40 mL). The separated organic phase was dried over Na$_2$SO$_4$, evaporated to dryness and the residue was purified by flash chromatography (1:1 EtOAc:Petroleum ether) to afford a pale yellow oil (0.31 g). Yield=35%, $^1$HNMR (DMSO, 200 MHz) δ 1.22 (t, 3H), 1.40 (bs, 2H), 1.61 (bs, 2H), 4.16 (q, 2H), 4.42 (d, 2H, J=6.1), 7.26 (m, 2H), 7.46 (d, 2H, J=8), 7.6 (dd, 1H), 7.87 (s, 1H), 8.21 (d, 2H, J=7.9), 8.25 (t, 1H), 8.60 (d, 1H, J=4); [M$^{+1}$] 560.01 (C$_{23}$H$_{21}$ClF$_3$N$_3$O$_4$S$_2$ requires 559.06).

Example 29

1-[ethyl-(4-fluorophenyl)sulfonyl-amino]-N-[[3-[4-(trifluoromethyl)phenyl]phenyl]methyl]cyclopropanecarboxamide

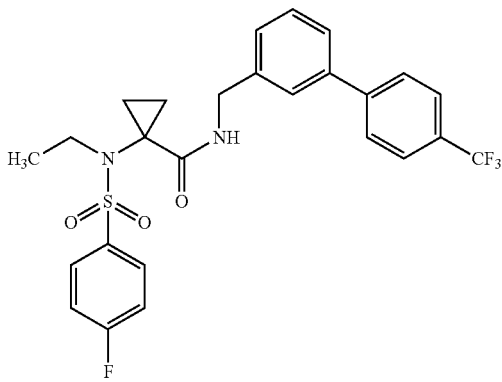 [SMILES: CCN(C1(C(=O)NCc2cccc(-c3ccc(C(F)(F)F)cc3)c2)CC1)S(=O)(=O)c1ccc(F)cc1]

Preparation of 1-[ethyl-(4-fluorophenyl)sulfonyl-amino]-N-[[3-[4-(trifluoromethyl)phenyl]phenyl]methyl]cyclopropanecarboxamide Example 29

A solution of acid 15A (0.30 g, 1.45 mmol) in THF (20 mL) was added with DEPC (0.21 mL, 1.3 mol eq) and the mixture was stirred at room temperature several minutes. Then [3-[4-(trifluoromethyl)phenyl]phenyl]methanamine 23A (0.29 g, 1.1 mol eq) and a catalytic amount of TEA were added, then the reaction mixture was stirred at room temperature overnight. The solvent was removed under reduced pressure, water was added to the residue that is extracted with EtOAc (3×25 mL) and washed with brine (1×40 mL). The separated organic phase was dried over $Na_2SO_4$, evaporated to dryness and the residue was purified by flash chromatography (7:3 EtOAc:Petroleum ether) to afford a white solid (0.13 g) after crystallization from ethyl ether. Yield=25%, $^1$HNMR (DMSO, 200 MHz) δ 1.055 (t, 2H), 1.17 (t, 3H, J=7), 1.28 (bs, 2H), 3.43 (q, 2H), 4.29 (d, 2H, J=6), 7.25 (d, 2H), 7.40 (m, 3H), 7.47 (m, 3H), 7.87-7.83 (m, 4H), 8.15 (t, 1H); [M$^{+1}$] 520.54 ($C_{26}H_{24}F_4N_2O_3S$ requires 520.14).

Example 30

1-[(4-chlorophenyl)sulfonyl-ethyl-amino]-N-[[3-[4-(trifluoromethyl)phenyl]phenyl]methyl]cyclopropanecarboxamide

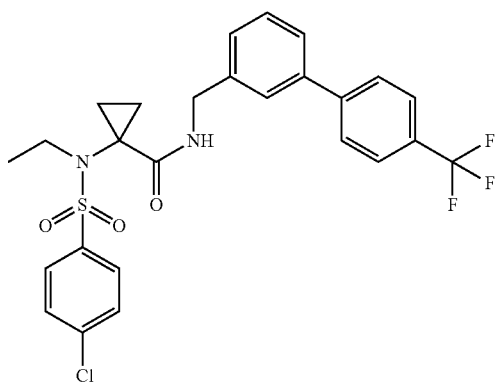 [SMILES: CCN(C1(C(=O)NCc2cccc(-c3ccc(C(F)(F)F)cc3)c2)CC1)S(=O)(=O)c1ccc(Cl)cc1]

Preparation of 1-[(4-chlorophenyl)sulfonyl-ethyl-amino]-N-[[3-[4-(trifluoromethyl)phenyl]phenyl]methyl]cyclopropanecarboxamide Example 30

Acid 15B (303 mg, 1 mmol) was dissolved in 5 ml of THF and at rt DEPC (1.1 equiv, 0.17 ml) and [3-[4-(trifluoromethyl)phenyl]phenyl]methanamine 23A (1.1 equiv., 276 mg) were added to the solution. The mixture was stirred at rt overnight then evaporated. The residue was dissolved in AcOEt (30 ml) and washed with water (1×20 ml) and brine. The organic phase was dried over sodium sulfate and concentrated under vacuum. The purification of the crude by chromatographic column (3:7 EtOAc:Petroleum ether) afforded 90 mg of a white solid. Yield=17% $^1$HNMR (DMSO, 200 MHz) δ 1.11 (2H, bm), 1.18 (3H, t, J=7 Hz), 1.38 (2H, bs), 3.40 (2H, bm), 4.38 (2H, d, J=5.8 Hz), 7.30 (1H, dd), 7.46 (1H, t, J=7.6 Hz), 7.64 (4H, m), 7.85 (6H, m), 7.90 (1H, bs), 8.10 (1H, t) [M$^{+1}$] 537.3 ($C_{26}H_{24}ClF_3N_2O_3S$ requires 536.99).

Example 31

1-[ethyl-(4-fluorophenyl)sulfonyl-amino]-N-[[3-[4-(trifluoromethoxy)phenyl]phenyl]methyl]cyclopropanecarboxamide

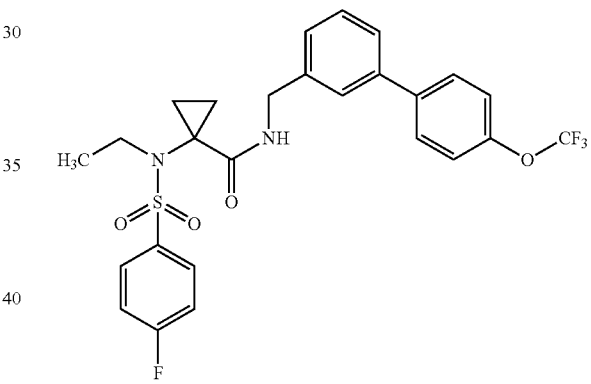

Preparation of 1-[ethyl-(4-fluorophenyl)sulfonyl-amino]-N-[[3-[4-(trifluoromethoxy)phenyl]phenyl]methyl]cyclopropanecarboxamide Example 31

A solution of acid 15A (0.30 g, 1.8 mmol) in THF (20 mL) was added with DEPC (0.21 mL, 1.3 mol eq) and the mixture was stirred at room temperature for 10 minutes. Then [3-[4-(trifluoromethoxy)phenyl]phenyl]methanamine 23B (0.308 g, 1.1 mol eq) and a catalytic amount of TEA were added, then the reaction mixture was stirred at room temperature overnight. The solvent was removed under reduced pressure, the residue was suspended in EtOAc (45 mL) and washed with water (50 mL) and brine. The separated organic phase was dried over an. $Na_2SO_4$ and evaporated under reduced pressure. The residue was purified by flash chromatography (1:1 EtOAc:Petroleum ether) to afford a white solid (0.15 g). Yield=28%, $^1$HNMR (DMSO, 200 MHz) δ 1.08 (m, 2H), 1.20 (t, 3H, J=8), 1.38 (bs, 2H), 3.42 (q, 2H), 4.38 (d, 2H, J=5.6), 7.27 (d, 1H, J=4), 7.46-7.39 (m, 6H), 7.55 (d, 1H), 7.59 (s, 1H), 7.78 (m, 2H), 7.87 (m, 2H), 8.08 (t, 1H). [M$^{+1}$] 536.54 ($C_{26}H_{24}F_4N_2O_4S$ requires 536.14).

Example 32

1-[(4-fluorophenyl)sulfonylamino]-N-[[2-pyrrolidin-1-yl-6-[4-(trifluoromethyl)phenyl]-4-pyridyl]methyl]cyclopropanecarboxamide

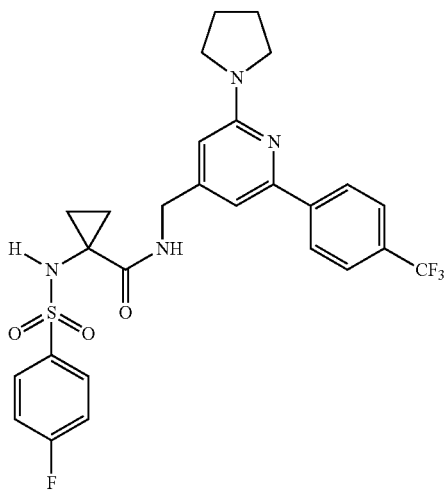 [SMILES: O=C(NCc1cc(-c2ccc(C(F)(F)F)cc2)nc(N2CCCC2)c1)C1(NS(=O)(=O)c2ccc(F)cc2)CC1]

Synthesis of 1-[(4-fluorophenyl)sulfonylamino]cyclopropanecarboxylic acid 15C Compound 13A (645 mg, 2.36 mmol) dissolved in THF (10 ml) and water (5 ml) was added with LiOH.H$_2$O (3 equiv., 297 mg) and the reaction was stirred at rt 3 hours. The reaction was concentrated under vacuum. Water was added and 10% HCl till precipitation of the acid. The acid was extracted with ethyl acetate and the organic phase was washed with Brine, dried over sodium sulfate and concentrated under vacuum to give 600 mg of 15C as a white solid. Yield=98%. $^1$HNMR (DMSO, 200 MHz) δ 1.38 (2H, m), 1.35 (2H, bs), 7.42 (2H, m), 7.80 (2H, m), 8.80 (1H, bs), 12.46 (1H, bs)

Preparation of 1-[(4-fluorophenyl)sulfonylamino]-N-[[2-pyrrolidin-1-yl-6-[4-(trifluoromethyl)phenyl]-4-pyridyl]methyl]cyclopropanecarboxamide Example 32

A solution of acid 15C (0.50 g, 1.75 mmol) in THF (25 mL) was added with DEPC (0.34 mL, 1.3 mol eq) and the mixture was stirred at room temperature for 5'. Then [2-pyrrolidin-1-yl-6-[4-(trifluoromethyl)phenyl]-4-pyridyl]methanamine 27A (0.61 g, 1.1 mol eq) and a catalytic amount of TEA were added, then the reaction mixture was stirred at room temperature overnight. The solvent was removed under reduced pressure, water (40 mL) was added to the residue that is extracted with EtOAc (3×25 mL) and washed with brine (1×40 mL). The separated organic phase was dried over Na$_2$SO$_4$, evaporated to dryness and the residue was purified by flash chromatography (1:1 EtOAc:Petroleum ether) to afford a pale orange solid (0.21 g) after crystallization from a mixture of ethyl ether/petroleum ether. Yield=22%, $^1$HNMR (DMSO, 200 MHz) δ 0.71 (m, 2H), 1.09 (m, 2H9, 1.96 (m, 4H), 3.38 (m, 4H), 4.18 (d, 2H, J=6.1), 6.33 (s, 1H), 6.46 (s, 1H), 7.47-7.38 (m, 4H), 7.88-7.80 (m, 4H), 8.37 (t, 1H), 8.71 (bs, 1H); [M$^{+1}$] 562.58 (C$_{27}$H$_{26}$F$_4$N$_4$O$_3$S requires 562.16).

Example 33

1-[(4-fluorophenyl)sulfonylamino]-N-[[2-pyrrolidin-1-yl-6-[4-(trifluoromethoxy)phenyl]-4-pyridyl]methyl]cyclopropanecarboxamide

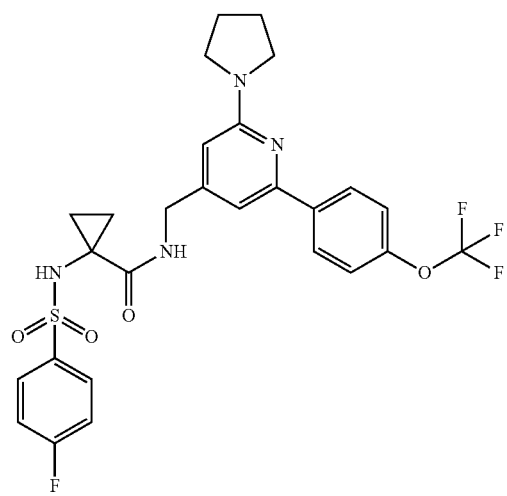 [SMILES: O=C(NCc1cc(-c2ccc(OC(F)(F)F)cc2)nc(N2CCCC2)c1)C1(NS(=O)(=O)c2ccc(F)cc2)CC1]

Preparation of 1-[(4-fluorophenyl)sulfonylamino]-N-[[2-pyrrolidin-1-yl-6-[4-(trifluoromethoxy)phenyl]-4-pyridyl]methyl]cyclopropanecarboxamide Example 33

Acid 15C (260 mg, 1 mmol) was dissolved in 5 ml of THF and at rt DEPC (1.1 equiv, 0.17 ml) and [2-pyrrolidin-1-yl-6-[4-(trifluoromethoxy)phenyl]-4-pyridyl]methanamine 27C (1.1 equiv., 371 mg) were added to the solution. The mixture was stirred at rt overnight then evaporated. The residue was dissolved in EtOAc (30 ml) and washed with water (1×20 ml) and brine. The organic phase was dried over sodium sulfate and concentrated under vacuum. The purification of the crude by chromatographic column (3:7 EtOAc:Petroleum ether) afforded 130 mg of a white solid. Yield=22% $^1$HNMR (DMSO, 200 MHz) δ 0.71 (2H, bm), 1.08 (2H, bm), 1.92 (4H, m), 3.47 (4H, m), 4.29 (2H, d, J=5.6 Hz), 6.41 (1H, s), 7.09 (1H, s), 7.45 (4H, m), 7.82 (2H, m), 8.17 (2H, d, J=9 Hz), 8.38 (1H, t), 8.71 (1H, bs) [M$^{+1}$] 579.4 (C$_{27}$H$_{26}$F$_4$N$_4$O$_4$S requires 578.58).

Example 34

1-[(5-chloro-2-thienyl)sulfonyl-ethyl-amino]-N-[[2-pyrrolidin-1-yl-6-[4-(trifluoromethyl)phenyl]-4-pyridyl]methyl]cyclopropanecarboxamide

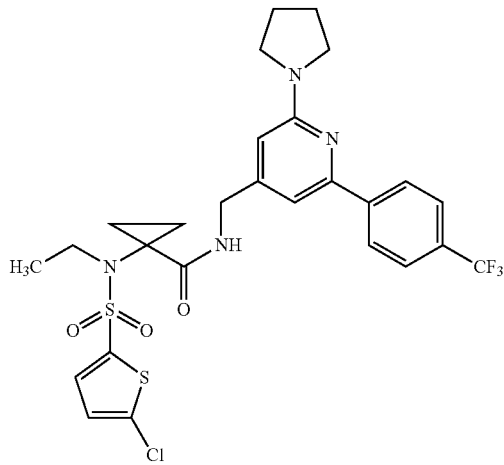 [SMILES: CCN(C1(C(=O)NCc2cc(-c3ccc(C(F)(F)F)cc3)nc(N3CCCC3)c2)CC1)S(=O)(=O)c1ccc(Cl)s1]

Preparation of 1-[(5-chloro-2-thienyl)sulfonyl-ethyl-amino]-N-[[2-pyrrolidin-1-yl-6-[4-(trifluoromethyl)phenyl]-4-pyridyl]methyl]cyclopropanecarboxamide Example 34

A solution of acid 18 (0.24 g, 0.76 mmol) in THF (20 mL) was added with DEPC (0.15 mL, 1.3 mol eq) and the mixture was stirred at room temperature for several minutes. Then [2-pyrrolidin-1-yl-6-[4-(trifluoromethyl)phenyl]-4-pyridyl]methanamine 27A (0.27 g, 1.1 mol eq) and a catalytic amount of TEA were added, then the reaction mixture was stirred at room temperature overnight. The solvent was removed under reduced pressure, the residue was suspended in EtOAc and washed with water (1×50 mL) and brine. After drying over $Na_2SO_4$, the separated organic phase was evaporated under reduced pressure and the residue was purified by flash chromatography (1:1 EtOAc:Petroleum ether) to afford a pale yellow solid (0.18 g) after crystallization from a mixture of ethyl ether/petroleum ether. Yield=38%, $^1$HNMR (DMSO, 200 MHz) δ 0.86 (t, 3H), 1.21 (m, 4H), 1.91 (m, 4H), 3.42 (m, 6H), 4.21 (d, 2H, J=6.2), 6.26 (s, 1H), 6.45 (s, 1H), 7.27 (d, 1H, J=4), 7.58 (d, 1H, J=3.8), 7.82 (d, 2H, J=7.8), 8.21 (d, 2H, J=8.1), 8.41 (t, 1H); [M$^{+1}$] 613.11 ($C_{27}H_{28}ClF_3N_4O_3S_2$ requires 612.12).

Example 35

2-[(3,4-difluorophenyl)sulfonyl-ethyl-amino]-N-[[2-[4-(trifluoromethyl)phenyl]-4-pyridyl]methyl]prop-2-enamide

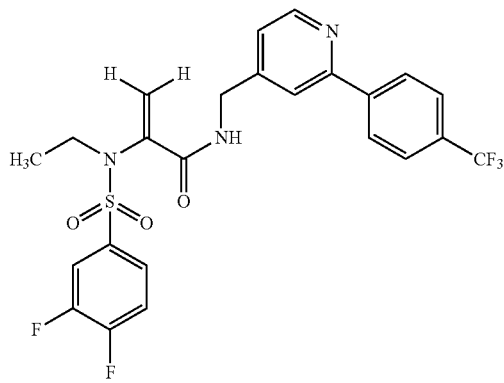 [SMILES: C=C(C(=O)NCc1ccnc(-c2ccc(C(F)(F)F)cc2)c1)N(CC)S(=O)(=O)c1ccc(F)c(F)c1]

Synthesis of methyl (2S)-2-[(3,4-difluorophenyl)sulfonylamino]-3-hydroxy-propanoate 2G A suspension of L-serine-methyl ester hydrochloride (1.5 g, 9.5 mmol) in $CH_2Cl_2$ (70 mL) was added with TEA (1.1 mol eq, 1.45 mL) and the mixture was stirred at r.t. for 10 minutes. Then 3,4-difluorobenzensulfonyl chloride (1 mol eq, 2.0 g) and additional TEA (1.1 mol eq) were added and the solution hated at 60° C. overnight. The solvent was removed under reduced pressure, water was added to the residue (100 mL) and the aqueous phase extracted with EtOAc (3×40 mL). The recombined organic phases were dried over $Na_2SO_4$ and evaporated to reduced pressure. The residue was recrystallized from ethylic ether to afford 2G as a pale orange solid (2.85 g, 94% yield). $^1$HNMR (DMSO, 200 MHz) δ 3.45 (s, 3H), 3.54 (m, 2H), 3.95 (m, 1H), 5.01 (t, 1H), 7.66 (m, 2H), 7.88 (m, 1H), 8.46 (d, 1H, J=8).

Synthesis of methyl (2S)-2-[(3,4-difluorophenyl)sulfonyl-ethyl-amino]-3-hydroxy-propanoate 3G A solution of 2G (2.85 g, 8.8 mmol) in DMF (20 mL) was added with an. $K_2CO_3$ (1.5 mol eq, 1.83 g) and, after few minutes, 2-iodoethane (1.2 mol eq, 1.09 mL) was added and the mixture heated at 50° C. for 12 h. The solvent was removed under reduced pressure, water was added to the residue (150 mL) and the aqueous phase extracted with EtOAc (3×60 mL). The recombined organic phases were dried over $Na_2SO_4$ and evaporated under reduced pressure to afford 3G as a pale yellow oil (2.8 g, 90% yield). $^1$HNMR (DMSO, 200 MHz) δ 1.15 (m, 3H), 1.98 (s, 3H), 3.08 (m, 2H), 4.04 (q, 2H, J=8), 4.58 (t, 1H), 5.15 (bm, 1H), 7.71 (m, 2H), 7.94 (m, 1H).

Synthesis of 2-[ethyl-(3,4-difluorophenyl)sulfonyl-amino]prop-2-enoic acid 4G

A solution of 3G (2.8 g, 7.9 mmol) in dioxane (30 mL) was added with 20% NaOH aq. solution (20 mL) and the mixture heated at 80° C. for 5 h. The organic solvent was removed under reduced pressure and the aqueous phase acidified with 10% HCl and extracted with $CH_2Cl_2$ (3×30 mL). The recombined organic phases were anhydrified using $Na_2SO_4$, evaporated under reduced pressure and then the resulting residue purified by flash chromatography (100% EtOAc) to obtain 4G as white solid (1 g, 44% yield). $^1$HNMR (DMSO, 200 MHz) δ 1.07 (t, 3H), 3.42 (q, 2H), 5.78 (s, 1H), 6.36 (s, 1H), 7.67 (m, 2H), 7.87 (m, 1H), 13.02 (bs, 1H).

Preparation of 2-[ethyl-(3,4-difluorophenyl)sulfonyl-amino]-N-[[2-[4-(trifluoromethyl)phenyl]-4-pyridyl]methyl]prop-2-enamide Example 35

Acid 4G (500 mg, 1.7 mmol) was dissolved in 20 ml of THF and at rt DEPC (1.3 equiv, 0.34 ml) and [2-[4-(trifluoromethyl)phenyl]-4-pyridyl]methanamine 21A (1.1 equiv., 476 mg) were added to the solution. The mixture was stirred at rt overnight then evaporated. The residue was dissolved in AcOEt (30 mL) and washed with water (1×20 mL) and brine. The organic phase was dried over sodium sulfate and concentrated under vacuum. The purification of the crude by chromatographic column (EtOAc 1/petroleum ether 1) afforded 120 mg of a white solid. Yield=24% $^1$HNMR (DMSO, 200 MHz) δ 1.09 (3H, t, J=7.2 Hz), 3.45 (2H, q, J=6.8 Hz), 4.51 (2H, d, J=6 Hz), 5.31 (1H, s), 6.17 (1H, s), 7.38 (1H, dd, J=4.8 Hz, J'=1.2 Hz), 7.68 (2H, t, J=8.8 Hz), 7.83 (2H, 3H), 8.02 (s, 1H), 8.32 (d, 2H, J=7.8), 8.67 (d, 1H, J=5.8), 8.93 (t, 1H). [M$^{+1}$] 525.11 ($C_{24}H_{20}F_5N_3O_3S$ requires 524.98).

Example 36

2-[(3-difluorophenyl)sulfonyl-ethyl-amino]-N-[[2-[4-(trifluoromethyl)phenyl]-4-pyridyl]methyl]prop-2-enamide

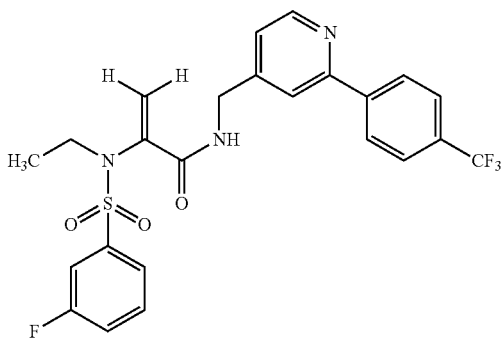 [SMILES: C=C(C(=O)NCc1ccnc(-c2ccc(C(F)(F)F)cc2)c1)N(CC)S(=O)(=O)c1cccc(F)c1]

Synthesis of methyl (2S)-2-[(3-fluorophenyl)sulfonylamino]-3-hydroxy-propanoate 2F A suspension of L-serine-methyl ester hydrochloride (1.6 g, 10.3 mmol) in $CH_2Cl_2$ (70 mL) was added with TEA (1.1 mol eq, 1.6 mL) and the mixture was stirred at r.t. for 10 minutes. Then 3-fluorobenzensulfonyl chloride (1 mol eq, 2.0 g) and additional TEA (1.1 mol eq) were added and the solution hated at 60° C. overnight. The solvent was removed under reduced pressure, water was added to the residue (100 mL) and the aqueous phase extracted with EtOAc (3×40 mL). The recombined organic phases were dried over $Na_2SO_4$ and evaporated to reduced pressure. The residue was recrystallized from ethylic ether to afford 2F as a pale yellow solid (2.80 g, 95% yield). $^1$HNMR (DMSO, 200 MHz) δ 3.41 (s, 3H), 3.48 (m, 2H), 4.01 (m, 1H), 5.20 (t, 1H), 7.58 (m, 2H), 7.81 (m, 2H), 8.52 (d, 1H, J=8).

Synthesis of methyl (2S)-2-[(3-fluorophenyl)sulfonyl-ethyl-amino]-3-hydroxy-propanoate 3F A solution of 2F (3.0 g, 10.8 mmol) in DMF (15 mL) was added with an. $K_2CO_3$ (1.5 mol eq, 2.24 g) and, after few minutes, 2-iodoethane (1.2 mol eq, 1.33 mL) was added and the mixture heated at 50° C. for 12 h. The solvent was removed under reduced pressure, water was added to the residue (150 mL) and the aqueous phase extracted with EtOAc (4×50 mL). The recombined organic phases were dried over $Na_2SO_4$ and evaporated under reduced pressure to afford 3F as a pale orange viscous oil (3.2 g, 95% yield). $^1$HNMR (DMSO, 200 MHz) δ 1.15 (m, 3H), 2.00 (s, 3H), 3.79 (q, 2H, J=8), 4.06 (t, 1H), 4.59 (t, 1H), 5.18 (m, 2H), 7.94 (m, 4H).

Synthesis of 2-[ethyl-(3-fluorophenyl)sulfonyl-amino]prop-2-enoic acid 4F

A solution of 3F (3.0 g, 9.8 mmol) in dioxane (30 mL) was added with 20% NaOH aq. solution (20 mL) and the mixture heated at 80° C. for 5 h. The organic solvent was removed under reduced pressure and the aqueous phase acidified with 10% HCl. The solid formed was filtered under vacuum, washed with cold water (1×50 mL) and dried to afford 4F as white solid (650 mg, 25% yield). $^1$HNMR (DMSO, 200 MHz) δ 1.11 (t, 3H, J=7.7), 3.43 (q, 2H), 5.78 (s, 1H), 6.36 (s, 1H), 7.69 (m, 2H), 7.84 (m, 2H), 12.98 (bs, 1H).

Preparation of 2-[ethyl-(3-fluorophenyl)sulfonyl-amino]-N-[[2-[4-(trifluoromethyl)phenyl]-4-pyridyl]methyl]prop-2-enamide Example 36

Acid 4F (330 mg, 1.2 mmol) was dissolved in 15 ml of THF and at rt DEPC (1.3 equiv, 0.23 mL) and [2-[4-(trifluoromethyl)phenyl]-4-pyridyl]methanamine 21A (1.1 mol equiv., 335 mg) were added to the solution. The mixture was stirred at rt overnight then evaporated. The residue was dissolved in AcOEt (30 mL) and washed with water (1×20 mL) and brine. The organic phase was dried over sodium sulfate and concentrated under vacuum. The purification of the crude by chromatographic column (EtOAc 1/petroleum ether 1) afforded 100 mg of a white solid. Yield=20% $^1$HNMR (DMSO, 200 MHz) δ 1.09 (3H, t, J=7.2 Hz), 3.44 (2H, q, J=6.8 Hz), 4.50 (2H, d, J=6 Hz), 5.21 (1H, s), 6.14 (1H, s), 7.34 (1H, dd, J=4.8), 7.65 (m, 4H), 7.81 (d, 2H, J=7.9), 8.01 (s, 1H), 8.31 (d, 2H, J=7.8), 8.65 (d, 1H, J=5.8), 8.92 (t, 1H). [M$^{+1}$] 507.62 ($C_{24}H_{21}F_4N_3O_3S$ requires 507.50).

Example 37

N-[[2-dimethylamino-6-[4-(trifluoromethyl)phenyl]-4-pyridyl]methyl]-2-[ethyl-(4-fluorophenyl)sulfonyl-amino]prop-2-enamide

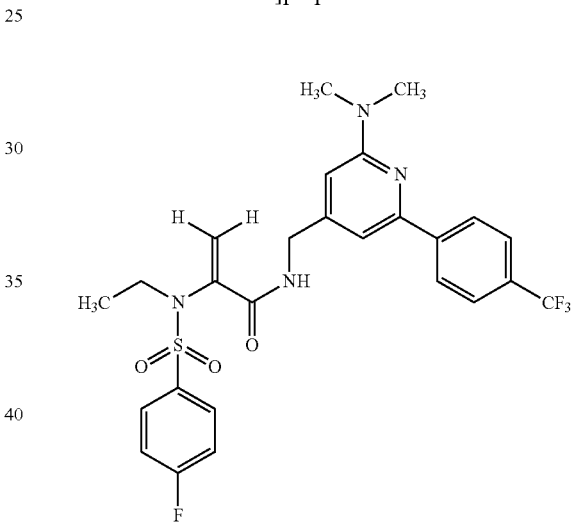

Synthesis of 2-chloro-6-(N,N'-dimethylamino)-pyridine-4-carbonitrile 25C

Compound 24 (1.5 g, 8.7 mmol) was added with hexamethylphosphoramide (1.56 mL, 1 mol eq) and the mixture was heated at 120° C. for 12 h. The reaction was cooled and then water was added (300 mL). The solid formed was collected by filtration and washed three times with water (3×30 mL) then dried to afford 25C as a pale yellow solid (1.28 g, 82% Yield). $^1$HNMR (DMSO, 200 MHz) δ 3.04 (s, 6H), 7.10 (s, 1H)), 8.23 (s, 1H).

Synthesis of 2-(N,N'-dimethylamino)-6-[4-(trifluoromethyl)phenyl]pyridine-4-carbonitrile 26E The nitrile 25C (2.0 g, 11.1 mmol), 4-trifluoromethylphenylboronic acid (2.32 g, 1.1 mol eq), palladium acetate (50 mg, 0.02 mol eq), cesium carbonate (7.23 g, 2 mol eq), and XPhos (210 mg, 0.04 mol eq) were mixed, placed under a nitrogen atmosphere and dioxane (10 mL) was added. The mixture was heated at 100° C. for 3 h. After cooling, the mixture was filtered through a celite pad, washed with dioxane (2×20 mL) and concentrated under reduced pressure. The residue was purified by flash chromatography (9.5/0.5 petroleum ether/EtOAc) to afford 26E as a pale yellow solid (2.2 g, 68% Yield). $^1$HNMR (DMSO, 200 MHz) δ 3.13 (s, 6H), 7.12 (s, 1H), 7.58 (s, 1H), 7.82 (d, 2H, J=7.7), 8.30 (d, 2H, J=7.8).

Synthesis of [2-(N,N'-dimethylamino)-6-[4-(trifluoromethyl)phenyl]-4-pyridyl]methanamine 27E A solution of nitrile 26E (2.2 g, 7.6 mmol) in diethyl ether (50 mL) was added in small amounts to a mixture of $LiAlH_4$ (0.58 g, 2 mol eq) in diethyl ether (50 mL) stirred at 0° C. After the addition was completed, the mixture was stirred at room temperature overnight. The excess of $LiAlH_4$ was destroyed at 0° C. by addition of small amount of water (30 mL), the solid formed was filtered off and the organic filtrate was separated, washed with brine (50 mL) and dried over $Na_2SO_4$. The organic phase was evaporated under reduced pressure to afford 27E as a pale yellow oil (2.13 g, 95% yield). $^1$HNMR (DMSO, 200 MHz) δ 3.08 (s, 6H), 3.97 (s, 2H), 6.66 (s, 1H), 7.24 (s, 1H), 7.77 (d, 2H, J=7.5), 8.24 (d, 2H, J=8).

Preparation of N-[[2-dimethylamino-6-[4-(trifluoromethyl)phenyl]-4-pyridyl]methyl]-2-[ethyl-(4-fluorophenyl)sulfonyl-amino]prop-2-enamide
Example 37

Acid 4B (830 mg, 3.0 mmol) was dissolved in 25 ml of THF and at rt, then DEPC (1.3 mol equiv, 0.59 mL) and [2-(N,N'-dimethylamino)-1-yl-6-[4-(trifluoromethyl)phenyl]-4-pyridyl]methanamine 27E (1.1 mol equiv., 970 mg) were added to the solution. The mixture was stirred at rt overnight then evaporated. Water was added to the residue (100 mL) and extracted with EtOAc (3×30 mL). The organic phases were dried over sodium sulfate and evaporated to dryness. The residue was purified by chromatographic column (8/2 EtOAc/petroleum ether) to afford 260 mg of a white solid. Yield=16% $^1$HNMR (DMSO, 400 MHz) δ 1.06 (t, 3H, J=7.7), 3.07 (s, 6H), 3.38 (q, 2H, J=7.6), 4.38 (d, 2H, J=8), 5.10 (s, 1H), 6.10 (s, 1H), 6.59 (s, 1H), 7.21 (s, 1H), 7.47 (m, 2H), 7.78 (d, 2H, J=7.6), 7.84 (m, 2H), 8.23 (d, 2H, J=8), 8.79 (t, 1H). [M$^{+1}$] 550.57 ($C_{26}H_{26}F_4N_4O_3S$ requires 550.81).

Example 38

2-[ethyl-(4-fluorophenyl)sulfonyl-amino]-N-[[2-pyrrolidin-1-yl-6-[4-(trifluoromethyl)phenyl]-4-pyridyl]methyl]prop-2-enamide

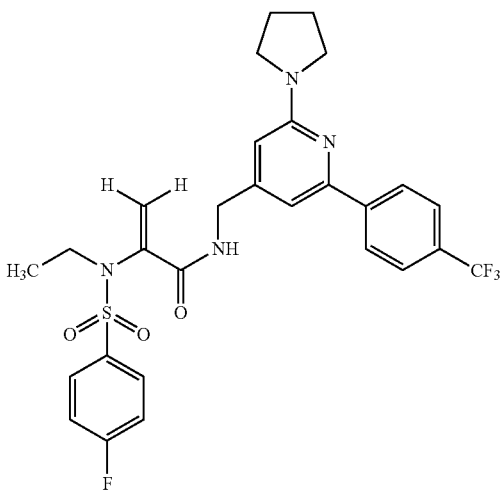 [SMILES: C=C(C(=O)NCc1cc(-c2ccc(C(F)(F)F)cc2)nc(N2CCCC2)c1)N(CC)S(=O)(=O)c1ccc(F)cc1]

Preparation of 2-[ethyl-(4-fluorophenyl)sulfonyl-amino]-N-[[2-pyrrolidin-1-yl-6-[4-(trifluoromethyl)phenyl]-4-pyridyl]methyl]prop-2-enamide
Example 38

A solution of acid 4B (0.15 g, 0.53 mmol) in THF (10 mL) was added with DEPC (0.10 mL, 1.3 mol eq) and the mixture was stirred at room temperature several minutes. Then [2-pyrrolidin-1-yl-6-[4-(trifluoromethyl)phenyl]-4-pyridyl]methanamine 27A (0.17 g, 1.1 mol eq) and a catalytic amount of TEA were added, then the reaction mixture was stirred at room temperature overnight. The solvent was removed under reduced pressure, water was added to the residue that is extracted with EtOAc (3×25 mL) and washed with brine (1×40 mL). The separated organic phase was dried over $Na_2SO_4$, evaporated to dryness and the residue was purified by flash chromatography (1/1 EtOAc/Petroleum ether) to afford a white solid (90 mg) after crystallization from ethyl ether. Yield=32%. $^1$HNMR (DMSO, 200 MHz) δ 1.092 (t, 3H, J=5.6), 1.95 (m, 4H), 3.4-3.46 (m, 6H), 4.39 (d, 2H, J=6), 5.13 (s, 1H), 6.12 (s, 1H), 6.47 (s, 1H), 7.20 (s, 1H), 7.51 (t, 2H, J=7.9), 7.80-7.90 (m, 4H), 8.27 (d, 2H, J=8.1), 8.78 (bt, 1H). [M$^{+1}$] 576.28 ($C_{28}H_{28}F_4N_4O_3S$ requires 576.60).

Example 39

2-[(5-chloro-2-thienyl)sulfonyl-ethyl-amino]-N-[[2-dimethylamino-6-[4-(trifluoromethyl)phenyl]-4-pyridyl]methyl]prop-2-enamide

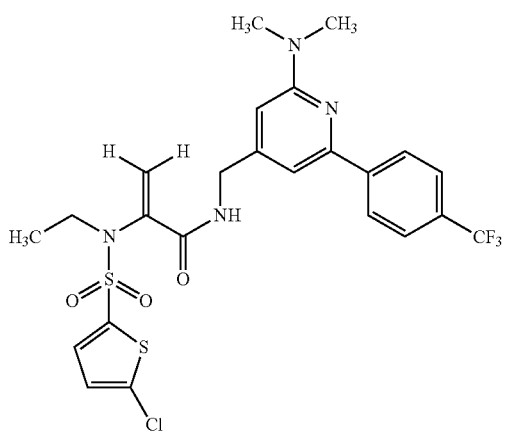 [SMILES: C=C(C(=O)NCc1cc(-c2ccc(C(F)(F)F)cc2)nc(N(C)C)c1)N(CC)S(=O)(=O)c1ccc(Cl)s1]

Preparation of 2-[(5-chloro-2-thienyl)sulfonyl-ethyl-amino]-N-[[2-dimethylamino-6-[4-(trifluoromethyl)phenyl]-4-pyridyl]methyl]prop-2-enamide
Example 39

A solution of acid 7I (0.16 g, 0.54 mmol) in THF (12 mL) was added was added DEPC (0.10 mL, 1.3 mol eq) and the mixture was stirred at room temperature several minutes. Then [2-(N,N'-dimethylamino)-6-[4-(trifluoromethyl)phenyl]-4-pyridyl]methanamine 27E (0.175 g, 1.1 mol eq) and a catalytic amount of TEA were added, then the reaction mixture was stirred at room temperature overnight. The solvent was removed under reduced pressure, water was added to the residue that is extracted with EtOAc (3×20 mL) and washed with brine (1×30 mL). The separated organic phase was dried over $Na_2SO_4$, evaporated to dryness and the residue was purified by flash chromatography (1/1 EtOAc/Petroleum ether) to afford a white solid (60 mg) after crystallization from ethyl ether. Yield=19%. ¹HNMR (DMSO, 200 MHz) δ 1.12 (t, 3H, J=7.2), 3.09 (s, 6H), 3.46 (m, 2H), 4.39 (d, 2H, J=6.5), 5.39 (s, 1H), 6.23 (s, 1H), 6.64 (s, 1H), 7.20 (s, 1H), 7.36 (d, 1H, J=4), 7.62 (d, 1H, J=3.9), 7.81 (d, 2H, J=7.8), 8.26 (d, 2H, J=7.9), 8.81 (bt, 1H). [M⁺¹] 572.85 ($C_{24}H_{24}ClF_3N_4O_3S_2$ requires 573.05).

Example 40

2-[ethyl-(4-fluorophenyl)sulfonyl-amino]-N-[[2-methoxy-6-[4-(trifluoromethyl)phenyl]-4-pyridyl]methyl]prop-2-enamide

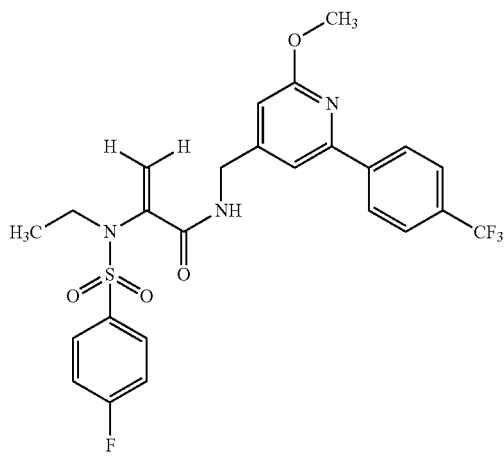 [SMILES: C=C(C(=O)NCc1cc(OC)nc(-c2ccc(C(F)(F)F)cc2)c1)N(CC)S(=O)(=O)c1ccc(F)cc1]

Synthesis of 2-chloro-6-methoxy-pyridine-4-carbonitrile 25F

A solution of compound 24 (2.0 g, 11.6 mmol) in methanol (20 mL) was added with sodium methoxyde (628 mg, 1 mol eq) and the mixture was heated at 60° C. for 6 h. The reaction was cooled, evaporated to dryness and then water was added (300 mL). The aqueous phase was extracted with EtOAc (3×25 mL) and the recombined organic phases were dried over sodium sulfate and evaporated under reduced pressure to afford 25F as transparent viscous oil (1.95 g, quantitative yield). ¹HNMR (DMSO, 200 MHz) δ 3.80 (s, 3H), 7.17 (s, 1H), 7.90 (s, 1H).

Synthesis of 2-methoxy-6-[4-(trifluoromethyl)phenyl]pyridine-4-carbonitrile 26I

The nitrile 25F (2.3 g, 13.8 mmol), 4-trifluoromethylphenylboronic acid (2.61 g, 1.1 mol eq), palladium acetate (62 mg, 0.02 mol eq), cesium carbonate (8.97 g, 2 mol eq) and XPhos (260 mg, 0.04 mol eq) were mixed, placed under a nitrogen atmosphere and dioxane (10 mL) was added. The mixture was heated at 100° C. for 4 h. After cooling, the mixture was filtered through a celite pad, washed with dioxane (2×30 mL) and concentrated under reduced pressure. The residue was purified by flash chromatography (9:1 petroleum ether:EtOAc) to afford 26I as a pale yellow solid (840 mg, 25% Yield). ¹HNMR (DMSO, 200 MHz) δ 4.03 (s, 3H), 7.46 (s, 1H), 7.90 (d, 2H, J=7.8), 8.17 (s, 1H), 8.40 (d, 2H, J=8).

Synthesis of [2-methoxy-6-[4-(trifluoromethyl)phenyl]-4-pyridyl]methanamine 27I

A solution of nitrile 26I (420 mg, 1.5 mmol) in diethyl ether (30 mL) was added in small amounts to a mixture of LiAlH₄ (115 mg, 2 mol eq) in diethyl ether (20 mL) stirred at 0° C. After the addition was completed, the mixture was stirred at room temperature overnight. The excess of LiAlH₄ was destroyed at 0° C. by addition of small amount of water (30 mL), the solid formed was filtered off and the organic filtrate was separated, washed with brine (50 mL) and dried over Na₂SO₄. The organic phase was evaporated under reduced pressure to afford 27I as a pale yellow oil (370 mg, 88% yield). ¹HNMR (DMSO, 200 MHz) δ 4.13 (s, 3H), 4.22 (s, 2H), 7.56 (s, 1H), 7.88 (d, 2H, J=7.8), 8.26 (s, 1H), 8.51 (d, 2H, J=8).

Preparation of 2-[ethyl-(4-fluorophenyl)sulfonyl-amino]-N-[[2-methoxy-6-[4-(trifluoromethyl)phenyl]-4-pyridyl]methyl]prop-2-enamide Example 40

A solution of acid 4B (0.31 g, 1.1 mmol) in THF (20 mL) was added with DEPC (0.22 mL, 1.3 mol eq) and the mixture was stirred at room temperature several minutes. Then [2-methoxy-6-[4-(trifluoromethyl)phenyl]-4-pyridyl]methanamine 27I (0.36 g, 1.1 mol eq) and a catalytic amount of TEA were added, then the reaction mixture was stirred at room temperature overnight. The solvent was removed under reduced pressure, water was added to the residue that is extracted with EtOAc (3×30 mL) and washed with brine (1×40 mL). The separated organic phase was dried over Na₂SO₄, evaporated to dryness and the residue was purified by flash chromatography (1/1 EtOAc/Petroleum ether) to afford a white solid (180 mg) after crystallization from ethyl ether. Yield=30%. ¹HNMR (DMSO, 200 MHz) δ 1.08 (t, 3H, J=6), 3.39 (m, 2H), 3.95 (s, 3H), 4.45 (d, 2H, J=6.2), 5.14 (s, 1H), 6.13 (s, 1H), 6.79 (s, 1H), 7.47 (t, 2H, J=8.2), 7.64 (s, 1H), 7.85 (m, 4H), 8.31 (d, 2H, J=7.8), 8.84 (bt, 1H). [M⁺¹] 537.05 ($C_{25}H_{23}F_4N_3O_4S$ requires 537.53).

Example 41

N-[[2-dimethylamino-6-[4-(trifluoromethyl)phenyl]-4-pyridyl]methyl]-2-(ethyl(2-thienylsulfonyl)amino)prop-2-enamide

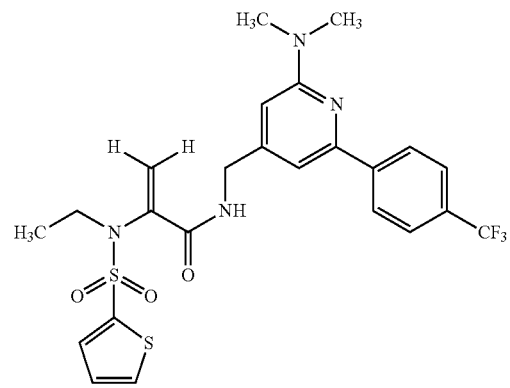 [SMILES: C=C(C(=O)NCc1cc(-c2ccc(C(F)(F)F)cc2)nc(N(C)C)c1)N(CC)S(=O)(=O)c1cccs1]

Synthesis of methyl (2S)-3-hydroxy-2-(2-thienylsulfonylamino)propanoate 5H

A suspension of L-serine-methyl ester hydrochloride (3.0 g, 19.3 mmol) in CH₂Cl₂ (80 mL) was added with TEA (1.1 mol eq, 2.9 mL) and the mixture was stirred at r.t. for 10 minutes. Then 2-thiophen-sulphonyl chloride (1 mol eq, 3.52 g) and additional TEA (1.1 mol eq) were added and the solution hated at 60° C. overnight. The solvent was removed under reduced pressure, water was added to the residue (100 mL) and the aqueous phase extracted with EtOAc (3×40 mL). The recombined organic phases were dried over Na$_2$SO$_4$ and evaporated under reduced pressure to afford 5H as white solid (4.9 g, 95% yield). $^1$HNMR (DMSO, 200 MHz) δ 3.61 (s, 2H), 3.82 (t, 2H, J=6.3), 4.14 (m, 1H), 4.62 (t, 1H), 5.25 (t, 1H), 7.21 (m, 1H), 7.75 (dd, 1H, J=2.1), 7.96 (dd, 1H, J=1.9), 8.23 (d, 1H).

Synthesis of methyl (2S)-2-(ethyl(2-thienylsulfonyl)amino)-3-hydroxy-propanoate 6H A solution of 5H (4.9 g, 18.6 mmol) in DMF (20 mL) was added with an. K$_2$CO$_3$ (1.5 mol eq, 3.85 g) and, after few minutes, 2-iodoethane (1.2 mol eq, 2.29 mL) was added and the mixture heated at 50° C. for 12 h. The solvent was removed under reduced pressure, water was added to the residue (150 mL) and the aqueous phase extracted with EtOAc (4×50 mL). The recombined organic phases were dried over Na$_2$SO$_4$ and evaporated under reduced pressure to afford 6H as a pale yellow oil (2.13 g, 44% yield). $^1$HNMR (DMSO, 200 MHz) δ 1.17 (t, 3H, J=6.2), 3.34 (q, 2H, J06.3), 3.49 (s, 2H), 3.76 (t, 2H, J=6.3), 4.04 (m, 1H), 4.50 (t, 1H), 5.18 (t, 1H), 7.18 (m, 1H), 7.65 (dd, 1H, J=2.1), 7.96 (dd, 1H, J=1.9).

Synthesis of 2-(ethyl(2-thienylsulfonyl)amino)prop-2-enoic acid 7H

A solution of 6H (2.13 g, 9.8 mmol) in dioxane (30 mL) was added with 20% NaOH aq. solution (20 mL) and the mixture heated at 80° C. for 5 h. The organic solvent was removed under reduced pressure and the aqueous phase acidified with 10% HCl. The solid formed was filtered under vacuum, washed with cold water (2×25 mL) and dried to afford 7H as white solid (135 mg, 42% yield). $^1$HNMR (DMSO, 200 MHz) δ 1.02 (t, 3H, J=7.7), 3.39 (q, 2H, J=6.3), 5.67 (s, 1H), 6.34 (s, 1H), 7.21 (m, 1H), 7.62 (dd, 1H, J=2.1), 8.00 (dd, 1H, J=1.9), 13.01 (bs, 1H).

Preparation of N-[[2-dimethylamino-6-[4-(trifluoromethyl)phenyl]-4-pyridyl]methyl]-2-(ethyl(2-thienylsulfonyl)amino)prop-2-enamide Example 41

A solution of acid 7H (0.30 g, 1.15 mmol) in THF (20 mL) was added with DEPC (0.23 mL, 1.3 mol eq) and the mixture was stirred at room temperature several minutes. Then [2-(N,N'-dimethylamino)-6-[4-(trifluoromethyl)phenyl]-4-pyridyl]methanamine 27E (0.371 g, 1.1 mol eq) and a catalytic amount of TEA were added, then the reaction mixture was stirred at room temperature overnight. The solvent was removed under reduced pressure, water was added to the residue that is extracted with EtOAc (3×30 mL) and washed with brine (1×40 mL). The separated organic phase was dried over Na$_2$SO$_4$, evaporated to dryness and the residue was purified by flash chromatography (6/4 EtOAc/Petroleum ether) to afford a white solid (0.22 g) after crystallization from ethyl ether. Yield=36%. $^1$HNMR (DMSO, 200 MHz) δ 1.12 (t, 3H, J=6), 3.09 (s, 6H), 3.44 (m, 2H), 4.40 (d, 2H, J=4.2), 5.15 (s, 1H), 6.21 (s, 1H), 6.66 (s, 1H), 7.27 (m, 2H), 7.68 (dd, 1H, J=1.8), 7.77 (d, 2H, J=7.9), 8.06 (dd, 1H, J=2.1), 8.27 (d, 2H, J=7.8), 8.78 (bt, 1H). [M$^{+1}$] 538.02 (C$_{24}$H$_{25}$F$_3$N$_4$O$_3$S$_2$ requires 538.60).

Example 42

2-[ethyl-(4-fluorophenyl)sulfonyl-amino]-N-[[2-morpholino-6-[4-(trifluoromethyl)phenyl]-4-pyridyl]methyl]prop-2-enamide

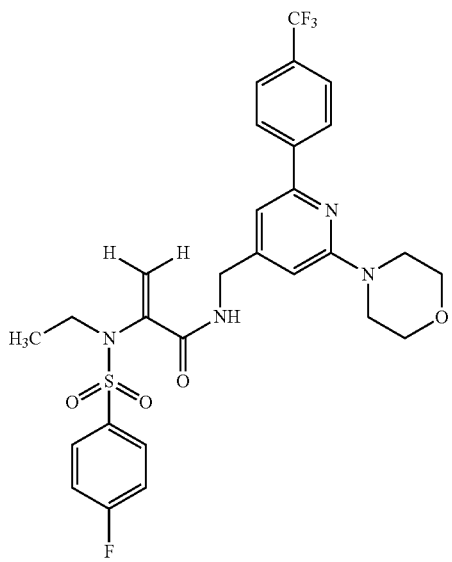 [SMILES: C=C(C(=O)NCc1cc(-c2ccc(C(F)(F)F)cc2)nc(N2CCOCC2)c1)N(CC)S(=O)(=O)c1ccc(F)cc1]

Synthesis of 2-morpholino-6-[4-(trifluoromethyl)phenyl]pyridine-4-carbonitrile 26B The nitrile 25B (3.2 g, 14.4 mmol), 4-trifluoromethylphenylboronic acid (3.01 g, 1 mol eq), palladium acetate (65 mg, 0.02 mol eq), cesium carbonate (9.38 g, 2 mol eq), and XPhos (265 mg, 0.04 mol eq) were mixed, placed under a nitrogen atmosphere and dioxane (12 mL) was added. The mixture was heated at 100° C. overnight. After cooling, the mixture was filtered through a celite pad, washed with dioxane (2×30 mL) and concentrated under reduced pressure. The residue was purified by flash chromatography (7/3 Petroleum ether/EtOAc) to afford 26B as yellow solid (1.33 g, 40% Yield). $^1$HNMR (DMSO, 400 MHz) δ 3.63 (m, 4H, J=1.9), 3.74 (m, 4H, J=2), 7.38 (s, 1H), 7.74 (s, 1H), 7.84 (d, 2H, J=8.1), 8.32 (d, 2H, J=8).

Synthesis of [2-morpholino-6-[4-(trifluoromethyl)phenyl]-4-pyridyl]methanamine 27B A solution of nitrile 26B (1.33 g, 4 mmol) in diethyl ether (30 mL) was added in small amounts to a mixture of LiAlH$_4$ (305 mg, 2 mol eq) in diethyl ether (20 mL) stirred at 0° C. After the addition was completed, the mixture was stirred at room temperature overnight. The excess of LiAlH$_4$ was destroyed at 0° C. by addition of small amount of water (30 mL), the solid formed was filtered off and the organic filtrate was separated, washed with brine (50 mL) and dried over Na$_2$SO$_4$. The organic phase was evaporated under reduced pressure to afford 27B as a pale yellow oil (1.34 g, quantitative yield). $^1$HNMR (DMSO, 200 MHz) δ 3.54 (m, 4H), 3.76 (m, 6H), 6.87 (s, 1H), 7.38 (s, 1H), 7.81 (d, 2H, J=8), 8.27 (d, 2H, J=7.9).

Preparation of 2-[ethyl-(4-fluorophenyl)sulfonyl-amino]-N-[[2-morpholino-6-[4-(trifluoromethyl)phenyl]-4-pyridyl]methyl]prop-2-enamide
Example 42

A solution of acid 4B (0.40 g, 1.46 mmol) in THF (20 mL) was added with DEPC (0.28 mL, 1.3 mol eq) and the mixture was stirred at room temperature several minutes. Then [2-morpholino-6-[4-(trifluoromethyl)phenyl]-4-pyridyl]methanamine 27B (530 mg, 1.1 mol eq) and a catalytic amount of TEA were added, then the reaction mixture was stirred at room temperature overnight. The solvent was removed under reduced pressure, water was added to the residue that is extracted with EtOAc (3×30 mL) and washed with brine (1×40 mL). The separated organic phase was dried over $Na_2SO_4$, evaporated to dryness and the residue was purified by flash chromatography (6/4 EtOAc/Petroleum ether) to afford a white solid (95 mg) after crystallization from ethyl ether. Yield=12%. $^1$HNMR (DMSO, 200 MHz) δ 1.087 (t, 3H, J=7.8), 3.39 (q, 2H, J=7.6), 3.55 (m, 4H), 3.71 (m, 4H), 4.42 (d, 2H, J=6.2), 5.13 (s, 1H), 6.12 (s, 1H), 6.85 (s, 1H), 7.35 (s, 1H), 7.47 (t, 2H, J=8), 7.83-7.90 (m, 4H), 8.26 (d, 2H, J=8), 8.80 (bt, 1H). $[M^{+1}]$ 592.33 ($C_{28}H_{28}F_4N_4O_4S$ requires 592.60).

Example 43

2-[(5-chloro-2-thienyl)sulfonyl-ethyl-amino]-N-[[2-morpholino-6-[4-(trifluoromethyl)phenyl]-4-pyridyl]methyl]prop-2-enamide

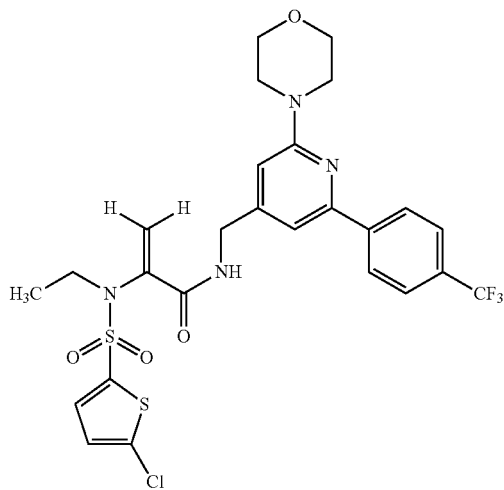 [SMILES: C=C(C(=O)NCc1cc(-c2ccc(C(F)(F)F)cc2)nc(N2CCOCC2)c1)N(CC)S(=O)(=O)c1ccc(Cl)s1]

Preparation of 2-[(5-chloro-2-thienyl)sulfonyl-ethyl-amino]-N-[[2-morpholino-6-[4-(trifluoromethyl)phenyl]-4-pyridyl]methyl]prop-2-enamide
Example 43

A solution of acid 7I (0.14 g, 0.47 mmol) in THF (15 mL) was added with DEPC (0.092 mL, 1.3 mol eq) and the mixture was stirred at room temperature several minutes. Then [2-morpholino-6-[4-(trifluoromethyl)phenyl]-4-pyridyl]methanamine 27B (0.175 g, 1.1 mol eq) and a catalytic amount of TEA were added, then the reaction mixture was stirred at room temperature overnight. The solvent was removed under reduced pressure, water was added to the residue that is extracted with EtOAc (3×20 mL) and washed with brine (1×30 mL). The separated organic phase was dried over $Na_2SO_4$, evaporated to dryness and the residue was purified by flash chromatography (1/1 EtOAc/Petroleum ether) to afford a white solid (90 mg) after crystallization from ethyl ether. Yield=32%. $^1$HNMR (DMSO, 200 MHz) δ 1.12 (t, 3H, J=7.2), 3.47 (m, 2H), 3.54 (m, 4H), 3.72 (m, 4H), 4.41 (d, 2H, J=6.2), 5.39 (s, 1H), 6.23 (s, 1H), 6.81 (s, 1H), 7.34 (m, 2H), 7.60 (d, 1H, J=4), 7.81 (d, 2H, J=8.1), 8.25 (d, 2H, J=8.2), 8.82 (t, 1H). $[M^{+1}]$ 614.98 ($C_{26}H_{26}ClF_3N_4O_4S_2$ requires 615.09).

Example 44

2-[ethyl-(4-fluorophenyl)sulfonyl-amino]-N-[[2-isopropoxy-6-[4-(trifluoromethyl)phenyl]-4-pyridyl]methyl]prop-2-enamide

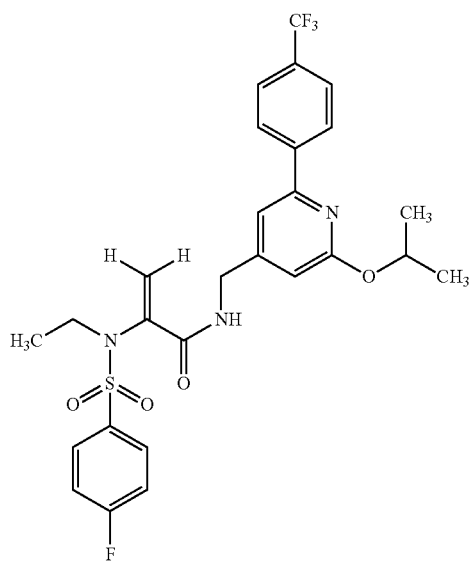 [SMILES: C=C(C(=O)NCc1cc(OC(C)C)nc(-c2ccc(C(F)(F)F)cc2)c1)N(CC)S(=O)(=O)c1ccc(F)cc1]

Synthesis of 2-chloro-6-isopropoxy-pyridine-4-carbonitrile 25H

A mixture of NaH 60% (05 g, 1.1 mol eq) in 2-isopropanol (15 mL) cooled at 0° C., was added in small portions with the nitrile 24 (2 g, 11.6 mmol). The reaction mixture was then heated at 60° C. for 5 h. Water was added (30 ml) and the aqueous phase was extracted with EtOAc (3×20 mL). The recombined organic phases were dried over sodium sulfate and evaporated under reduced pressure to afford 25H as a pale yellow viscous oil (1.82 g, 80% Yield).
$^1$HNMR (DMSO, 200 MHz) δ 1.31 (d, 6H, J=4), 5.18 (m, 1\H), 6.71 (s, 1H), 7.36 (s, 1H).

Synthesis of 2-isopropoxy-6-[4-(trifluoromethyl)phenyl]pyridine-4-carbonitrile 26M The nitrile 25H (1.25 g, 6.4 mmol), 4-trifluoromethylphenylboronic acid (1.34 g, 1 mol eq), palladium acetate (29 mg, 0.02 mol eq), cesium carbonate (4.16 g, 2 mol eq), and XPhos (137 mg, 0.04 mol eq) were mixed, placed under a nitrogen atmosphere and dioxane (8 mL) was added. The mixture was heated at 100° C. for 4 h. After cooling, the mixture was filtered through a celite pad, washed with dioxane (2×30 mL) and concentrated under reduced pressure. The residue was purified by flash chromatography (9.5/0.5 Petroleum ether/EtOAc) to afford 26M as yellow solid (0.65 g, 36% Yield).
$^1$HNMR (DMSO, 200 MHz) δ 1.37 (d, 6H, J=3.9), 5.15 (m, 1H), 6.7 (s, 1H), 7.32 (s, 1H), 7.87 (d, 2H, J=7.8), 8.33 (d, 2H, J=8).

Synthesis of [2-isopropoxy-6-[4-(trifluoromethyl)phenyl]-4-pyridyl]methanamine 27M A solution of nitrile 26M (0.65 g, 2.14 mmol) in diethyl ether (30 mL) was added in small amounts to a mixture of $LiAlH_4$ (163 mg, 2 mol eq) in diethyl ether (20 mL) stirred at 0° C. After the addition was completed, the mixture was stirred at room temperature overnight. The excess of $LiAlH_4$ was destroyed at 0° C. by addition of small amount of water (30 mL), the solid formed was filtered off and the organic filtrate was separated, washed with brine (40 mL) and dried over $Na_2SO_4$. The organic phase was evaporated under reduced pressure to afford 27M as a yellow oil (0.56 g, 86% yield). $^1$HNMR (DMSO, 400 MHz) δ 1.28 (d, 6H, J=5.8), 3.74 (s, 2H), 5.41 (m, 1H), 6.21 (s, 1H), 6.75 (s, 1H), 7.84 (d, 2H, J=7.8), 8.27 (d, 2H, J=8).

Preparation of 2-[ethyl-(4-fluorophenyl)sulfonyl-amino]-N-[[2-isopropoxy-6-[4-(trifluoromethyl)phenyl]-4-pyridyl]methyl]prop-2-enamide Example 44

A solution of acid 4B (300 g, 1.09 mmol) in THF (15 mL) was added with DEPC (0.21 mL, 1.3 mol eq) and the mixture was stirred at room temperature several minutes. Then [2-isopropoxy-6-[4-(trifluoromethyl)phenyl]-4-pyridyl]methanamine 27M (370 mg, 1.1 mol eq) and a catalytic amount of TEA were added, then the reaction mixture was stirred at room temperature overnight. The solvent was removed under reduced pressure, water was added to the residue that is extracted with EtOAc (3×30 mL) and washed with brine (1×40 mL). The separated organic phase was dried over $Na_2SO_4$, evaporated to dryness and the residue was purified by flash chromatography (3/7 EtOAc/Petroleum ether) to afford a white solid (100 mg) after crystallization from ethyl ether. Yield=18%. $^1$HNMR (DMSO, 400 MHz) δ 1.08 (t, 3H, J=7.4), 1.26 (d, 6H, J=6.2), 3.39 (q, 2H), 4.40 (d, 2H, J=7.9), 5.13 (s, 1H), 5.39 (m, 1H), 6.12 (s, 1H), 6.65 (s, 1H), 7.42 (t, 3H, J=4), 7.56 (s, 1H), 7.86 (m, 4H), 8.23 (d, 2H, J=8), 8.79 (t, 1H). [M$^{+1}$] 565.02 ($C_{27}H_{27}F_4N_3O_4S$ requires 565.58).

Example 45

N-[[2-dimethylamino-6-[4-(trifluoromethyl)phenyl]-4-pyridyl]methyl]-1-[ethyl-(4-fluorophenyl)sulfonyl-amino]cyclopropanecarboxamide

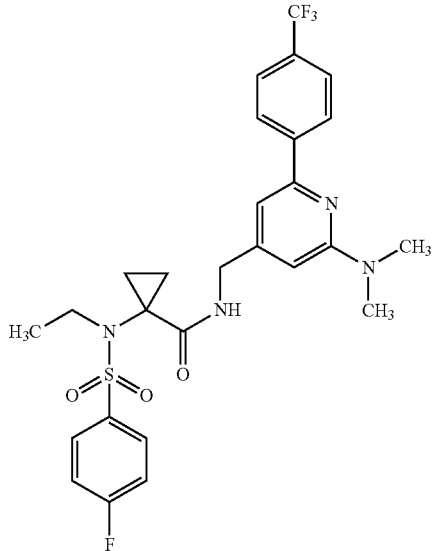 [SMILES: CCN(C1(C(=O)NCc2cc(-c3ccc(C(F)(F)F)cc3)nc(N(C)C)c2)CC1)S(=O)(=O)c1ccc(F)cc1]

Preparation of N-[[2-dimethylamino-6-[4-(trifluoromethyl)phenyl]-4-pyridyl]methyl]-1-[ethyl-(4-fluorophenyl)sulfonyl-amino]cyclopropanecarboxamide Example 45

Acid 15B (400 mg, 1.4 mmol) was dissolved in 20 ml of THF and at rt, then DEPC (1.3 mol equiv, 0.27 mL) and [2-(N,N'-dimethylamino)-6-[4-(trifluoromethyl)phenyl]-4-pyridyl]methanamine 27E (1.1 mol equiv., 450 mg) were added to the solution. The mixture was stirred at rt overnight then evaporated. Water was added to the residue (80 mL) and extracted with EtOAc (3×30 mL). The organic phases were dried over sodium sulfate and evaporated to dryness. The residue was purified by chromatographic column (8/2 EtOAc/petroleum ether) to afford 220 mg of a white solid. Yield=28%. $^1$HNMR (DMSO, 200 MHz) δ 1.08 (bs, 2H), 1.22 (t, 3H, J=8.1), 1.26 (bs, 2H), 3.11 (s, 6H), 3.42 (m, 2H), 4.36 (bd, 2H), 6.63 (s, 1H), 7.2 (s, 1H), 7.42 (t, 2H, J=10), 7.88 (m, 4H), 8.27 (m, 3H). [M$^{+1}$] 564.59 ($C_{27}H_{28}F_4N_4O_3S$ requires 564.29).

Example 46

1-[(5-chloro-2-thienyl)sulfonyl-ethyl-amino]-N-[[2-[4-(trifluoromethyl)phenyl]-4-pyridyl]methyl]cyclopropanecarboxamide

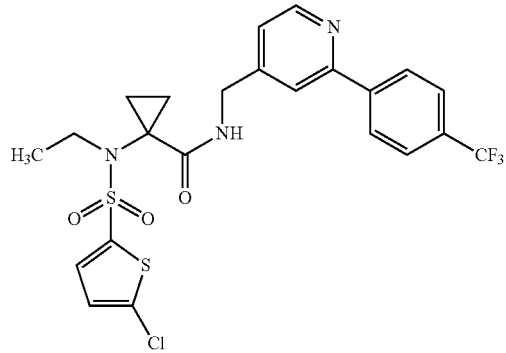 [SMILES: CCN(C1(C(=O)NCc2ccnc(-c3ccc(C(F)(F)F)cc3)c2)CC1)S(=O)(=O)c1ccc(Cl)s1]

Preparation of 1-[(5-chloro-2-thienyl)sulfonyl-ethyl-amino]-N-[[2-[4-(trifluoromethyl)phenyl]-4-pyridyl]methyl]cyclopropanecarboxamide Example 46

Acid 18 (0.3 g, 1.09 mmol) was dissolved in 15 ml of THF and at rt DEPC (1.3 equiv, 0.21 mL) and [2-[4-(trifluoromethyl)phenyl]-4-pyridyl]methanamine 21A (1.1 mol equiv., 0.37 g) were added to the solution. The mixture was stirred at rt overnight then evaporated. The residue was dissolved in AcOEt (30 mL) and washed with water (1×20 mL) and brine. The organic phase was dried over sodium sulfate and concentrated under vacuum. The purification of the crude by chromatographic column (EtOAc 3/petroleum ether 7) afforded 100 mg of a white solid. Yield=18% $^1$HNMR (DMSO, 200 MHz) δ 1.24 (m, 5H), 1.35 (m, 2H), 3.45 (m, 2H), 4.44 (d, 2H, J=6.2), 7.26 (m, 3H), 6.61 (d, 1H, J=2.1), 7.88 (d, 2H, J=7.8), 7.94 (s, 1H), 8.31 (d, 3H, J=8), 8.64 (d, 1H, J=4.1). [M$^{+1}$] 543.95 ($C_{23}H_{21}ClF_3N_3O_3S_2$ requires 544.01).

Example 47

1-[(5-chloro-2-thienyl)sulfonyl-ethyl-amino]-N-[[3-[4-(trifluoromethoxy)phenyl]phenyl]methyl]cyclopropanecarboxamide

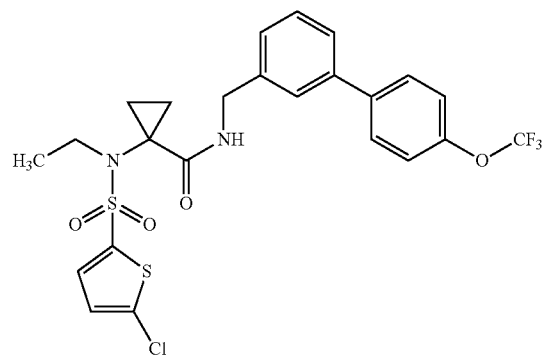 [SMILES: CCN(C1(C(=O)NCc2cccc(-c3ccc(OC(F)(F)F)cc3)c2)CC1)S(=O)(=O)c1ccc(Cl)s1]

Preparation of 1-[(5-chloro-2-thienyl)sulfonyl-ethyl-amino]-N-[[3-[4-(trifluoromethoxy)phenyl]phenyl]methyl]cyclopropanecarboxamide Example 47

A solution of acid 18 (0.20 g, 0.65 mmol) in THF (15 mL) was added with DEPC (0.13 mL, 1.3 mol eq) and the mixture was stirred at room temperature for 10 minutes. Then [3-[4-(trifluoromethoxy)phenyl]phenyl]methanamine 23B (0.19 g, 1.1 mol eq) and a catalytic amount of TEA were added, then the reaction mixture was stirred at room temperature overnight. The solvent was removed under reduced pressure, the residue was suspended in EtOAc (45 mL) and washed with water (40 mL) and brine. The separated organic phase was dried over an. $Na_2SO_4$ and evaporated under reduced pressure. The residue was purified by flash chromatography (1/1 EtOAc/Petroleum ether) to afford a white solid (0.2 g). Yield=59%, $^1$HNMR (DMSO, 200 MHz) δ 1.23 (m, 5H), 1.41 (m, 2H), 3.36 (m, 2H), 4.39 (d, 2H, J=6.1), 7.25 (m, 2H), 7.45 (m, 4H), 7.57 (m, 2H), 7.79 (d, 2H, J=7.9), 8.09 (t, 1H). [M$^{+1}$] 559.31 ($C_{24}H_{22}ClF_3N_2O_4S_2$ requires 559.02).

Example 48

1-[ethyl-(4-fluorophenyl)sulfonyl-amino]-N-[[2-methoxy-6-[4-(trifluoromethyl)phenyl]-4-pyridyl]methyl]cyclopropanecarboxamide

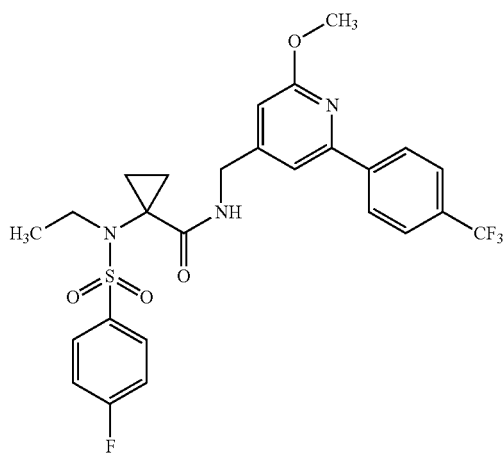 [SMILES: CCN(C1(C(=O)NCc2cc(OC)nc(-c3ccc(C(F)(F)F)cc3)c2)CC1)S(=O)(=O)c1ccc(F)cc1]

Preparation of 1-[ethyl-(4-fluorophenyl)sulfonyl-amino]-N-[[2-methoxy-6-[4-(trifluoromethyl)phenyl]-4-pyridyl]methyl]cyclopropanecarboxamide Example 48

A solution of acid 15B (0.2 g, 0.69 mmol) in THF (20 mL) was added with DEPC (0.135 mL, 1.3 mol eq) and the mixture was stirred at room temperature several minutes. Then [2-methoxy-6-[4-(trifluoromethyl)phenyl]-4-pyridyl]methanamine 27I (0.214 g, 1.1 mol eq) and a catalytic amount of TEA were added, then the reaction mixture was stirred at room temperature overnight. The solvent was removed under reduced pressure, water was added to the residue that is extracted with EtOAc (3×30 mL) and washed with brine (1×40 mL). The separated organic phase was dried over $Na_2SO_4$, evaporated to dryness and the residue was purified by flash chromatography (1/1 EtOAc/Petroleum ether) to afford a white solid (170 mg) after crystallization from ethyl ether. Yield=49%. $^1$HNMR (DMSO, 200 MHz) δ 1.08 (m, 2H), 1.22 (t, 3H, J=6.5), 1.25 (m, 2H), 3.42 (m, 2H), 3.96 (s, 3H), 4.39 (d, 2H, J=6.2), 6.75 (s, 1H), 7.41 (t, 2H, J=7.8), 7.61 (s, 1H), 7.91 (m, 4H), 8.32 (m, 3H). [M$^{+1}$] 551.65 ($C_{26}H_{25}F_4N_3O_4S$ requires 551.55).

Example 49

1-[ethyl-(4-fluorophenyl)sulfonyl-amino]-N-[[2-isopropoxy-6-[4-(trifluoromethyl)phenyl]-4-pyridyl]methyl]cyclopropanecarboxamide

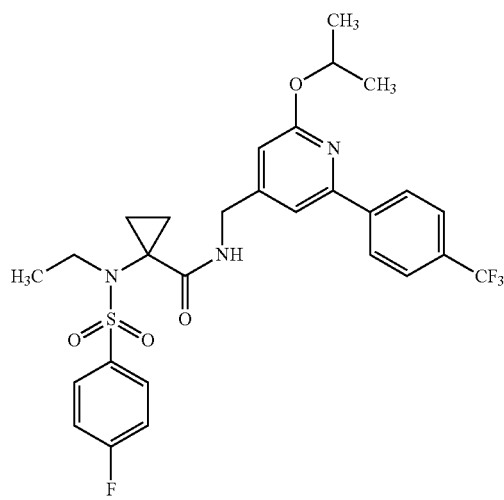 [SMILES: CCN(C1(C(=O)NCc2cc(OC(C)C)nc(-c3ccc(C(F)(F)F)cc3)c2)CC1)S(=O)(=O)c1ccc(F)cc1]

Preparation of 1-[ethyl-(4-fluorophenyl)sulfonyl-amino]-N-[[2-isopropoxy-6-[4-(trifluoromethyl)phenyl]-4-pyridyl]methyl]cyclopropanecarboxamide Example 49

A solution of acid 15B (0.16 g, 0.55 mmol) in THF (15 mL) was added with DEPC (0.11 mL, 1.3 mol eq) and the mixture was stirred at room temperature several minutes. Then [2-isopropoxy-6-[4-(trifluoromethyl)phenyl]-4-pyridyl]methanamine 27M (0.19 g, 1.1 mol eq) and a catalytic amount of TEA were added, then the reaction mixture was stirred at room temperature overnight. The solvent was removed under reduced pressure, water was added to the residue that is extracted with EtOAc (3×30 mL) and washed with brine (1×40 mL). The separated organic phase was dried over $Na_2SO_4$, evaporated to dryness and the residue was purified by flash chromatography (1/1 EtOAc/Petroleum ether) to afford a pale yellow solid (100 mg) after crystallization from ethyl ether. Yield=31%. $^1$HNMR (DMSO, 200 MHz) δ 0.83 (m, 3H), 1.12 (m, 4H), 1.36 (d, 6H, J=6.1), 3.43 (m, 2H), 4.37 (d, 2H, J=6), 5.40 (m, 1H), 6.64 (s, 1H), 7.41 (t, 2H), 7.56 (s, 1H), 7.89 (m, 4H), 8.27 (m, 3H) [M$^{+1}$] 579.88 ($C_{28}H_{29}F_4N_3O_4S$ requires 579.61).

Example 50

1-[(5-chloro-2-thienyl)sulfonyl-ethyl-amino]-N-[[2-methoxy-6-[4-(trifluoromethyl)phenyl]-4-pyridyl]methyl] cyclopropanecarboxamide

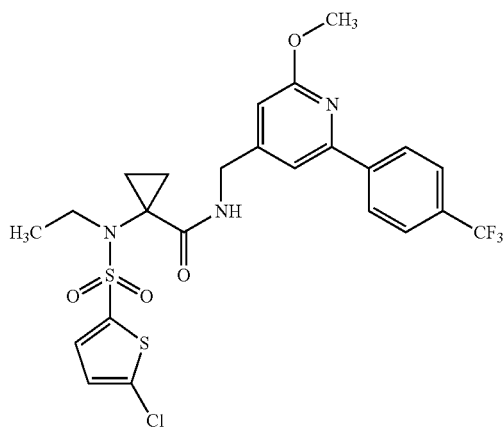 [SMILES: CCN(C1(C(=O)NCc2cc(OC)nc(-c3ccc(C(F)(F)F)cc3)c2)CC1)S(=O)(=O)c1ccc(Cl)s1]

Preparation of 1-[(5-chloro-2-thienyl)sulfonyl-ethyl-amino]-N-[[2-methoxy-6-[4-(trifluoromethyl)phenyl]-4-pyridyl]methyl]cyclopropanecarboxamide
Example 50

A solution of acid 18 (0.3 g, 0.97 mmol) in THF (15 mL) was added with DEPC (0.19 mL, 1.3 mol eq) and the mixture was stirred at room temperature several minutes. Then [2-methoxy-6-[4-(trifluoromethyl)phenyl]-4-pyridyl]methanamine 27I (0.22 g, 1.1 mol eq) and a catalytic amount of TEA were added, then the reaction mixture was stirred at room temperature overnight. The solvent was removed under reduced pressure, water was added to the residue that is extracted with EtOAc (3×30 mL) and washed with brine (1×30 mL). The separated organic phase was dried over $Na_2SO_4$, evaporated to dryness and the residue was purified by flash chromatography (1/1 EtOAc/Petroleum ether) to afford a white solid (110 mg) after crystallization from ethyl ether. Yield=26%. $^1$HNMR (DMSO, 400 MHz) δ 1.21 (t, 5H, J=6.2), 1.41 (m, 2H), 3.54 (m, 2H), 3.94 (s, 3H), 4.18 (bs, 2H), 6.70 (s, 1H), 7.25 (d, 1H, J=2.1), 7.57 (d, 2H, J=2.3), 7.84 (d, 2H, J=8), 8.27 (m, 3H). [M$^{+1}$] 574.66 ($C_{24}H_{23}ClF_3N_3O_4S_2$ requires 574.04).

Example 51

1-[ethyl-(4-fluorophenyl)sulfonyl-amino]-N-[[2-pyrrolidin-1-yl-6-[4-(trifluoromethyl)phenyl]-4-pyridyl]methyl]cyclopropanecarboxamide

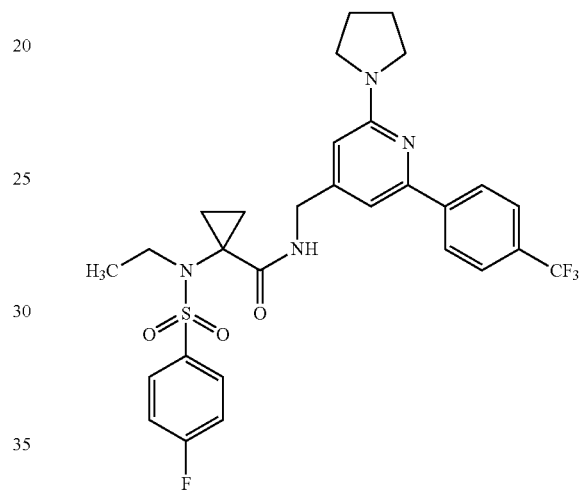

Preparation of 1[ethyl-(4-fluorophenyl)sulfonyl-amino]-N-[[2-pyrrolidin-1-yl-6-[4-(trifluoromethyl)phenyl]-4-pyridyl]methyl]cyclopropanecarboxamide
Example 51

A solution of acid 15B (0.3 g, 1.04 mmol) in THF (15 mL) was added with DEPC (0.20 mL, 1.3 mol eq) and the mixture was stirred at room temperature several minutes. Then [2-pyrrolidin-1-yl-6-[4-(trifluoromethyl)phenyl]-4-pyridyl]methanamine 27A (0.36 g, 1.1 mol eq) and a catalytic amount of TEA were added, then the reaction mixture was stirred at room temperature overnight. The solvent was removed under reduced pressure, water was added to the residue that is extracted with EtOAc (3×35 mL) and washed with brine (1×40 mL). The separated organic phase was dried over $Na_2SO_4$, evaporated to dryness and the residue was purified by flash chromatography (4/6 EtOAc/Petroleum ether) to afford a white solid (105 mg) after crystallization from ethyl ether. Yield=18%. $^1$HNMR (DMSO, 200 MHz) δ 1.08 (m, 2H), 1.22 (t, 3H, J=6), 1.26 (m, 2H), 1.96 (m, 4H), 3.47 (m, 6H), 4.34 (d, 2H, J=6.3), 6.43 (s, 1H), 7.17 (s, 1H), 7.46 (t, 2H, J=8), 7.86 (m, 4H), 8.20 (t, 1H), 8.27 (d, 2H, J=8). [M$^{+1}$] 590.11 ($C_{29}H_{30}F_4N_4O_3S$ requires 590.63).

Example 52

N-[[2-ethoxy-6-[4-(trifluoromethyl)phenyl]-4-pyridyl]methyl]-1-[ethyl-(4-fluorophenyl)sulfonyl-amino]cyclopropanecarboxamide

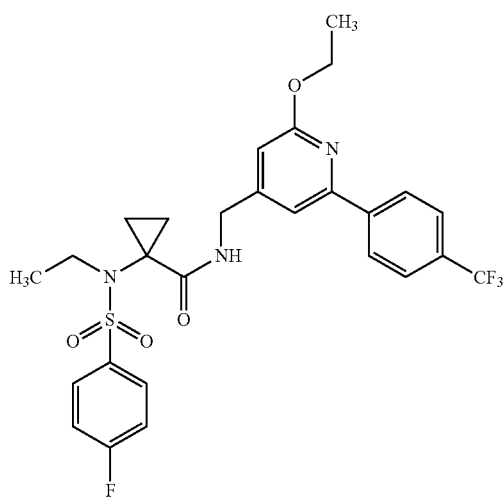 [SMILES: CCOc1cc(CNC(=O)C2(N(CC)S(=O)(=O)c3ccc(F)cc3)CC2)cc(-c2ccc(C(F)(F)F)cc2)n1]

Synthesis of 2-chloro-6-[4-(trifluoromethyl)phenyl]pyridine-4-carbonitrile 25G A solution of compound 24 (2.5 g, 14.5 mmol) in abs. ethanol (30 mL) was added with sodium ethoxyde (1.08 mg, 1.1 mol eq) and the mixture was heated at 60° C. overnight. The reaction was cooled, evaporated to dryness and then water was added (300 mL). The aqueous phase was extracted with EtOAc (3×35 mL) and the recombined organic phases were dried over sodium sulfate and evaporated under reduced pressure to afford 25G as a pale yellow oil (1.1 g, 45% Yield). $^1$HNMR (DMSO, 200 MHz) δ 1.23 (t, 3H, J=6.2), 4.24 (q, 2H, J=6.3), 7.07 (s, 1H), 7.38 (s, 1H).

Synthesis of 2-ethoxy-6-[4-(trifluoromethyl)phenyl]pyridine-4-carbonitrile 26 L The nitrile 25G (1.1 g, 6.07 mmol), 4-trifluoromethylphenylboronic acid (1.15 g, 1 mol eq), palladium acetate (27 mg, 0.02 mol eq), cesium carbonate (3.95 g, 2 mol eq), and XPhos (116 mg, 0.04 mol eq) were mixed, placed under a nitrogen atmosphere and dioxane (7 mL) was added. The mixture was heated at 100° C. for 3 h. After cooling, the mixture was filtered through a celite pad, washed with dioxane (2×30 mL) and concentrated under reduced pressure. The residue was purified by flash chromatography (9.5/0.5 petroleum ether/EtOAc) to afford 26L as a pale yellow solid (620 mg, 40% Yield). $^1$HNMR (DMSO, 200 MHz) δ 1.38 (t, 3H, J=6.2), 4.5 (q, 2H, J=6.3), 7.40 (s, 1H), 7.89 (d, 2H, J=8), 8.14 (s, 1H), 8.36 (d, 2H, H=8).

Synthesis of [2-ethoxy-6-[4-(trifluoromethyl)phenyl]-4-pyridyl]methanamine 27L A solution of nitrile 26L (620 mg, 2.1 mmol) in diethyl ether (20 mL) was added in small amounts to a mixture of LiAlH$_4$ (162 mg, 2 mol eq) in diethyl ether (20 mL) stirred at 0° C. After the addition was completed, the mixture was stirred at room temperature overnight. The excess of LiAlH$_4$ was destroyed at 0° C. by addition of small amount of water (30 mL), the solid formed was filtered off and the organic filtrate was separated, washed with brine (50 mL) and dried over Na$_2$SO$_4$. The organic phase was evaporated under reduced pressure to afford 27L as a pale yellow oil (650 mg, quantitative yield). $^1$HNMR (DMSO, 200 MHz) δ 1.34 (t, 3H, J=6.2), 3.30 (bs, 2H), 4.44 (q, 2H, J=6.3), 6.80 (s, 1H), 7.64 (s, 1H), 7.85 (d, 2H, J=7.8), 8.30 (d, 2H, J=8).

Preparation of N-[[2-ethoxy-6-[4-(trifluoromethyl)phenyl]-4-pyridyl]methyl]-1-[ethyl-(4-fluorophenyl)sulfonyl-amino]cyclopropanecarboxamide Example 52

A solution of acid 15B (260 mg, 0.91 mmol) in THF (20 mL) was added with DEPC (0.18 mL, 1.3 mol eq) and the mixture was stirred at room temperature several minutes. Then [2-ethoxy-6-[4-(trifluoromethyl)phenyl]-4-pyridyl]methanamine 27L (300 mg, 1.1 mol eq) and a catalytic amount of TEA were added, then the reaction mixture was stirred at room temperature overnight. The solvent was removed under reduced pressure, water was added to the residue that is extracted with EtOAc (3×35 mL) and washed with brine (1×40 mL). The separated organic phase was dried over Na$_2$SO$_4$, evaporated to dryness and the residue was purified by flash chromatography (4/6 EtOAc/Petroleum ether) to afford a white solid (120 mg) after crystallization from ethyl ether. Yield=23%. $^1$HNMR (DMSO, 200 MHz) δ 1.05 (t, 4H), 1.25 (t, 3H, J=6.3), 1.40 (t, 4H), 3.39 (m, 2H), 4.45 (m, 4H), 6.7 (s, 1H), 7.42 (t, 2H), 7.59 (s, 1H), 7.86 (m, 3H), 8.25 (m, 3H). [M$^{+1}$] 565.42 (C$_{27}$H$_{27}$F$_4$N$_3$O$_4$S requires 565.58).

Example 53

1-[(5-chloro-2-thienyl)sulfonyl-ethyl-amino]-N-[[2-ethoxy-6-[4-(trifluoromethyl)phenyl]-4-pyridyl]methyl] cyclopropanecarboxamide

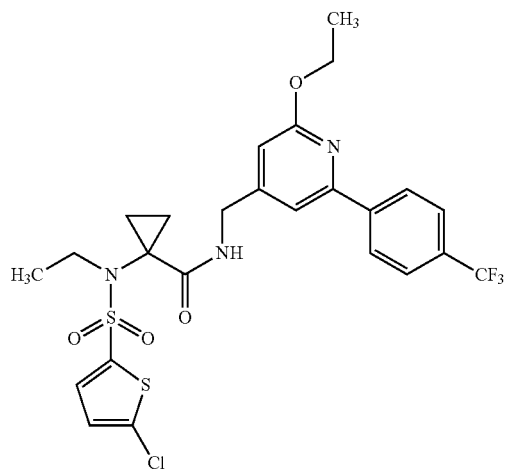 [SMILES: CCOc1cc(CNC(=O)C2(N(CC)S(=O)(=O)c3ccc(Cl)s3)CC2)cc(-c2ccc(C(F)(F)F)cc2)n1]

Synthesis of 1-[(5-chloro-2-thienyl)sulfonyl-ethyl-amino]-N-[[2-methoxy-6-[4-(trifluoromethyl)phenyl]-4-pyridyl]methyl]cyclopropanecarboxamide
Example 53

A solution of acid 18 (281 mg, 0.90 mmol) in THF (20 mL) was added with DEPC (0.18 mL, 1.3 mol eq) and the mixture was stirred at room temperature several minutes. Then [2-ethoxy-6-[4-(trifluoromethyl)phenyl]-4-pyridyl]methanamine 27L (300 mg, 1.1 mol eq) and a catalytic amount of TEA were added, then the reaction mixture was stirred at room temperature overnight. The solvent was removed under reduced pressure, water was added to the residue that is extracted with EtOAc (3×35 mL) and washed with brine (1×40 mL). The separated organic phase was dried over $Na_2SO_4$, evaporated to dryness and the residue was purified by flash chromatography (4/6 EtOAc/Petroleum ether) to afford a white solid (130 mg) after crystallization from ethyl ether. Yield=25%. $^1$HNMR (DMSO, 200 MHz) δ 1.23 (m, 4H), 1.4 (m, 6H), 3.41 (m, 2H), 4.41 (m, 4H), 6.67 (s, 1H), 7.27 (d, 1H, J=3.8), 7.58 (m, 2H), 7.86 (d, 2H, J=8), 8.28 (m, 3H). $[M^{+1}]$ 587.80 ($C_{25}H_{25}ClF_3N_3O_4S_2$ requires 588.06).

Example 54

2-[ethyl-(4-fluorophenyl)sulfonyl-amino]-N-[[1-oxido-2-[4-(trifluoromethyl)phenyl]pyridin-1-ium-4-yl]methyl]prop-2-enamide

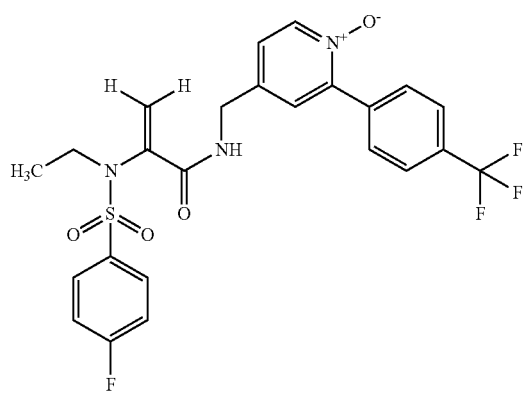 [SMILES: C=C(C(=O)NCc1cc[n+]([O-])c(-c2ccc(C(F)(F)F)cc2)c1)N(CC)S(=O)(=O)c1ccc(F)cc1]

Preparation of 2-[ethyl-(4-fluorophenyl)sulfonyl-amino]N-[[1-oxido-2-[4-(trifluoromethyl)phenyl]pyridin-1-ium-4-yl]methyl]prop-2-enamide
Example 54

3-Chloro perbenzoic acid (1.5 mol eq, 100 mg) was added to a solution of Example 1 (200 mg, 0.39 mmol) in $CHCl_3$ (10 mL) and the mixture was stirred at r.t. for 24 hours. Then 10% water solution of $K_2CO_3$ was added to wash the organic phase that was then dried over $Na_2SO_4$ and evaporated under reduced pressure. The resulting residue was purified by flash chromatography (EtOAc 6/petroleum ether 4) to obtain a white solid (60 mg, 29% yield). $^1$HNMR (DMSO, 200 MHz) δ 1.09 (3H, t, J=7.2 Hz), 3.40 (2H, q, J=6.8 Hz), 4.40 (2H, d, J=6 Hz), 5.14 (1H, s), 6.10 (1H, s), 7.36 (1H, dd, J=4.8 Hz, J'=1.2 Hz), 7.46 (2H, t, J=8.8 Hz), 7.63 (1H, d, J=2.2 Hz), 7.83 (4H, m), 8.05 (2H, d, J=8 Hz), 8.34 (1H, d, J=6.8 Hz), 8.82 (1H, bt) $[M^{+1}]$ 524.6 ($C_{24}H_{21}F_4N_3O_4S$ requires 523.50).

Example 55

2-[(5-chloro-2-thienyl)sulfonyl-ethyl-amino]-N-[[3-[4-(trifluoromethoxy)phenyl]phenyl]methyl]prop-2-enamide

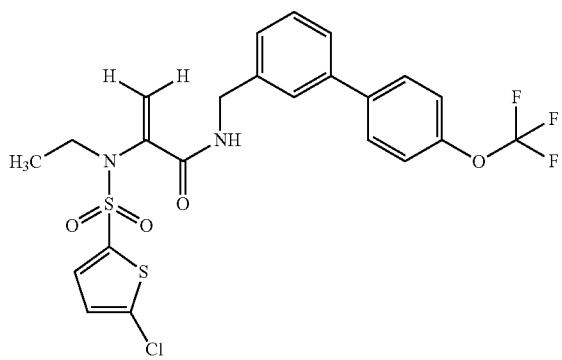 [SMILES: C=C(C(=O)NCc1cccc(-c2ccc(OC(F)(F)F)cc2)c1)N(CC)S(=O)(=O)c1ccc(Cl)s1]

Preparation of 2-[(5-chloro-2-thienyl)sulfonyl-ethyl-amino]N-[[3-[4-(trifluoromethoxy)phenyl]phenyl]methyl]prop-2-enamide Example 55

Acid 7I (665 mg, 2 mmol) was dissolved in 10 ml of THF and at rt DEPC (1.1 equiv, 0.3 ml) and [4-(trifluoromethoxy)phenyl]phenyl]methanamine 23B (1.1 equiv., 590 mg) were added to the solution. The mixture was stirred at rt overnight then evaporated. The residue was dissolved in AcOEt (30 ml) and washed with water (1×20 ml) and brine. The organic phase was dried over sodium sulfate and concentrated under vacuum. The purification of the crude by chromatographic column (4:6 EtOAc:petroleum ether) afforded 200 mg of a pale yellow solid. Yield=18.3% $^1$HNMR (DMSO, 200 MHz) δ 1.09 (3H, t, J=7 Hz), 3.44 (2H, q, J=7.2 Hz), 4.43 (2H, d, J=6 Hz), 5.40 (1H, s), 6.19 (1H, s), 7.33 (2H, m), 7.44 (3H, m), 7.60 (3H, m), 7.75 (2H, dd, J=8.8 Hz, J'=2.2 Hz), 8.80 (1H, bt) $[M^{+1}]$ 545.1 ($C_{23}H_{20}ClF_3N_2O_4S_2$ requires 544.99).

Example 56

2-[(4-fluorophenyl)sulfonyl-methyl-amino]-N-[[2-[4-(trifluoromethyl)phenyl]-4-pyridyl]methyl]prop-2-enamide

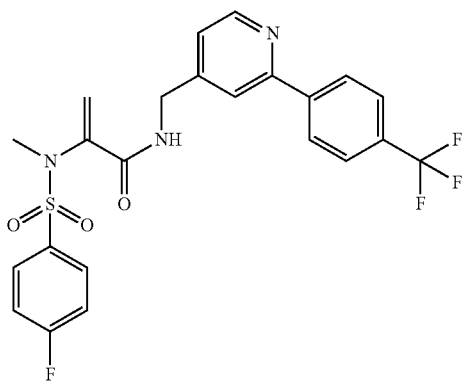 [SMILES: C=C(C(=O)NCc1ccnc(-c2ccc(C(F)(F)F)cc2)c1)N(C)S(=O)(=O)c1ccc(F)cc1]

Preparation of 2-[(4-fluorophenyl)sulfonyl-methyl-amino]-N-[[2-[4-(trifluoromethyl)phenyl]-4-pyridyl]methyl]prop-2-enamide Example 56

A solution of acid 4A (260 mg, 1 mmol) in THF (25 mL) was added with DEPC (0.18 mL, 1.3 mol eq) and the mixture was stirred at room temperature for about 5 minutes. Then [2-[4-(trifluoromethyl)phenyl]-4-pyridyl]methanamine 21A (1.1 equiv., 277.5 mg) was added. The reaction mixture was then stirred at room temperature overnight. The solvent was removed under reduced pressure, the residue was suspended in EtOAc (30 mL) and washed with water (50 mL) and brine. The separated organic phase, after anhydrification over $Na_2SO_4$, was evaporated under reduced pressure and the residue was purified by flash chromatography (1:1 EtOAc:Petroleum ether) to afford a pale yellow solid (100 mg) after crystallization from a mixture of diethyl ether/petroleum ether. Yield=49%, $^1$HNMR (DMSO, 400 MHz) δ 2.93 (3H, s), 4.48 (d, 2H, J=6 Hz), 5.08 (s, 1H), 5.87 (s, 1H), 7.35 (d, 1H), 7.37 (t, 2H, J=8.8 Hz), 7.82 (m, 4H), 8.03 (s, 1H), 8.28 (d, 2H, J=8.4 Hz), 8.63 (d, 1H, J=5.2 Hz), 8.95 (bt, 1H); [M$^{+1}$] 494.47 ($C_{23}H_{19}F_4N_3O_3S$ requires 493.47).

Example 57

1-[(4-fluorophenyl)sulfonyl-methyl-amino]-N-[[3-[4-(trifluoromethoxy)phenyl]phenyl]methyl]cyclopropanecarboxamide

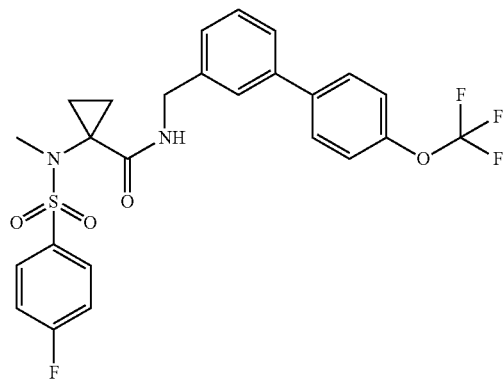 [SMILES: CN(C1(C(=O)NCc2cccc(-c3ccc(OC(F)(F)F)cc3)c2)CC1)S(=O)(=O)c1ccc(F)cc1]

Synthesis of methyl 1-[methyl-(4-fluorophenyl)sulfonyl-amino]cyclopropanecarboxylate 14A A solution of 13A (1 g, 3.67 mmol) in DMF (15 mL) was added with an. $K_2CO_3$ (1.5 mol eq, 0.76 g) and, after few minutes, 2-iodomethane (1.2 mol eq, 0.81 ml) was added and the mixture was heated at 50° C. for 12 h. The solvent was removed under reduced pressure, water was added to the residue (60 mL) and the aqueous phase was extracted with EtOAc (3×30 mL). The recombined organic phases were dried over $Na_2SO_4$ and evaporated under reduced pressure to afford 14A as a pale yellow oil (950 mg, 90% yield). $^1$HNMR (DMSO, 200 MHz) δ 2.43 (bs, 4H), 2.88 (s, 3H), 2.90 (s, 3H), 7.42 (t, 2H, J=8.2), 7.87 (m, 2H).

Synthesis of 1-[methyl-(4-fluorophenyl)sulfonyl-amino]cyclopropanecarboxylic acid 15A A solution of 14A (1.3 g, 4.52 mmol) in dioxane (40 mL) was added with 10% NaOH aq. solution (20 mL) and the mixture was heated at 50° C. overnight. The organic solvent was removed under reduced pressure and the aqueous phase was acidified with 10% HCl. The solid formed was collected by filtration, washed with water (2×20 mL) and dried to afford 15A as white solid (1.0 g, 81% yield). $^1$HNMR (DMSO, 200 MHz) δ 1.40 (bs, 4H), 2.91 (s, 3H), 7.42 (m, 2H), 7.80 (m, 2H), 12.60 (bs, 1H).

Preparation of 1-[(4-fluorophenyl)sulfonyl-methyl-amino]-N-[[3-[4-(trifluoromethoxy)phenyl]phenyl]methyl]cyclopropanecarboxamide Example 57

Acid 15A (350 mg, 1.28 mmol) was dissolved in 5 ml of THF and at rt DEPC (0.25 mL, 1.3 mol eq) and [3-[4-(trifluoromethoxy)phenyl]phenyl]methanamine 23B (0.376 g, 1.1 mol eq) were added to the solution. The mixture was stirred at rt overnight then evaporated. he residue was dissolved in AcOEt (30 ml) and washed with water (1×20 ml) and brine. The organic phase was dried over sodium sulfate and concentrated under vacuum. The purification of the crude by chromatographic column (3:7 EtOAc:Petroleum ether) afforded 100 mg of a white solid. Yield=15% $^1$HNMR (DMSO, 200 MHz) δ 1.09 (2H, bs), 1.34 (2H, bs), 3.00 (3H, s), 4.35 (2H, d, J=5.8 Hz), 7.43 (8H, m), 7.81 (4H, m), 8.17 (1H, bt); [M$^{+1}$] 523.9 ($C_{25}H_{22}F_4N_2O_4S$ requires 522.51).

Example 58

1-[(4-fluorophenyl)sulfonyl-methyl-amino]-N-[[3-[4-(trifluoromethyl)phenyl]phenyl]methyl]cyclopropanecarboxamide

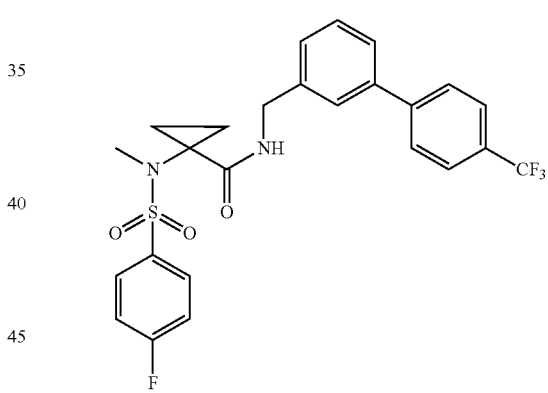

Preparation of 1-[(4-fluorophenyl)sulfonyl-methyl-amino]-N-[[3-[4-(trifluoromethyl)phenyl]phenyl]methyl]cyclopropanecarboxamide Example 58

Acid 15A (820 mg, 3 mmol) was dissolved in 5 ml of THF and at rt DEPC (1.1 equiv, 0.5 ml) and [3-[4-(trifluoromethyl)phenyl]phenyl]methanamine 23A (1.1 equiv., 835 mg) were added to the solution. The mixture was stirred at rt overnight then evaporated. he residue was dissolved in AcOEt (30 ml) and washed with water (1×20 ml) and brine. The organic phase was dried over sodium sulfate and concentrated under vacuum. The purification of the crude by chromatographic column (3:7 EtOAc:Petroleum ether) afforded 250 mg of a white solid. Yield=16.5% $^1$HNMR (DMSO, 400 MHz) δ 1.09 (2H, bs), 1.32 (2H, bs), 2.99 (3H, s), 4.34 (2H, d, J=5.8 Hz), 7.35 (4H, m), 7.58 (2H, m), 7.80 (4H, m), 7.87 (2H, d, J=8 Hz), 8.18 (1H, bt); [M$^{+1}$] 507.9 ($C_{25}H_{22}F_4N_2O_3S$ requires 506.51).

Example 59

1-[(5-chloro-2-thienyl)sulfonyl-ethyl-amino]-N-[[3-[4-(trifluoromethyl)phenyl]phenyl]methyl]cyclopropanecarboxamide

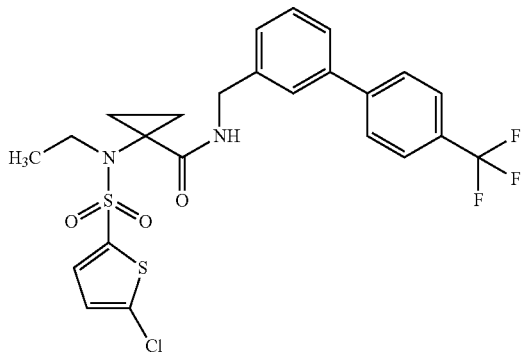 [SMILES: CCN(C1(C(=O)NCc2cccc(-c3ccc(C(F)(F)F)cc3)c2)CC1)S(=O)(=O)c1ccc(Cl)s1]

Preparation of 1-[(5-chloro-2-thienyl)sulfonyl-ethyl-amino]-N-[[3-[4-(trifluoromethyl)phenyl]phenyl]methyl]cyclopropanecarboxamide Example 59

A solution of acid 18 (0.50 g, 1.62 mmol) in THF (25 mL) was added with DEPC (0.32 mL, 1.3 mol eq) and the mixture was stirred at room temperature for 10'. [3-[4-(trifluoromethyl)phenyl]phenyl]methanamine 23A (1.1 equiv., 450 mg) was added to the solution. The mixture was stirred at rt overnight then evaporated. he residue was dissolved in AcOEt (30 ml) and washed with water (1×20 ml) and brine. The organic phase was dried over sodium sulfate and concentrated under vacuum. The purification of the crude by chromatographic column (3:7 EtOAc:Petroleum ether) afforded 350 mg of a white solid. Yield=40% $^1$HNMR (DMSO, 200 MHz) δ 1.19 (5H, m), 1.41 (2H, bs), 3.39 (2H, m), 4.38 (2H, d, J=5.8 Hz), 7.23 (1H, dd, J=4 Hz), 7.33 (1H, d), 7.41 (1H, t), 7.50 (3H, m), 7.79 (4H, dd, J=5.8 Hz), 8.11 (1H, bs); [M$^{+1}$] 544.9 ($C_{24}H_{22}ClF_3N_2O_3S_2$ requires 543.02).

Example 60

1-[ethyl-(4-fluorophenyl)sulfonyl-amino]-N-[[4-[4-(trifluoromethyl)phenyl]-2-pyridyl]methyl]cyclopropanecarboxamide

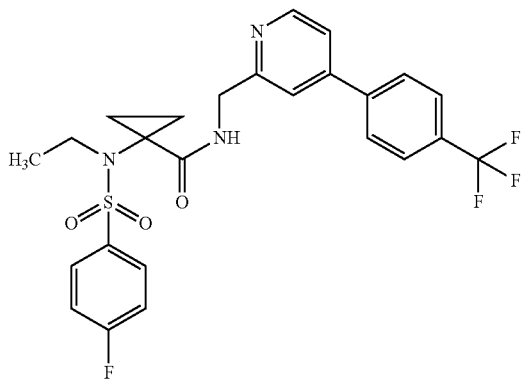 [SMILES: CCN(C1(C(=O)NCc2cc(-c3ccc(C(F)(F)F)cc3)ccn2)CC1)S(=O)(=O)c1ccc(F)cc1]

Synthesis of 4-[4-(trifluoromethyl)phenyl]pyridine-2-carbonitrile 20C

4-Chloropyridine-2-carbonitrile 19B (2.0 gr, 14.44 mmol) was dissolved in 35 ml of dioxane. The solution was added with cesium carbonate (6.8 gr), [4-(trifluoromethyl)phenyl] boronic acid (1.2 equiv., 3.3 gr) and palladium acetate/XPhos (80 mg/280 mg) under argon atmosphere. The mixture was stirred at 100° C. for 4 hours. The reaction is filtered through a pad of celite, concentrated and crystallized from diethyl ether/petroleum ether to give a beige solid (3.2 gr, 12.85 mmol, yield: 89%) $^1$HNMR (DMSO, 400 MHz) δ 7.92 (2H, dd, J=8.0 Hz), 8.12 (3H, m), 8.51 (1H, dd), 8.39 (1H, dd, J=5.2 Hz)

Synthesis of [4-[4-(trifluoromethyl)phenyl]-2-pyridyl]methanamine 21C

The nitrile 20C (3.2 g, 12.85 mmol) dissolved in 50 ml of diethyl ether was added dropwise to a mixture of LiAlH$_4$ (912 mg, 2 equiv.) in diethyl ether (80 mL) and stirred at 0° C. Then, the mixture was stirred at room temperature overnight. The excess of LiAlH$_4$ was destroyed by water addition at 0° C., the solid formed was filtered, washed with Et$_2$O and the filtrate was dried over Na$_2$SO$_4$ and evaporated to dryness to obtain 2.5 g of the amine as a yellow oil. The amine was used for the following step without purification.

Preparation of 1-[ethyl-(4-fluorophenyl)sulfonyl-amino]-N-[[4-[4-(trifluoromethyl)phenyl]-2-pyridyl]methyl]cyclopropanecarboxamide Example 60

A solution of acid 15B (0.5 g, 1.7 mmol) in THF (30 mL) was added with DEPC (0.34 mL, 1.3 mol eq) and the mixture was stirred at room temperature for about 5 minutes. Then [4-[4-(trifluoromethyl)phenyl]-2-pyridyl]methanamine 21C (0.51 g, 1.18 mol eq) and a catalytic amount of TEA were added, then the reaction mixture was stirred at room temperature overnight. The solvent was removed under reduced pressure, the residue was suspended in EtOAc (40 mL) and washed with water (50 mL) and brine. The separated organic phase was dried over Na$_2$SO$_4$ and evaporated under reduced pressure and the residue was purified by flash chromatography (3:7 EtOAc:Petroleum ether) to afford a white solid (0.18 g) after crystallization from diethyl ether. Yield=20%, $^1$HNMR (DMSO, 200 MHz) δ 1.11 (bs, 2H), 1.23 (t, 3H, J=8), 1.26 (bs, 2H), 3.41 (bs, 2H), 4.49 (d, 2H); 7.44 (m, 2H), 7.66 (dd, 1H), 7.74 (bs, 1H), 7.90 (m, 4H), 8.02 (d, 2H, J=8), 8.26 (bt, 3H), 8.63 (dd, 1H, J=5.2). [M$^{+1}$] 522.53 ($C_{25}H_{23}F_4N_3O_3S$ requires 521.53).

Example 61

1-[ethyl-(4-fluorophenyl)sulfonyl-amino]-N-[[2-pyrrolidin-1-yl-6-[4-(trifluoromethoxy)phenyl]-4-pyridyl]methyl]cyclopropanecarboxamide

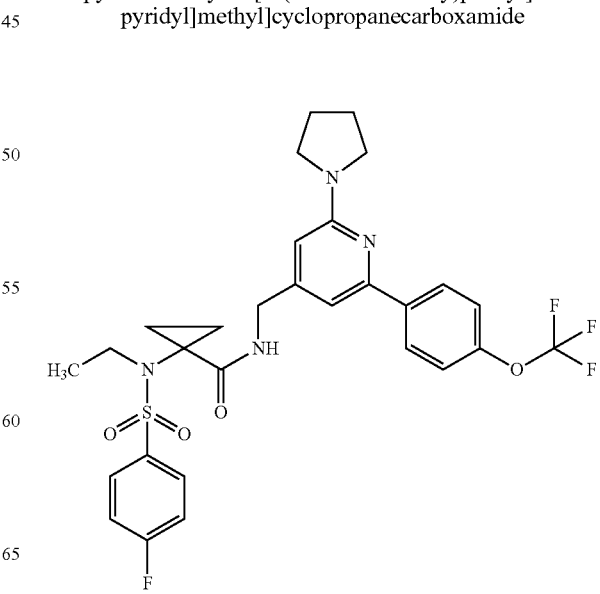

Preparation of 1-[ethyl-(4-fluorophenyl)sulfonyl-amino]-N-[[2-pyrrolidin-1-yl-6-[4-(trifluoromethoxy)phenyl]-4-pyridyl]methyl]cyclopropanecarboxamide Example 61

A solution of acid 15B (0.5 g, 1.7 mmol) in THF (30 mL) was added with DEPC (0.34 mL, 1.3 mol eq) and the mixture was stirred at room temperature for about 5 minutes. Then [4-[4-(trifluoromethoxy)phenyl]-2-pyridyl]methanamine 27C (0.61 g, 1.07 mol eq) and a catalytic amount of TEA were added, then the reaction mixture was stirred at room temperature overnight. The solvent was removed under reduced pressure, the residue was suspended in EtOAc (40 mL) and washed with water (50 mL) and brine. The separated organic phase was dried over $Na_2SO_4$ and evaporated under reduced pressure and the residue was purified by flash chromatography (3:7 EtOAc:Petroleum ether) to afford a white solid (0.18 g) after crystallization from diethyl ether. Yield=17%, $^1$HNMR (DMSO, 200 MHz) δ 1.13 (bs, 2H), 1.20 (t, 3H, J=8), 1.25 (bs, 2H), 3.46 (bq, 2H), 4.29 (d, 2H); 6.44 (s, 1H), 7.12 (s, 1H), 7.42 (m, 4H), 7.96 (m, 2H), 8.13 (m, 3H). $[M^{+1}]$ 607.53 ($C_{29}H_{30}F_4N_4O_4S$ requires 606.63).

Example 62

1-[ethyl-(4-fluorophenyl)sulfonyl-amino]-N-[[2-morpholino-6-[4-(trifluoromethyl)phenyl]-4-pyridyl]methyl] cyclopropanecarboxamide

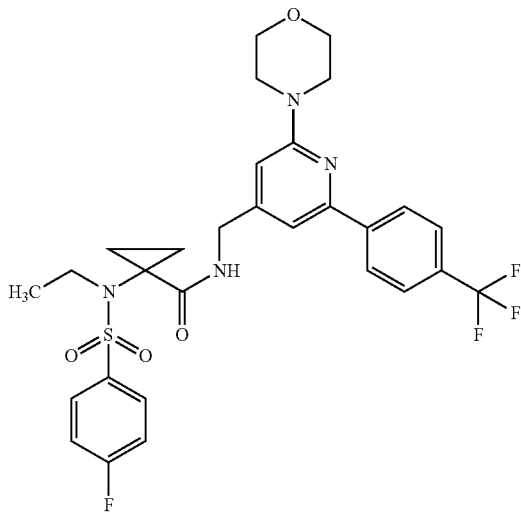 [SMILES: CCN(C1(C(=O)NCc2cc(-c3ccc(C(F)(F)F)cc3)nc(N3CCOCC3)c2)CC1)S(=O)(=O)c1ccc(F)cc1]

Preparation of 1-[ethyl-(4-fluorophenyl)sulfonyl-amino]-N-[[2-morpholino-6-[4-(trifluoromethyl)phenyl]-4-pyridyl]methyl]cyclopropanecarboxamide Example 62 with solution of acid 15B (0.5 g, 1.7 mmol) in THF (30 mL) was added with DEPC (0.34 mL, 1.3 mol eq) and the mixture was stirred at room temperature for about 5 minutes. Then [2-morpholino-6-[4-(trifluoromethyl)phenyl]-4-pyridyl] methanamine27D (0.50 g, 1.04 mol eq) and a catalytic amount of TEA were added, then the reaction mixture was stirred at room temperature overnight. The solvent was removed under reduced pressure, the residue was suspended in EtOAc (40 mL) and washed with water (50 mL) and brine. The separated organic phase was dried over $Na_2SO_4$ and evaporated under reduced pressure and the residue was purified by flash chromatography (1:1 EtOAc:Petroleum ether) to afford a white solid (220 mg) after crystallization from diethyl ether.Yield=21%, $^1$HNMR (DMSO, 200 MHz) δ 1.10 (bs, 2H), 1.20 (t, 3H, J=8), 1.35 (bs, 2H), 3.46 (bq, 2H), 3.55 (bt, 4H), 3.74 (bt, 4H), 4.34 (d, 2H); 6.81 (s, 1H), 7.39 (m, 3H), 7.86 (m, 4H), 8.23 (bm, 3H). $[M^{+1}]$ 607.81 ($C_{29}H_{30}F_4N_4O_4S$ requires 606.63).

Example 63

N-[[2-[4-(cyclopropylmethyl)piperazin-1-yl]-6-[4-(trifluoromethoxy)phenyl]-4-pyridyl]methyl]-2-[ethyl-(4-fluorophenyl)sulfonyl-amino]prop-2-enamide

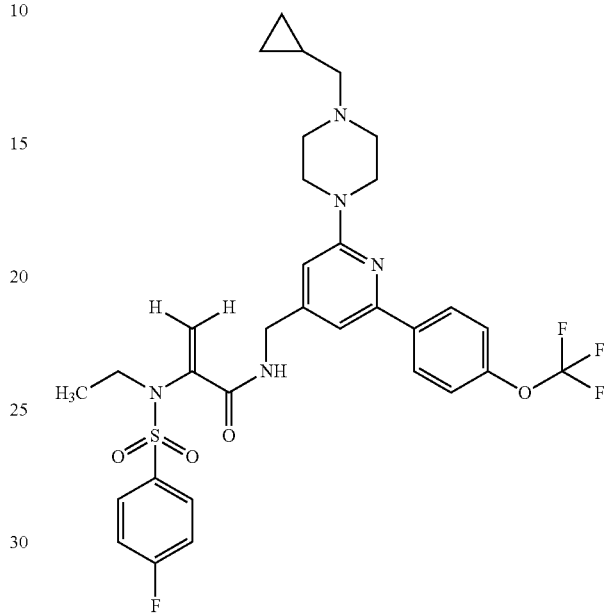

Synthesis of 2-chloro-6-[4-(cyclopropylmethyl)piperazin-1-yl]pyridine-4-carbonitrile 25D A solution of 24 (2.5 g, 14.46 mmol) in abs. EtOH (10 mL) was added with TEA (2 ml) and 4-cyclopropylmethylpiperazine (1.36 mL, 1 mol eq) and the mixture was heated at 50° C. overnight. The solvent was removed under reduced pressure, water was added to the residue and the aqueous phase was extracted with EtOAc (3×40 mL). The recombined organic phase was washed with brine (1×60 mL), dried over $Na_2SO_4$ and evaporated to afford 25D as a pale yellow solid (2.4 g, 8.67 mmol, 60% Yield). $^1$HNMR (DMSO, 400 MHz) δ 0.08 (m, 2H), 0.46 (m, 2H), 0.84 (m, 1H), 2.20 (d, 2H, J=6.8 Hz), 2.50 (m, 4H), 3.56 (m, 4H), 7.06 (s, 1H), 7.32 (s, 1H).

Synthesis of 2-[4-(cyclopropylmethyl)piperazin-1-yl]-6-[4-(trifluoromethoxy)phenyl]pyridine-4-carbonitrile 26F The nitrile 25D (2.4 g, 8.67 mmol), 4-trifluoromethoxyphenylboronic acid (2.15 g, 1.1 mol eq), palladium acetate (45 mg), cesium carbonate (4.5 g, 2 mol eq), and XPhos (190 mg) were mixed, placed under a nitrogen atmosphere and dioxane (10 mL) was added. The mixture was heated at 100° C. overnight. After cooling, the mixture was filtered through a celite pad, washed with dioxane (2×20 mL) and concentrated under reduced pressure. The residue was used for the next step without further purification.

Synthesis of [2-[4-(cyclopropylmethyl)piperazin-1-yl]-6-[4-(trifluoromethoxy)phenyl]-4-pyridyl]methanamine27F A solution of nitrile 26F (2.5 g, 6.2 mmol) in diethyl ether (30 mL) was added in small amounts to a mixture of $LiAlH_4$ (0.67 g) in diethyl ether (30 mL) stirred at 0° C. After the addition was completed, the mixture was stirred at room temperature overnight. The excess of LiAlH$_4$ was destroyed at 0° C. by addition of small amount of water (30 mL), the solid formed was filtered off and the organic filtrate was separated, washed with brine (50 mL) and dried over Na$_2$SO$_4$. The organic phase was evaporated under reduced pressure to afford 27G as a pale yellow oil (2.0 g, 80% yield). $^1$HNMR (DMSO, 200 MHz) δ 0.08 (m, 2H), 0.47 (m, 2H), 0.77 (m, 1H), 2.14 (d, 2H, J=6.6), 2.44 (m, 4H), 2.86 (bs, 2H), 3.45 (m, 4H), 3.65 (s, 2H), 6.86 (s, 1H), 7.18 (s, 1H), 7.88 (d, 2H, J=7.8), 8.24 (d, 2H, J=8.2).

Preparation of N-[[2-[4-(cyclopropylmethyl)piperazin-1-yl]-6-[4-(trifluoromethoxy)phenyl]-4-pyridyl]methyl]-2-[ethyl-(4-fluorophenyl)sulfonyl-amino]prop-2-enamide Example 63

A solution of acid 4B (273.28 mg, 1 mmol) in THF (10 mL) was added with DEPC (0.15 mL, 1.1 mol eq) and the mixture was stirred at room temperature for about 5 minutes. Then [2-[4-(cyclopropylmethyl)piperazin-1-yl]-6-[4-(trifluoromethoxy)phenyl]-4-pyridyl]methanamine 27F (405 mg, 1.04 mol eq) and a catalytic amount of TEA were added, then the reaction mixture was stirred at room temperature overnight. The solvent was removed under reduced pressure, the residue was suspended in EtOAc (40 mL) and washed with water (50 mL) and brine. The separated organic phase was dried over Na$_2$SO$_4$ and evaporated under reduced pressure and the residue was purified by flash chromatography (9:1 EtOAc:methanol) to afford a white solid (200 mg) after crystallization from diethyl ether. Yield=30%, $^1$HNMR (DMSO, 200 MHz) δ 0.05 (m, 2H), 0.45 (bm, 2H), 0.82 (m, 1H), 1.08 (t, 3H), 2.17 (d, 2H, J=6.4), 3.34 (bm, 4H), 3.49 (bm, 4H), 4.43 (d, 2H, J=6.2), 5.13 (s, 1H); 6.09 (s, 1H), 6.80 (s, 1H), 7.30 (s, 1H), 7.47 (m, 4H), 7.85 (m, 4H), 8.74 (t, 1H). [M$^{+1}$] 662.90 (C$_{32}$H$_{35}$F$_4$N$_5$O$_4$S requires 661.71).

Example 64

N-[[2-[4-(cyclopropylmethyl)piperazin-1-yl]-6-[4-(trifluoromethyl)phenyl]-4-pyridyl]methyl]-1-[ethyl-(4-fluorophenyl)sulfonyl-amino]cyclopropanecarboxamide

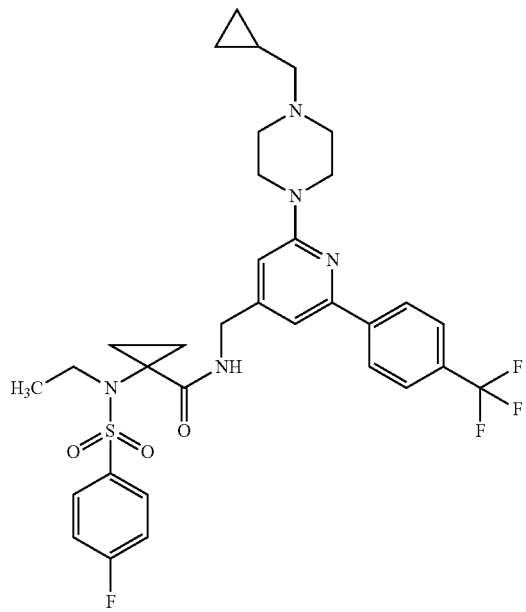 [SMILES: CCN(C1(C(=O)NCc2cc(-c3ccc(C(F)(F)F)cc3)nc(N3CCN(CC4CC4)CC3)c2)CC1)S(=O)(=O)c1ccc(F)cc1]

Synthesis of 2-[4-(cyclopropylmethyl)piperazin-1-yl]-6-[4-(trifluoromethyl)phenyl]pyridine-4-carbonitrile 26G The nitrile 25D (2.4 g, 8.67 mmol), 4-trifluoromethylphenylboronic acid (2.05 g, 1.1 mol eq), palladium acetate (45 mg), cesium carbonate (4.5 g, 2 mol eq), and XPhos (190 mg) were mixed, placed under a nitrogen atmosphere and dioxane (10 mL) was added. The mixture was heated at 100° C. overnight. After cooling, the mixture was filtered through a celite pad, washed with dioxane (2×20 mL) and concentrated under reduced pressure. The residue was used for the next step without further purification.

Synthesis of [2-[4-(cyclopropylmethyl)piperazin-1-yl]-6-[4-(trifluoromethyl)phenyl]-4-pyridyl]methanamine 27G A solution of nitrile 26G (2.5 g, 6.7 mmol) in diethyl ether (30 mL) was added in small amounts to a mixture of LiAlH$_4$ (0.67 g) in diethyl ether (30 mL) stirred at 0° C. After the addition was completed, the mixture was stirred at room temperature overnight. The excess of LiAlH$_4$ was destroyed at 0° C. by addition of small amount of water (30 mL), the solid formed was filtered off and the organic filtrate was separated, washed with brine (50 mL) and dried over Na$_2$SO$_4$. The organic phase was evaporated under reduced pressure to afford 27G as a pale yellow oil (2.0 g, 80% yield). $^1$HNMR (DMSO, 200 MHz) δ 0.00 (m, 2H), 0.37 (m, 2H), 0.77 (m, 1H), 2.14 (d, 2H, J=6.6), 2.44 (m, 4H), 2.80 (bs, 2H), 3.50 (m, 4H), 3.61 (s, 2H), 6.76 (s, 1H), 7.23 (s, 1H), 7.68 (d, 2H, J=8), 8.14 (d, 2H, J=8).

Preparation of N-[[2-[4-(cyclopropylmethyl)piperazin-1-yl]-6-[4-(trifluoromethyl)phenyl]-4-pyridyl]methyl]-1-[ethyl-(4-fluorophenyl)sulfonyl-amino]cyclopropanecarboxamide Example 64

A solution of acid 15B (0.5 g, 1.7 mmol) in THF (30 mL) was added with DEPC (0.34 mL, 1.3 mol eq) and the mixture was stirred at room temperature for about 5 minutes. Then [2-[4-(cyclopropylmethyl)piperazin-1-yl]-6-[4-(trifluoromethyl)phenyl]-4-pyridyl]methanamine 27G (636 mg, 1.04 mol eq) and a catalytic amount of TEA were added, then the reaction mixture was stirred at room temperature overnight. The solvent was removed under reduced pressure, the residue was suspended in EtOAc (40 mL) and washed with water (50 mL) and brine. The separated organic phase was dried over Na$_2$SO$_4$ and evaporated under reduced pressure and the residue was purified by flash chromatography (9:1 EtOAc:methanol) to afford a white solid (340 mg) after crystallization from diethyl ether. Yield=30%, $^1$HNMR (DMSO, 200 MHz) δ 0.40 (m, 2H), 0.63 (bm, 2H), 0.86 (m, 1H), 1.08 (m, 2H), 1.23 (t, 3H), 1.30 (bm, 2H), 3.06 (bm, 4H), 3.39 (bm, 4H), 3.64 (bm, 2H), 4.44 (m, 4H); 6.92 (s, 1H), 7.44 (m, 3H), 7.86 (m, 4H), 8.26 (bm, 3H). [M$^{+1}$] 660.81 (C$_{33}$H$_{37}$F$_4$N$_5$O$_3$S requires 659.74).

Example 65

1-[(5-chloro-2-thienyl)sulfonyl-ethyl-amino]-N-[[2-[4-(cyclopropylmethyl)piperazin-1-yl]-6-[4-(trifluoromethyl)phenyl]-4-pyridyl]methyl]cyclopropanecarboxamide

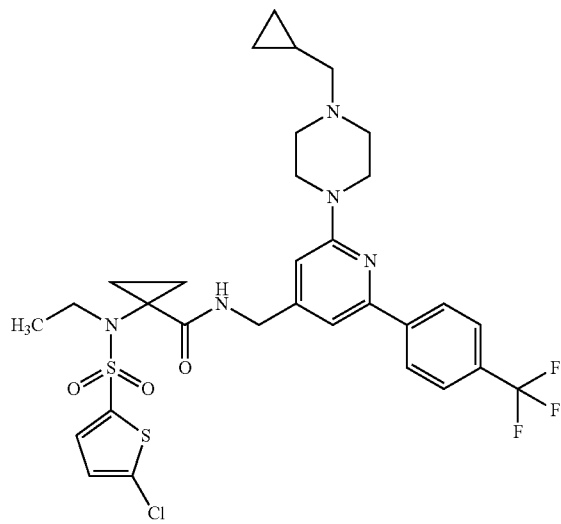 [SMILES: CCN(C1(C(=O)NCc2cc(-c3ccc(C(F)(F)F)cc3)nc(N3CCN(CC4CC4)CC3)c2)CC1)S(=O)(=O)c1ccc(Cl)s1]

Preparation of 1-[(5-chloro-2-thienyl)sulfonyl-ethyl-amino]-N-[[2-[4-(cyclopropylmethyl)piperazin-1-yl]-6-[4-(trifluoromethyl)phenyl]-4-pyridyl]methyl]cyclopropanecarboxamide Example 65

A solution of acid 18 (463 mg, 1.5 mmol) in THF (30 mL) was added with DEPC (0.23 mL, 1.0 mol eq) and the mixture was stirred at room temperature for about 5 minutes. Then [2-[4-(cyclopropylmethyl)piperazin-1-yl]-6-[4-(trifluoromethyl)phenyl]-4-pyridyl]methanamine 27G (560 mg, 1.04 mol eq) and a catalytic amount of TEA were added, then the reaction mixture was stirred at room temperature overnight. The solvent was removed under reduced pressure, the residue was suspended in EtOAc (40 mL) and washed with water (50 mL) and brine. The separated organic phase was dried over $Na_2SO_4$ and evaporated under reduced pressure and the residue was purified by flash chromatography (9:1 EtOAc:methanol) to afford a white solid (220 mg) after crystallization from diethyl ether. Yield=21.5%, $^1$HNMR (DMSO, 200 MHz) δ 0.40 (m, 2H), 0.65 (bm, 2H), 0.94 (m, 1H), 1.12 (m, 2H), 1.28 (t, 3H), 1.40 (bm, 2H), 3.04 (bm, 4H), 3.39 (bm, 4H), 3.43 (bm, 2H), 3.44 (m, 4H); 4.40 (bm, 4H), 6.87 (s, 1H), 7.30 (m, 2H), 7.60 (d, 1H, J=3.2), 7.82 (d, 2H, J=8.2), 8.25 (bm, 3H). [M$^{+1}$] 682.98 ($C_{31}H_{35}ClF_3N_5O_3S_2$ requires 682.22).

Example 66

N-[[2-(4-cyclohexylpiperazin-1-yl)-6-[4-(trifluoromethyl)phenyl]-4-pyridyl]methyl]-1-[ethyl-(4-fluorophenyl)sulfonyl-amino]cyclopropanecarboxamide

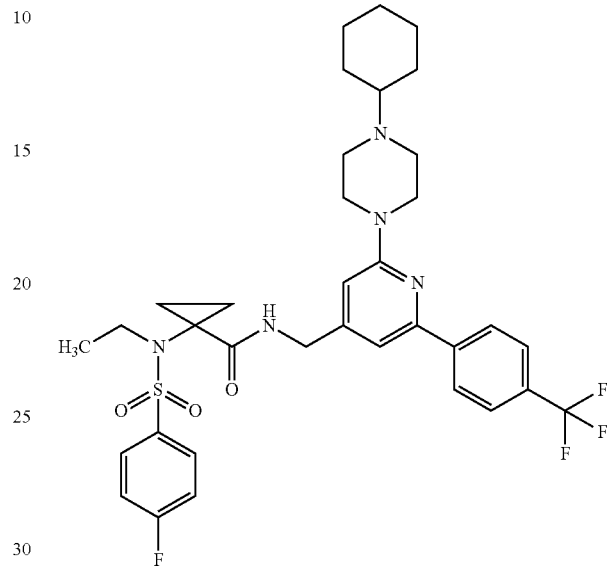

Synthesis of 2-chloro-6-[4-(cyclohexyl)piperazin-1-yl]pyridine-4-carbonitrile 25E A solution of 24 (2.5 g, 14.46 mmol) in abs. EtOH (10 mL) was added with TEA (2 ml) and N-cyclohexylpiperazine (2.43 g, 1 mol eq) and the mixture was heated at 70° C. for 4 hours. The solvent was removed under reduced pressure, water was added to the residue and the aqueous phase was extracted with EtOAc (3×40 mL). The recombined organic phase was washed with brine (1×60 mL), dried over $Na_2SO_4$ and evaporated to afford 25E as a pale yellow solid (2.2 g, 7.2 mmol, 49% Yield). $^1$HNMR (DMSO, 200 MHz) δ 1.18 (bm, 4H), 1.59 (bm, 1H), 1.74 (bm, 4H), 2.26 (bm, 2H), 2.53 (m, 4H), 3.52 (m, 4H), 7.04 (s, 1H), 7.30 (s, 1H).

Synthesis of 2-[4-(cyclohexyl)piperazin-1-yl]-6-[4-(trifluoromethyl)phenyl]pyridine-4-carbonitrile 26E The nitrile 25E (2.2 g, 7.2 mmol), 4-trifluoromethylphenylboronic acid (2.05 g, 1.1 mol eq), palladium acetate (45 mg), cesium carbonate (4.5 g, 2 mol eq), and XPhos (190 mg) were mixed, placed under a nitrogen atmosphere and dioxane (10 mL) was added. The mixture was heated at 100° C. overnight. After cooling, the mixture was filtered through a celite pad, washed with dioxane (2×20 mL) and concentrated under reduced pressure. The residue was a yellow oil. $^1$HNMR (DMSO, 200 MHz) δ 1.14 (bm, 4H), 1.59 (bm, 1H), 1.75 (bm, 4H), 2.26 (bm, 2H), 2.58 (m, 4H), 3.62 (m, 4H), 7.33 (s, 1H), 7.66 (s, 1H), 7.82 (d, 2H, J=8.2), 8.28 (d, 2H, J=8.2).

Synthesis of [2-[4-(cyclohexyl)piperazin-1-yl]-6-[4-(trifluoromethyl)phenyl]-4-pyridyl]methanamine 27E A solution of nitrile 26E (3.2 g, 7.7 mmol) in diethyl ether (30 mL) was added in small amounts to a mixture of LiAlH$_4$ (800 mg) in diethyl ether (30 mL) stirred at 0° C. After the addition was completed, the mixture was stirred at room temperature overnight. The excess of LiAlH$_4$ was destroyed at 0° C. by addition of small amount of water (30 mL), the solid formed was filtered off and the organic filtrate was separated, washed with brine (50 mL) and dried over Na$_2$SO$_4$. The organic phase was evaporated under reduced pressure to afford 27E as a pale yellow oil (1.76 g, 55% yield). $^1$HNMR (DMSO, 200 MHz) δ 1.14 (bm, 4H), 1.52 (bm, 1H), 1.77 (bm, 4H), 2.26 (bm, 2H), 2.60 (m, 4H), 3.36 (b, 2H), 3.55 (m, 4H), 3.70 (s, 2H), 6.84 (s, 1H), 7.32 (s, 1H), 7.79 (d, 2H, J=8.2), 8.24 (d, 2H, J=8.2).

Preparation of N-[[2-(4-cyclohexylpiperazin-1-yl)-6-[4-(trifluoromethyl)phenyl]-4-pyridyl]methyl]-1-[ethyl-(4-fluorophenyl)sulfonyl-amino]cyclopropanecarboxamide Example 66

A solution of acid 15B (0.5 g, 1.7 mmol) in THF (30 mL) was added with DEPC (0.34 mL, 1.3 mol eq) and the mixture was stirred at room temperature for about 5 minutes. Then [2-[4-(cyclohexyl)piperazin-1-yl]-6-[4-(trifluoromethyl)phenyl]-4-pyridyl]methanamine 27E (712 mg, 1.04 mol eq) and a catalytic amount of TEA were added, then the reaction mixture was stirred at room temperature overnight. The solvent was removed under reduced pressure, the residue was suspended in EtOAc (40 mL) and washed with water (50 mL) and brine. The separated organic phase was dried over Na$_2$SO$_4$ and evaporated under reduced pressure and the residue was purified by flash chromatography (9:1 EtOAc:methanol) to afford a white solid (140 mg) after crystallization from diethyl ether. Yield=20%, $^1$HNMR (DMSO, 200 MHz) δ 1.18 (bm, 9H), 1.83 (bm, 4H), 2.30 (bm, 1H), 2.59 (bm, 4H), 3.34 (bm, 2H), 3.57 (bm, 4H), 4.40 (bd, 2H), 6.82 (s, 1H), 7.34 (m, 3H), 7.83 (m, 4H), 8.21 (bm, 3H). [M$^{+1}$] 688.41 (C$_{35}$H$_{41}$F$_4$N$_5$O$_3$S requires 687.79).

Example 67

1-[(5-chloro-2-thienyl)sulfonyl-ethyl-amino]-N-[[2-(4-cyclohexylpiperazin-1-yl)-6-[4-(trifluoromethyl)phenyl]-4-pyridyl]methyl]cyclopropanecarboxamide

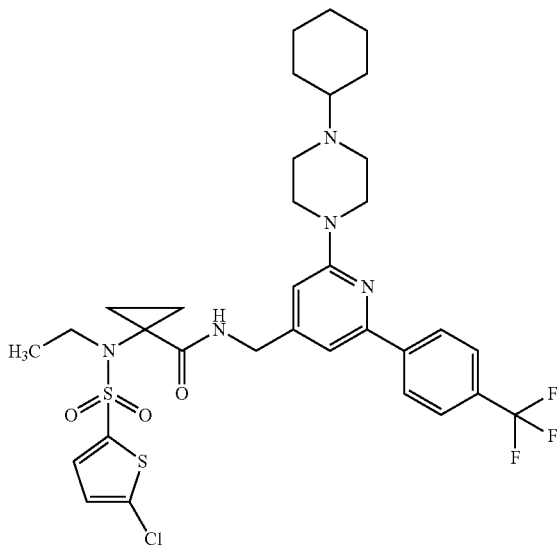 [SMILES: CCN(C1(C(=O)NCc2cc(-c3ccc(C(F)(F)F)cc3)nc(N3CCN(C4CCCCC4)CC3)c2)CC1)S(=O)(=O)c1ccc(Cl)s1]

Preparation of 1-[(5-chloro-2-thienyl)sulfonyl-ethyl-amino]-N-[[2-(4-cyclohexylpiperazin-1-yl)-6-[4-(trifluoromethyl)phenyl]-4-pyridyl]methyl]cyclopropanecarboxamide Example 67

A solution of acid 18 (463 mg, 1.5 mmol) in THF (30 mL) was added with DEPC (0.23 mL, 1.0 mol eq) and the mixture was stirred at room temperature for about 5 minutes. Then [2-[4-(cyclopropylmethyl)piperazin-1-yl]-6-[4-(trifluoromethyl)phenyl]-4-pyridyl]methanamine 27E (628 mg, 1.04 mol eq) and a catalytic amount of TEA were added, then the reaction mixture was stirred at room temperature overnight. The solvent was removed under reduced pressure, the residue was suspended in EtOAc (40 mL) and washed with water (50 mL) and brine. The separated organic phase was dried over Na$_2$SO$_4$ and evaporated under reduced pressure and the residue was purified by flash chromatography (9:1 EtOAc:methanol) to afford a white solid (110 mg) after crystallization from diethyl ether. Yield=10%, $^1$HNMR (DMSO, 200 MHz) δ 1.15 (bm, 9H), 1.80 (bm, 4H), 2.35 (bm, 1H), 2.59 (bm, 4H), 3.37 (bm, 2H), 3.65 (bm, 4H), 4.45 (bd, 2H), 6.89 (s, 1H), 7.35 (m, 2H), 7.60 (d, 1H, J=3.4), 7.82 (d, 2H, J=8), 8.25 (bm, 3H). [M$^{+1}$] 711.65 (C$_{33}$H$_{39}$ClF$_3$N$_5$O$_3$S$_2$ requires 710.27).

Scheme 3

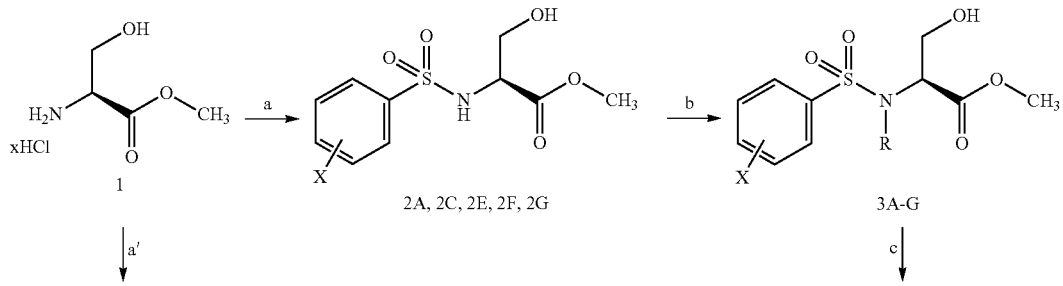

91 -continued 92

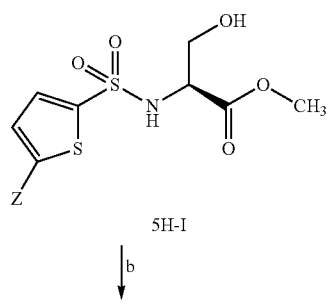

5H-I

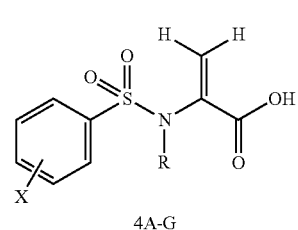

4A-G

↓ b

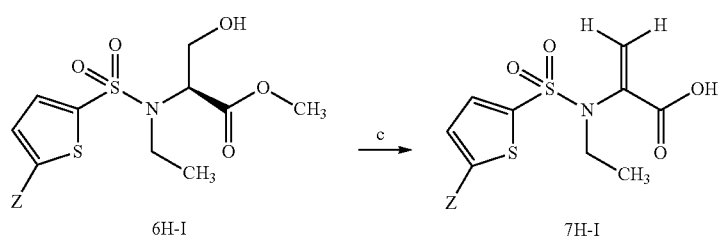

Reagents: a) X-substituted-benzensulfonyl chloride, TEA, CH₂Cl₂; a′) 5-Z-thiophene-2-sulfonylchloride, TEA, CH₂Cl₂; b) alkyl iodide, K₂CO₃, DMF; c) 20% aq. NaOH or LiOH•H₂O, THF/water-acetylchloride, Pyr.

Substituents:
A, X=4-F and R=methyl; B, X=4-F and R=ethyl; C, X=4-Cl and R=methyl; D, X=4-Cl and R=ethyl; E, X=4-CH₃ and R=methyl; F, X=3-F and R=ethyl; G, X=3,4-difluoro and R=ethyl.
5-7H, Z=H; 5-7I, Z=Cl. For 2A, 2C and 2E, R=H.

Scheme 4

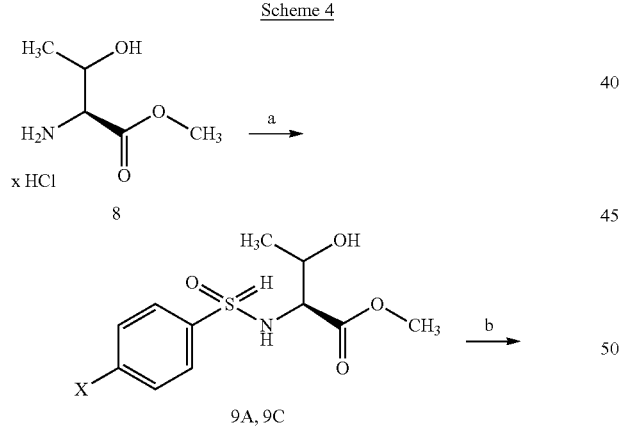

-continued

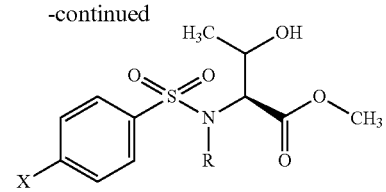

10A-D

↓ c

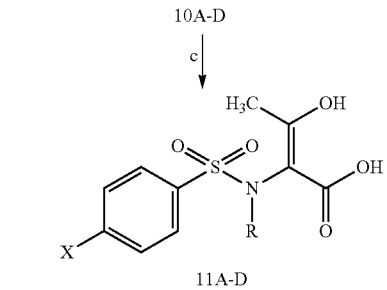

11A-D

Reagents: a) 4-X-benzenesulfonyl chloride, TEA, CH₂Cl₂; b) alkyl iodide, K₂CO₃, DMF; c) LiOH•H₂O, THF/water-acetyl chloride, Pyr Substituents:
A, X=F and R=methyl; B, X=F and R=ethyl; C, X=Cl and R=methyl; D, X=Cl and R=ethyl. For 9A and 9C, R=H.

Scheme 5

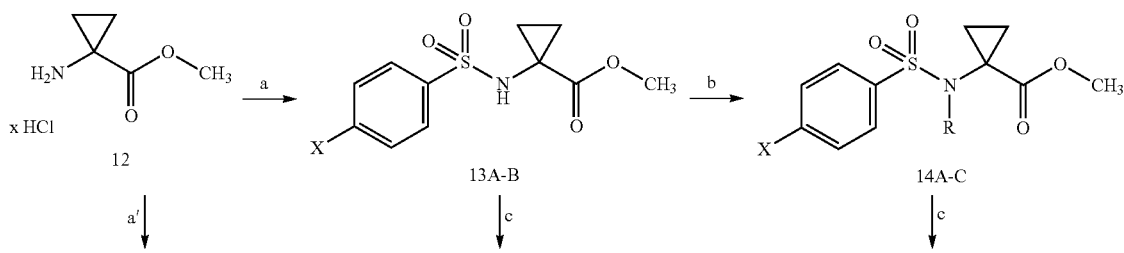

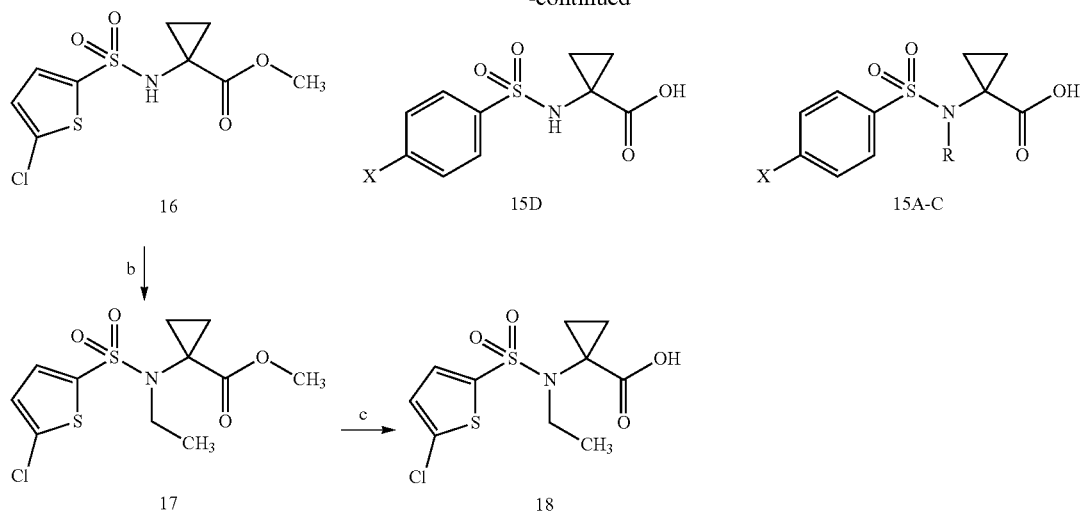

Reagents: a) 4-fluoro/chlorobenzensulfonyl chloride, TEA, CH$_2$Cl$_2$; a') 4-chlorothiophene-2-sulfonylchloride, TEA, CH$_2$Cl$_2$ b) 2-ethyl iodide, K$_2$CO$_3$, DMF; c) 10% aq. NaOH or LiOH•H$_2$O, THF/water.

Substituents:
A, X=F and R=methyl; B, X=F and R=ethyl, C, X=Cl and R=ethyl. For 15D, X=F.

Scheme 6

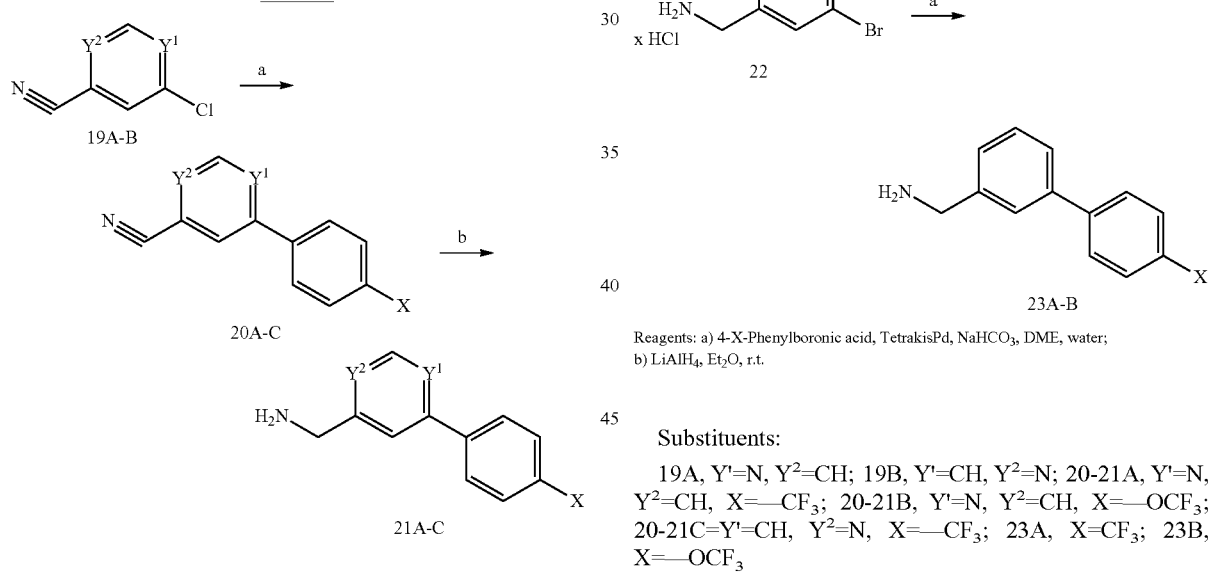

Reagents: a) 4-X-Phenylboronic acid, TetrakisPd, NaHCO$_3$, DME, water; b) LiAlH$_4$, Et$_2$O, r.t.

Substituents:
19A, Y$^1$=N, Y$^2$=CH; 19B, Y$^1$=CH, Y$^2$=N; 20-21A, Y$^1$=N, Y$^2$=CH, X=—CF$_3$; 20-21B, Y$^1$=N, Y$^2$=CH, X=—OCF$_3$; 20-21C=Y$^1$=CH, Y$^2$=N, X=—CF$_3$; 23A, X=CF$_3$; 23B, X=—OCF$_3$ Scheme 7

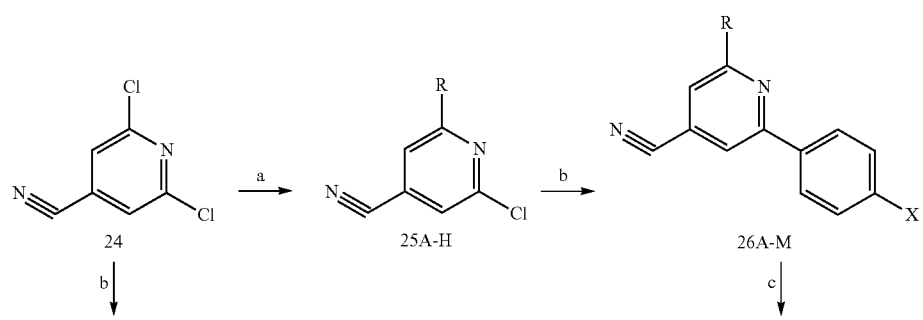

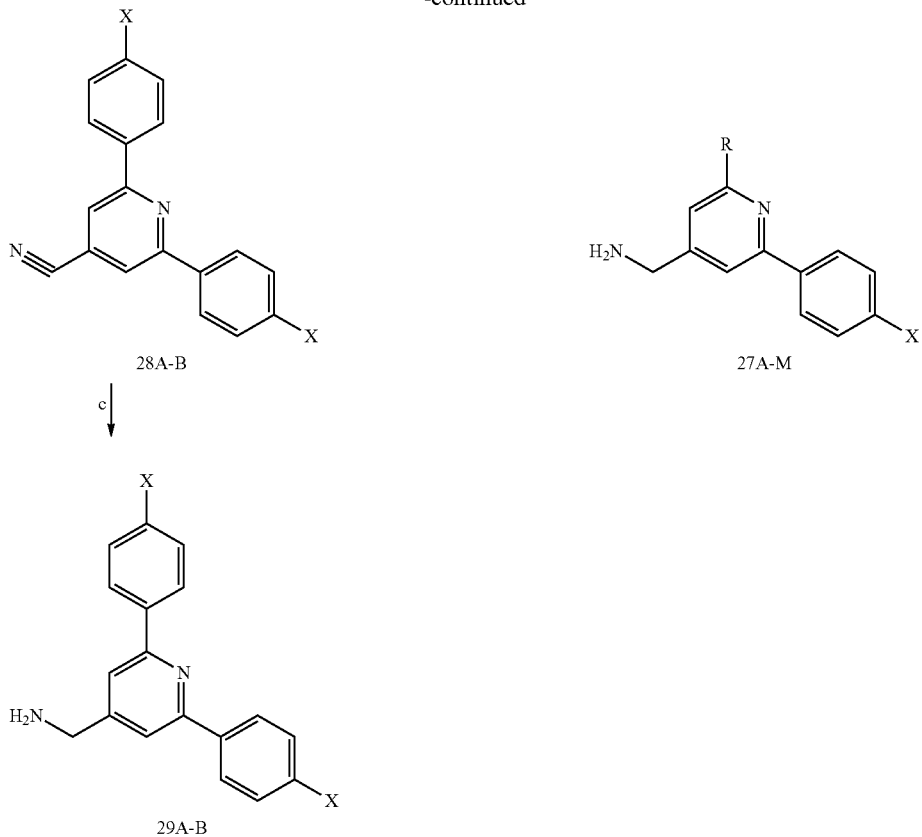

Reagents: a) Pyrrolidine, morpholine, N-cyclopropylmethyl-piperazine, N-cycloexyl-piperazine, sodioethoxyde, EtOH, 70° C.; or Examethyldiphosphoramide, 120° C., 18 h or sodiomethoxide, MeOH, 60° C.; or 2-isopropanol, NaH 60%, 70° C. b) 4-X-Phenylboronic acid, TetrakisPd, NaHCO₃, DME, water or 4-CF₃-phenylboronic acid, Pd(OAC)₂, CsCO₃, XPhos, Dioxane, 100° C.; c) LiAlH₄, Et₂O, r.t.

Substituents:

25A, R=pyrrolidine; 25B, R=morpholine; 25C, R=N,N'-dimethylamino; 25D, R=N-cyclopropylmethyl-piperazine; 25E, R=N-cycloexylpiperazine; 25F, R=methoxy; 25G, R=ethoxy; 25H, R=isopropyloxy; 26-27A, R=pyrrolidine and X=—CF₃; 26-27B, R=morpholine and X=—CF₃; 26-27C, R=pyrrolidine and X=—OCF₃; 26-27D, R=morpholine and R=—OCF₃; 26-27E, R=N,N'-dimethylamino and X=—CF₃; 26-27F, R=N-cyclopropylmethyl-piperazine and X=—OCF₃; 26-27G, R=N-cyclopropylmethyl-piperazine and X=—CF₃; 26-27H, R=N—cycloexylpiperazine and R=—CF₃; 26-27I, R=—OCH₃ and X=—CF₃; 26-27L, R=—OCH₂CH₃ and X=—CF₃; 26-27M, R=Isopropyloxy and X=—CF₃; 28-29A, X=—CF₃; 28-29B, X=—OCF₃.

Pharmacology

Drugs and reagents were obtained from the indicated companies: PF-4840154, ionomycin, laminin, poly-L-lysine, collagenase, trypsin, L-glutamine, penicillin/streptomycin, DMEM, HBSS, mouse-NGF-7S, ARA-C, HEPES, Tween80, Complete Freund's Adjuvant (CFA) and BSA (Sigma, Italy); FBS and HS (Gibco, Italy); Fura-2-AM-ester (Vinci-Biochem, Italy) and Methylcellulose (Fluka, Switzerland). The stock concentration (10 mM) of PF-4840154, Fura-2-AM-ester, ionomycin and all tested compounds were prepared in 100% DMSO.

PF-4840154 (1 µM)-Induced $Ca^{2+}$ Fluorescence Measurements in A549 Cell Line

Human lung adenocarcinoma epithelial cell line (A549) stably expressing native human TRPA1 receptors were used. The cells were cultured in medium consisting of Eagle's minimal essential medium (EMEM) supplemented with 10% fetal bovine serum (FBS), penicillin (100 IU/ml), streptomycin (100 mg/ml), L-glutamine (2 mM), sodium bicarbonate (2.5 g/L) and HEPES (24 mM). Cells were kept at 37° C. in 5% $CO_2$/humidified air. For the experiments the cells were seeded at a density of 16,000 cells/well into 96-well black, clear-bottom plates. After 24 hours incubation the cells were loaded with medium supplemented with 2.5 mM probenecid, 3 µM of the calcium sensitive fluorescent dye Fluo-4 AM and 0.01% pluronic acid, for 30 min at 37° C. Afterwards the loading solution was aspirated and 100 µl/well of assay buffer: Hank's Balanced Salt Solution (HBSS) supplemented with 2.5 mM probenecid and 500 µM Brilliant Black (Aldrich) was added. Stock solutions (100 mM) of ligands were made in Dimethyl Sulfoxide (DMSO) and stored at −20° C. Serial dilutions of ligands for experimental use were made in HBSS buffer. After placing both plates (cell culture and compound plate) into the FlexStation II (Molecular Device, Union City, Calif. 94587, US), fluorescence changes were measured. On-line additions were carried out in a volume of 50 µl/well. To facilitate drug diffusion into the wells in antagonist type experiments, the studies were performed at 36.5° C.

and three cycles of mixing (25 µl from each well moved up and down 3 times) were performed immediately after antagonist injection to the wells. All exemplified compounds were tested alone (to address residual agonistic activity) and against 1 µM of PF-4840154 to address inhibitory activity at the initial concentration of 10 µM. For selected examples the entire inhibitory concentration-response curves were constructed and the $IC_{50}$ value calculated.

PF-4840154 (10 µM)-Induced $Ca^{2+}$ Fluorescence Measurements in Cultured Rat Dorsal Root Ganglia Neurons Male SD rats (~50 g, Charles River, Italy) were terminally anaesthetized and decapitated. Dorsal root ganglia were removed and placed in cold Hank's balanced salt solution (HBSS) before being transferred to collagenase (2 mg/ml) and trypsin (1 mg/ml) for 35 min at 37° C. The ganglia, placed in cold DMEM supplemented with 10% fetal bovine serum, 10% horse serum, 2 mM L-glutamine, 100 U/ml penicillin and 100 µg/ml streptomycin, were dissociated in single cells by several passages through a series of syringe needles (23G down to 25G). The medium and the ganglia were filtered to remove debris, topped up with 4 ml of DMEM medium and centrifuged (1100 rpm for 6 min). The final cell pellet was re-suspended in DMEM medium [supplemented with 100 ng/ml mouse Nerve Growth Factor (mouse-NGF-7S) and cytosine-β-D-arabinofuranoside free base (ARA-C) 2.5 µM]. The cells were plated on poly-L-lysine (8.3 µM)- and laminin (5 µM)-coated 25 mm glass cover slips and kept for 2 days at 37° C. in a humidified incubator gassed with 5% $CO_2$ and air, then treated with Fura-2-AM-ester (5 µM) in a $Ca^{2+}$ buffer solution having the following composition (mM): $CaCl_2$ 1.4, KCl 5.4, $MgSO_4$ 0.4, NaCl 135, D-glucose 5, HEPES 10 with BSA (0.1%), at pH 7.4, for 40 min at 37° C. The cells were then washed twice with the $Ca^{2+}$ buffer solution and transferred to a chamber on the stage of a Nikon eclipse TE300 microscope. Fura-2-AM-ester was excited at 340 nM and 380 nM to indicate relative $[Ca^{2+}]_i$ changes by the $F_{340}/F_{380}$ ratio recorded with a dynamic image analysis system (Laboratory Automation 2.0, RCS, Florence, Italy) and the cells were allowed (at least 10 min) to attain a stable fluorescence before beginning the experiment. A calibration curve was set up using buffer containing Fura-2-AM-ester and determinant concentrations of free $Ca^{2+}$. This curve was then used to convert the data obtained from the $F_{340}/F_{380}$ ratio to $[Ca^{2+}]_i$ (nM).

All exemplified compounds were tested at the concentration of 10 µM against the calcium uptake induced by 10 µM PF-4840154. For selected examples, the entire concentration response curves were constructed and the respective $IC_{50}$ value calculated.

Agonist (PF-4840154)-Induced Mechanical Hyperalgesia in Rats

The method is used to investigate the anti-hyperalgesic effects of the compounds listed in the present invention following agonist (PF-4840154)-induced hyperalgesic responses. The activity is indicative of TRPA1 receptor occupancy following oral dosing. Specifically, male SD rats (Charles River, Italy) weighing 70-100 g. were used. The anti-hyperalgesic effects were investigated using the electronic dynamometer test. PF-4840154 (Sigma, USA) was used to induce mechanical hyperalgesia. Local, intraplantar injection of PF-4840154 at 0.05 nmol/50 µl/paw caused the reduction of the hind paw withdrawal response induced by mechanical stimuli. Mechanical stimulation was induced in basal condition and 30, 60, 120, 180 and 240 minutes after the oral administration of the antagonists dissolved in 2.5% DMSO and 30% Solutol. Compounds were orally administered (30 µmol/kg/10 ml) to rats 1 hour before the injection of PF-4840154 into the plantar surface of a rat's hind using a micro syringe.

Oxaliplatin-Induced Mechanical Hyperalgesia in Rats

The method described by Nassini et al. (*Pain*, 2011, 152(7), 1621-31) was used with minor modifications. Restrained rats were treated with a single intravenous bolus injection of oxaliplatin (2.5 mg/kg) dissolved in normal saline. This approach was sufficient to elicit reproducible allodynic behaviour evident 3 days post injection and during the day thereafter. For convenience all acute experiments were conducted 7 days post injection when compounds were orally administered at 30 µmol/kg.

Results

PF-4840154 (1 µM)-Induced $Ca^{2+}$ Fluorescence Measurements in Cultured A549 Cell Line PF-4840154 (1 µM) increased $[Ca^{2+}]$ in the vast majority (95%) of cultured cells which were thereby identified as TRPA1 expressing cells. All synthesized derivatives were initially tested at the final concentration of 10 µM and then, most active compounds were further investigated to determine their respective potency evaluating the $IC_{50}$ value defined as the concentration eliciting 50% inhibition under the experimental condition used. The compounds were able to effectively inhibit calcium uptake and several exhibited an inhibitory activity at the tested concentration comprised between 80% and 100% of agonist response. Several derivatives among those of Examples 1-67 showed 1050 values <50 nM.

The $IC_{50}$ values of the compounds of Examples 1, 7, 10, 11, 12, 14, 15, 34, 37, 38, 39, 40, 43, 44, 50, 51, 53, 55 and 59 calculated against PF-4840154-evoked $[Ca^{2+}]_i$ mobilization were 15, 36, 25, 17, 33, 40, 22, 25, 18, 17, 20, 16, 48, 18, 19, 41, 17, 31, 38 nM, respectively.

Tables 1, describes the calcium assay data obtained in A549 cells for exemplified compounds of Formula I.

TABLE 1

| Example | % inhibition at 10 µM | $IC_{50}$ (nM) |
|---|---|---|
| 1 | 100% | 15 |
| 2 | 98% | 135 |
| 3 | 95% | 93 |
| 4 | 98% | 78 |
| 5 | 99% | 100 |
| 6 | 100% | 355 |
| 7 | 100% | 36 |
| 8 | 100% | 76 |
| 9 | 98% | 68 |
| 10 | 99% | 25 |
| 11 | 99% | 17 |
| 12 | 100% | 33 |
| 13 | 99% | 182 |
| 14 | 100% | 40 |
| 15 | 100% | 22 |
| 16 | 99% | 457 |
| 17 | 98% | 120 |
| 18 | 100% | 93 |
| 19 | 100% | 74 |
| 20 | 96% | 251 |
| 21 | 100% | 323 |
| 22 | 97% | 246 |
| 23 | 98% | 437 |
| 24 | 97% | 724 |
| 25 | 100% | 76 |
| 26 | 100% | 151 |
| 27 | 100% | 135 |
| 28 | 100% | 129 |
| 29 | 100% | 138 |
| 30 | 100% | 100 |
| 31 | 100% | 57 |
| 32 | 80% | >4 µM |

TABLE 1-continued

| Example | % inhibition at 10 µM | IC$_{50}$ (nM) |
|---|---|---|
| 33 | 55% | >2 µM |
| 34 | 100% | 25 |
| 35 | 100% | 58 |
| 36 | 100% | 118 |
| 37 | 100% | 18 |
| 38 | 100% | 17 |
| 39 | 100% | 20 |
| 40 | 100% | 16 |
| 41 | 96% | 135 |
| 42 | 100% | 104 |
| 43 | 100% | 48 |
| 44 | 100% | 18 |
| 45 | 100% | 151 |
| 46 | 97% | 63 |
| 47 | 96% | 113 |
| 48 | 96% | 260 |
| 49 | 98% | 95 |
| 50 | 100% | 19 |
| 51 | 100% | 41 |
| 52 | 99% | 87 |
| 53 | 100% | 17 |
| 54 | 47% | >10 µM |
| 55 | 100% | 31 |
| 56 | 100% | 275 |
| 57 | 97% | 275 |
| 58 | 100% | 160 |
| 59 | 99% | 38 |
| 60 | 100% | 423 |
| 61 | 95% | 784 |
| 62 | 100% | 660 |
| 63 | 99% | 175 |
| 64 | 99% | 338 |
| 65 | 100% | 327 |
| 66 | 93% | 1.5 µM |
| 67 | 95% | 590 |

PF-4840154 (10 µM)-Induced $Ca^{2+}$ Fluorescence Measurements in Cultured Primary Dorsal Root Rat Neurons As mentioned above, selected compounds were also characterized with respect to their specific activity on PF-4840154-induced $[Ca^{2+}]_i$ mobilization in primary culture of rat dorsal ganglia neurons. In this assay, Examples 1, 7, 10, 11, 14, 15, 19 and 38 had estimated IC$_{50}$ of 14, 29, 47 20, 60, 32, 68 nM, and 14 respectively.

Tables 2 below, describes the calcium assay data obtained in primary culture of rat dorsal ganglia neurons of selected compounds of formula I.

TABLE 2

| Example | IC50 (nM) |
|---|---|
| 1 | 14 |
| 7 | 29 |
| 10 | 47 |
| 11 | 20 |
| 14 | 60 |
| 15 | 32 |
| 19 | 68 |
| 38 | 14 |

Agonist (PF-4840154)-Induced Mechanical Hyperalgesia in Rats

The more potent antagonists were orally administered at 30 µmol/kg to rats and their anti-hyperalgesic activity tested against PF-4840154 administered intraplantary at the dose of 0.05 nmol/50 µl/paw. Examples 1, 4, 5, 7, 10, 11, 14, 15, 19, 26, 30, 37, 38, 50, 51, 53 and 59 were able to effectively counteract PF-4840154 producing a robust and long-lasting reversal of mechanical allodynia showing 80, 67, 76, 74, 63, 72, 75, 72, 74, 64, 82, 95, 87, 76, 76, 89 and 111% of reversal, respectively.

Tables 3 below, describes the anti-hyperalgesic activity of selected examples of Formula I in PF-4840154-induced hyperalgesic responses.

TABLE 3

| Example | Maximal inhibition (%) |
|---|---|
| 1 | 80 |
| 4 | 67 |
| 5 | 76 |
| 7 | 74 |
| 10 | 63 |
| 11 | 72 |
| 14 | 75 |
| 15 | 72 |
| 19 | 74 |
| 26 | 64 |
| 30 | 82 |
| 37 | 95 |
| 38 | 87 |
| 50 | 76 |
| 51 | 76 |
| 53 | 89 |
| 59 | 111 |

Oxaliplatin-Induced Mechanical Hyperalgesia in Rats

The more potent antagonists were orally administered at 30 µmol/kg to rats 7 days post intravenous injection of oxaliplatin at the dose of 2.5 mg/kg and their anti-nociceptive effect was measured. Examples 1, 34, 37, 40, 50, 51, 53 and 59 were able to effectively counteract the oxaliplatin effect producing a robust and long-lasting reversal of mechanical allodynia showing 97, 71, 82, 103, 82, 65, 83 and 67% of reversal, respectively.

Tables 4 below, describes the anti-hyperalgesic activity of selected examples of Formula I in oxaliplatin-induced mechanical hyperalgesia.

TABLE 4

| Example | Maximal inhibition (%) |
|---|---|
| 1 | 97 |
| 34 | 71 |
| 37 | 82 |
| 40 | 103 |
| 50 | 82 |
| 51 | 65 |
| 53 | 83 |
| 59 | 67 |

The invention claimed is:

1. A compound of formula (I)

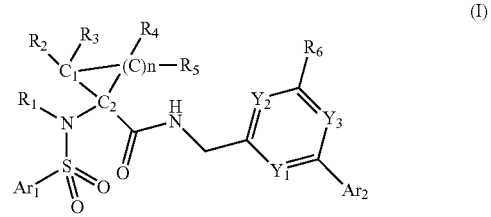

wherein:
Ar$_1$ is:
i) phenyl substituted with 0, 1, 2 or 3 substituents R$_a$; or
ii) a 5- or 6-membered monocyclic aromatic heterocycle ring optionally substituted with one or two substituents

101

$R_a$; where each $R_a$ is independently halo, —$C_{1-4}$alkyl, —$OC_{1-4}$alkyl, —CN, —$CF_3$, —$OCF_3$, —$NO_2$, —C(O)$C_{1-4}$alkyl or —$CO_2H$;

$Ar_2$ is:

i) phenyl substituted with 0, 1, 2 or 3 substituents $R_b$; where each $R_b$ is independently halo, —$C_{1-4}$alkyl, —C(O)$NR_cR_d$, —$OC_{1-4}$alkyl, —$OC_{0-4}$alkyl$CF_3$, —CN, —$CF_3$, —$OCF_2H$, —$NO_2$, —$NR_cR_d$, —$S(O)_{0-2}C_{1-4}$alkyl, —C(O)$C_{1-4}$alkyl, S(O)(O)$NH_2$, —$(CH_2)_{0-2}$-morpholinyl, piperidin-1-yl, piperazinyl, said piperazinyl being optionally substituted with a methyl, or two $R_b$ substituents on adjacent carbon atoms taken together form —$O(CH_2)_{1-2}O$—;

ii) pyridyl substituted with 0, 1 or 2 substituents $R_e$; where each $R_e$ is independently selected from halo, —$C_{1-4}$alkyl, —$OC_{1-4}$alkyl, —$CF_3$, —$NR_cR_d$ or 4-morpholinyl; or iii) a bicyclic 9-11-membered aromatic heterocycle, optionally substituted with 1 substituent $R_f$.

where $R_f$ is —$C_{1-4}$alkyl;

$R_c$ and $R_d$ are each independently selected from H or —$C_{1-4}$ alkyl;

$R_1$ is H, $C_{1-4}$alkyl-O—$C_{1-4}$alkyl, or $C_{1-4}$alkyl optionally substituted with halo;

$R_2$, $R_3$, $R_4$, and $R_5$ are each independently H, halo or —$C_{1-4}$alkyl;

n is 0 or 1 providing that when n is 1 the bond between C1 and C2 is single and when n is 0 the bond between C1 and C2 is double;

each $Y_1$, $Y_2$ and $Y_3$ is independently CH or N;

$R_6$ is i) H, —$C_{1-4}$alkyl, —$CF_3$, —$OR_z$ or —$NR_hR_i$;

where $R_h$ is selected from:

a) H, —$C_{0-4}$alkyl$CF_3$, —$C_{1-4}$alkyl-$N(CH_3)_2$, saturated $C_{3-7}$cycloalkyl or —$C_{1-4}$alkyl-monocyclic heteroaryl ring;

b) —$C_{1-5}$alkyl optionally substituted with OH;

c) —$C_{1-4}$alkyl-heterocycloalkyl, wherein said heterocycloalkyl is optionally substituted with —$C_{1-4}$alkyl; or d) —$C_{0-4}$alkyl-phenyl, said phenyl being optionally substituted with one or two $R_j$ moieties; where each $R_j$ is independently halo, —$OC_{1-4}$alkyl, Rz is —$C_{1-4}$alkyl, —$C_{1-4}$alkyl$CF_3$ or —$C_{1-4}$alkyl-heterocycloalkyl;

ii) 1-pyrrolidinyl optionally substituted with a moiety selected from the group consisting of —$NR_kR_i$ and —$C_{1-4}$alkyl, said —$C_{1-4}$alkyl optionally substituted with —OH;

iii) 1-piperidinyl optionally substituted with —$C_{1-4}$alkyl, —C(O)$NH_2$, —$CO_2C_{1-4}$alkyl or —$C_{0-4}$alkyl-phenyl;

iv) piperazinyl optionally substituted with —$C_{1-5}$alkyl, —$OC_{1-4}$alkyl, —$C_{0-4}$alkylpyridyl, —$C_{0-4}$alkyl-1-methyl-piperidin-4-yl, —$C_{0-4}$alkyl$NR_kR_i$ or —$C_{0-4}$alkyl-phenyl, said phenyl being optionally substituted with one or two $R_T$ substituents; where each $R_T$ substituent is selected from the group consisting of halo, —$OCF_3$, —$C_{1-4}$alkyl, —$OC_{1-4}$alkyl, —$CO_2C_{1-4}$alkyl, —C(O)$C_{1-4}$alkyl and —$C_{0-4}$alkyl$NR_kR_i$, or two $R_T$ substituents on adjacent carbon atoms taken together form —$O(CH_2)_{1-2}O$—;

v) phenyl optionally substituted with halo, —$CF_3$, —$OCF_3$;

vi) pyridyl;

vii) morpholin-yl;

$R_k$ is H, —$C_{1-4}$alkyl or —$C(O)_{1-2}C_{1-4}$alkyl;

$R_i$ is H or $C_{1-4}$alkyl;

102

N-oxides, enantiomers, racemic mixtures and pharmaceutically acceptable salts thereof.

2. The compound according to claim 1 of formula (IA)

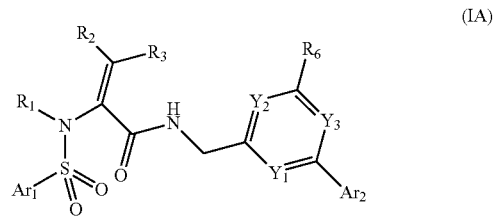

(IA)

wherein:

$Ar_1$ is:

i) phenyl substituted with 0, 1, 2 or 3 substituents $R_a$; or ii) a 5-6-membered monocyclic aromatic heterocycle ring, optionally substituted with one or two substituents $R_a$; where each $R_a$ is independently halo, —$C_{1-4}$alkyl, —$OC_{1-4}$alkyl, —CN, —$CF_3$, —$OCF_3$, —$NO_2$, —C(O)$C_{1-4}$alkyl or —$CO_2H$;

$Ar_2$ is:

i) phenyl substituted with 0, 1, 2 or 3 substituents $R_b$; where each $R_b$ is independently halo, —$C_{1-4}$alkyl, —C(O)$NR_cR_d$, —$OC_{1-4}$alkyl, —$OC_{1-4}$alkyl$CF_3$, —CN, —$CF_3$, —$OCF_2H$, —$NO_2$, —$NR_cR_d$, —$S(O)_{0-2}C_{1-4}$alkyl, —C(O)$C_{1-4}$alkyl, S(O)(O)$NH_2$, —$(CH_2)_{0-2}$-morpholinyl, piperidin-1-yl, piperazinyl, said piperazinyl being optionally substituted with a methyl, or two $R_b$ substituents on adjacent carbon atoms taken together form —$O(CH_2)_{1-2}O$—;

ii) pyridyl substituted with 0, 1 or 2 substituents $R_e$; where each $R_e$ is independently selected from halo, —$C_{1-4}$alkyl, —$OC_{1-4}$alkyl, —$CF_3$, —$NR_cR_d$ or 4-morpholinyl; or iii) a bicyclic 9-11-membered aromatic heterocycle optionally substituted with 1 substituent $R_f$;

where $R_f$ is —$C_{1-4}$alkyl;

$R_c$ and $R_d$ are each independently selected from H or —$C_{1-4}$ alkyl;

$R_1$ is H, $C_{1-4}$alkyl-O—$C_{1-4}$alkyl, or $C_{1-4}$alkyl optionally substituted with halo;

$R_2$ and $R_3$ and are each independently H, halo or —$C_{1-4}$ alkyl;

each $Y_1$, $Y_2$ and $Y_3$ is independently CH or N;

$R_6$ is i) H, —$C_{1-4}$alkyl, —$CF_3$, —$OR_z$ or —$NR_hR_i$;

where $R_h$ is selected from:

a) H, —$C_{0-4}$alkyl$CF_3$, —$C_{1-4}$alkyl-$N(CH_3)_2$, saturated $C_{3-7}$cycloalkyl or —$C_{1-4}$alkyl-monocyclic heteroaryl ring;

b) —$C_{1-5}$alkyl optionally substituted with OH;

c) —$C_{1-4}$alkyl-heterocycloalkyl, wherein said heterocycloalkyl is optionally substituted with —$C_{1-4}$alkyl; or d) —$C_{0-4}$alkyl-phenyl, said phenyl being optionally substituted with one or two $R_j$ moieties; where each $R_j$ is independently halo, —$OC_{1-4}$alkyl, Rz is —$C_{1-4}$alkyl, —$C_{1-4}$alkyl$CF_3$ or —$C_{1-4}$alkyl-heterocycloalkyl;

ii) 1-pyrrolidinyl optionally substituted with a moiety selected from the group consisting of —$NR_kR_i$ and —$C_{1-4}$alkyl, said —$C_{1-4}$alkyl optionally substituted with —OH;

iii) 1-piperidinyl optionally substituted with —$C_{1-4}$alkyl, —C(O)$NH_2$, —$CO_2C_{1-4}$alkyl or —$C_{0-4}$alkyl-phenyl;

103 iv) piperazinyl optionally substituted with —$C_{1-5}$alkyl, $OC_{1-4}$alkyl, —$C_{0-4}$alkylpyridyl, —$C_{0-4}$alkyl-1-methyl-piperidin-4-yl, —$C_{1-4}$alkyl$NR_kR_i$ or —$C_{0-4}$alkyl-phenyl, said phenyl being optionally substituted with one or two $R_T$ substituents; where each $R_T$ substituent is selected from the group consisting of halo, —$OCF_3$, —$C_{1-4}$alkyl, —$OC_{1-4}$alkyl, —$CO_2C_{1-4}$alkyl, —$C(O)C_{1-4}$alkyl and —$C_{0-4}$alkyl$NR_kR_i$ or two $R_T$ substituents on adjacent carbon atoms taken together form —$O(CH_2)_{1-2}O$—;
v) phenyl optionally substituted with halo, —$CF_3$, —$OCF_3$;
vi) pyridyl;
vii) morpholin-yl;
$R_k$ is H, —$C_{1-4}$alkyl or —$C(O)_{1-2}C_{1-4}$alkyl;
$R_i$ is H or $C_{1-4}$alkyl;
N-oxides, enantiomers, racemic mixtures and pharmaceutically acceptable salts thereof.

3. The compound according to claim 1 of formula (TB)

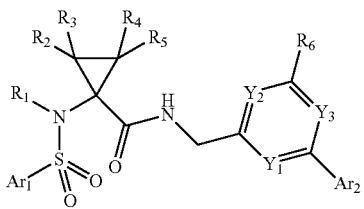

(IB)

wherein:
$Ar_1$ is:
i) phenyl substituted with 0, 1, 2 or 3 substituents $R_a$; or
ii) a 5- or 6-membered monocyclic aromatic heterocycle ring, optionally substituted with one or two substituents $R_a$; where each $R_a$ is independently halo, —$C_{1-4}$alkyl, —$OC_{1-4}$alkyl, —CN, —$CF_3$, —$OCF_3$, —$NO_2$, —$C(O)C_{1-4}$alkyl or —$CO_2H$;
$Ar_2$ is:
i) phenyl substituted with 0, 1, 2 or 3 substituents $R_b$; where each $R_b$ is independently halo, —$C_{1-4}$alkyl, —$C(O)NR_cR_d$, —$OC_{1-4}$alkyl, —$OC_{1-4}$alkyl$CF_3$, —CN, —$CF_3$, —$OCF_2H$, —$NO_2$, —$NR_cR_d$, —$S(O)_{0-2}C_{1-4}$alkyl, —$C(O)C_{1-4}$alkyl, $S(O)(O)NH_2$, —$(CH_2)_{0-2}$-morpholinyl, piperidin-1yl, piperazinyl, said piperazinyl being optionally substituted with a methyl, or two $R_b$ substituents on adjacent carbon atoms taken together form —$O(CH_2)_{1-2}O$—;
ii) pyridyl substituted with 0, 1 or 2 substituents $R_e$; where each $R_e$ is independently selected from halo, —$C_{1-4}$alkyl, —$OC_{1-4}$alkyl, —$CF_3$, —$NR_cR_d$ or 4-morpholinyl; or
iii) a bicyclic 9-11-membered aromatic heterocycle optionally substituted with 1 substituent $R_f$;
where $R_f$ is —$C_{1-4}$alkyl;
$R_c$ and $R_d$ are each independently selected from H or —$C_{1-4}$alkyl;
$R_1$ is H, $C_{1-4}$alkyl-O—$C_{1-4}$alkyl, or $C_{1-4}$alkyl optionally substituted with halo;
$R_2$, $R_3$, $R_4$, and $R_5$ are each independently H, halo or —$C_{1-4}$alkyl;
each $Y_1$, $Y_2$ and $Y_3$ is independently CH or N;
$R_6$ is
i) H, —$C_{1-4}$alkyl, —$CF_3$, —$OR_z$ or —$NR_hR_i$;
where $R_h$ is selected from
a) H, —$C_{0-4}$alkyl$CF_3$, —$C_{1-4}$alkyl-$N(CH_3)_2$, saturated $C_{3-7}$cycloalkyl or —$C_{1-4}$alkyl-monocyclic heteroaryl ring;

104 b) —$C_{1-5}$alkyl optionally substituted with OH;
c) —$C_{1-4}$alkyl-heterocycloalkyl, wherein said heterocycloalkyl is optionally substituted with —$C_{1-4}$alkyl; or
d) —$C_{0-4}$alkyl-phenyl, said phenyl being optionally substituted with one or two $R_j$ moieties; where each $R_j$ is independently halo, —$OC_{1-4}$alkyl,
Rz is —$C_{1-4}$alkyl, —$C_{1-4}$alkyl$CF_3$ or —$C_{1-4}$alkyl-heterocycloalkyl;
ii) 1-pyrrolidinyl optionally substituted with a moiety selected from the group consisting of —$NR_kR_i$ and —$C_{1-4}$alkyl, said —$C_{1-4}$alkyl optionally substituted with —OH;
iii) 1-piperidinyl optionally substituted with —$C_{1-4}$alkyl, —$C(O)NH_2$, —$CO_2C_{1-4}$alkyl or —$C_{0-4}$alkyl-phenyl;
iv) piperazinyl optionally substituted with —$Ci_{1-5}$alkyl, —$OC_{1-4}$alkyl, —$C_{0-4}$alkylpyridyl, —$C_{0-4}$alkyl-1-methyl-piperidin-4-yl, —$C_{0-4}$alkyl$NR_kR_i$ or —$C_{0-4}$alkyl-phenyl, said phenyl being optionally substituted with one or two $R_T$ substituents; where each $R_T$ substituent is selected from the group consisting of halo, —$OCF_3$, —$C_{1-4}$alkyl, —$OC_{1-4}$alkyl, —$CO_2C_{1-4}$alkyl, —$C(O)C_{1-4}$alkyl and —$C_{0-4}$alkyl$NR_kR_i$, or two $R_T$ substituents on adjacent carbon atoms taken together form —$O(CH_2)_{1-2}O$—;
v) phenyl optionally substituted with halo, $CF_3$;
vi) pyridyl;
vii) morpholin-yl;
$R_k$ is H, —$C_{1-4}$alkyl or —$C(O)_{1-2}C_{1-4}$alkyl;
$R_i$ is H or $C_{1-4}$alkyl;
N-oxides, enantiomers, racemic mixtures and pharmaceutically acceptable salts thereof.

4. The compound according to claim 1 wherein each $Y_1$, $Y_2$ are CH and $Y_3$ is N.

5. The compound according to claim 1 wherein each $Y_1$, $Y_2$ and $Y_3$ are CH.

6. The compound according to claim 4 wherein:
$Ar_1$ is:
i) phenyl substituted with one substituent $R_a$; where $R_a$ is halo, or —$C_{1-4}$alkyl; ii) a thienyl ring optionally substituted with one substituents $R_a$: where $R_a$ is halo;
$Ar_2$ is:
i) phenyl substituted with 1 substituent $R_b$; where $R_b$ is —$OC_{0-4}$alkyl$CF_3$;
$R_1$ is H or $C_{1-4}$ alkyl optionally substituted with halo;
$R_2$, $R_3$, $R_4$, and $R_5$ are each independently H, or —$C_{1-4}$ alkyl;
$R_6$ is:
i) H;
ii) 1-pyrrolidinyl;
iii) phenyl optionally substituted with —$CF_3$ or —$OCF_3$;
iv) morpholin-yl.

7. The compound according to claim 1, selected from:
2-[ethyl-(4-fluorophenyl)sulfonyl-amino]-N-[[2-[4-(trifluoromethyl)phenyl]-4-pyridyl]methyl]prop-2-enamide;
2-[(4-fluorophenyl)sulfonyl-methyl-amino]-N-[[2-[4-(trifluoromethoxy)phenyl]-4-pyridyl]methyl]prop-2-enamide;
2-[(4-fluorophenyl)sulfonyl-ethyl-amino]-N-[[2-[4-(trifluoromethoxy)phenyl]-4-pyridyl]methyl]prop-2-enamide;
2-[(4-chlorophenyl)sulfonyl-methyl-amino]-N-[[2-[4-(trifluoromethoxy)phenyl]-4-pyridyl]methyl]prop-2-enamide;
2-[(4-chlorophenyl)sulfonyl-ethyl-amino]-N-[[2-[4-(trifluoromethoxy)phenyl]-4-pyridyl]methyl]prop-2-enamide;

2-(methyl(p-tolylsulfonyl)amino)-N-[[2-[4-(trifluoromethoxy)phenyl]-4-pyridyl]methyl]prop-2-enamide;

2-[(5-chloro-2-thienyl)sulfonyl-ethyl-amino]-N-[[2-[4-(trifluoromethoxy)phenyl]-4-pyridyl]methyl]prop-2-enamide;

2-[ethyl-(4-fluorophenyl)sulfonyl-amino]-N-[[3-[4-(trifluoromethyl)phenyl]phenyl]methyl]prop-2-enamide;

2-[(4-chlorophenyl)sulfonyl-methyl-amino]-N-[[3-[4-(trifluoromethyl)phenyl]phenyl]methyl]prop-2-enamide;

2-[(4-chlorophenyl)sulfonyl-ethyl-amino]-N-[[3-[4-(trifluoromethyl)phenyl]phenyl]methyl]prop-2-enamide;

2-[ethyl-(4-fluorophenyl)sulfonyl-amino]-N-[[-[4-(trifluoromethoxy)phenyl]phenyl]methyl]prop-2-enamide;

2-[(5-chloro-2-thienyl)sulfonyl-ethyl-amino]-N-[[2-[4-(trifluoromethyl)phenyl]-4-pyridyl]methyl]prop-2-enamide;

2-[(4-chlorophenyl)sulfonyl-methyl-amino]-N-[[2-pyrrolidin-1-yl-6-[4-trifluoromethyl)phenyl]-4-pyridyl]methyl]prop-2-enamide;

2-[(4-chlorophenyl)sulfonyl-ethyl-amino]-N-[[2-pyrrolidin-1-yl-6-[4-(trifluoromethyl)phenyl]-4-pyridyl]methyl]prop-2-enamide;

2-[(5-chloro-2-thienyl)sulfonyl-ethyl-amino]-N-[[2-pyrrolidin-1-yl-6-[4-trifluoromethyl)phenyl]-4-pyridyl]methyl]prop-2-enamide;

2-[(4-chlorophenyl)sulfonyl-methyl-amino]-N-[2-morpholino-6-[4-(trifluoromethoxy)phenyl]-4-pyridyl]methyl]prop-2-enamide;

2-[(4-chlorophenyl)sulfonyl-ethyl-amino]-N-[[2-morpholino-6-[4-(trifluoromethoxy)phenyl]-4-pyridyl]methyl]prop-2-enamide;

2-[ethyl-(4-fluorophenyl)sulfonyl-amino]-N-[[2-pyrrolidin-1-yl-6-[4-(trifluoromethoxy)phenyl]-4-pyridyl]methyl]prop-2-enamide;

N-[[2,6-bis[4-(trifluoromethyl)phenyl]-4-pyridyl]methyl]-2-[(4-chlorophenyl)sulfonyl-ethyl-amino]prop-2-enamide;

N-[[2,6-bis[4-(trifluoromethoxy)phenyl]-4-pyridyl]methyl]-2-[(4-chlorophenyl)sulfonyl-methyl-amino]prop-2-enamide;

(Z)-2-[(4-fluorophenyl)sulfonyl-methyl-amino]-N-[[2-[4-(trifluoromethoxy)phenyl]-4-pyridyl]methyl]but-2-enamide;

(Z)-2-[ethyl-(4-fluorophenyl)sulfonyl-amino]-N-[[2-[4-(trifluoromethoxy)phenyl]-4-pyridyl]methyl]but-2-enamide;

(Z)-2-[(4-chlorophenyl)sulfonyl-methyl-amino]-N-[[3-[4-(trifluoromethyl)phenyl]phenyl]methyl]but-2-enamide;

(Z)-2-[(4-chlorophenyl)sulfonyl-ethyl-amino]-N-[[3-[4-(trifluoromethyl)phenyl]phenyl]methyl]but-2-enamide;

1-[ethyl-(4-fluorophenyl)sulfonyl-amino]-N-[[2-[4-(trifluoromethyl)phenyl]-4-pyridyl]methyl]cyclopropanecarboxamide;

1-[ethyl-(4-fluorophenyl)sulfonyl-amino]-N-[[2-[4-(trifluoromethoxy)phenyl]-4-pyridyl]methyl]cyclopropanecarboxamide;

1-[(4-chlorophenyl)sulfonyl-ethyl-amino]-N-[[2-[4-(trifluoromethoxy)phenyl]-4-pyridyl]methyl]cyclopropanecarboxamide;

1-[(5-chloro-2-thienyl)sulfonyl-ethyl-amino]-N-[[2-[4-(trifluoromethoxy)phenyl]-4-pyridyl]methyl]cyclopropanecarboxamide;

1-[ethyl-(4-fluorophenyl)sulfonyl-amino]-N-[[3-[4-(trifluoromethyl)phenyl]phenyl]methyl]cyclopropanecarboxamide;

1-[(4-chlorophenyl)sulfonyl-ethyl-amino]-N-[[3-[4-(trifluoromethyl)phenyl]phenyl]methyl]cyclopropanecarboxamide;

1-[ethyl-(4-fluorophenyl)sulfonyl-amino]-N-[[3-[4-(trifluoromethoxy)phenyl]phenyl]methyl]cyclopropanecarboxamide;

1-[(4-fluorophenyl)sulfonylamino]-N-[[2-pyrrolidin-1-yl-6-[4-(trifluoromethyl)phenyl]-4-pyridyl]methyl]cyclopropanecarboxamide;

1-[(4-fluorophenyl)sulfonylamino]-N-[[2-pyrrolidin-1-yl-6-[4-(trifluoromethoxy)phenyl]-4-pyridyl]methyl]cyclopropanecarboxamide;

1-[(5-chloro-2-thienyl)sulfonyl-ethyl-amino]-N-[[2-pyrrolidin-1-yl-6-[4-(trifluoromethyl)phenyl]-4-pyridyl]methyl]cyclopropanecarboxamide;

2-[(3,4-difluorophenyl)sulfonyl-ethyl-amino]-N-[[2-[4-(trifluoromethyl)phenyl]-4-pyridyl]methyl]prop-2-enamide;

2-[(3-difluorophenyl)sulfonyl-ethyl-amino]-N-[[2-[4-(trifluoromethyl)phenyl]-4-pyridyl]methyl]prop-2-enamide;

N-[[2-dimethylamino-6-[4-(trifluoromethyl)phenyl]-4-pyridyl]methyl]-2-[ethyl-(4-fluorophenyl)sulfonyl-amino]prop-2-enamide;

2-[ethyl-(4-fluorophenyl)sulfonyl-amino]-N-[[2-pyrrolidin-1-yl-6-[4-(trifluoromethyl)phenyl]-4-pyridyl]methyl]prop-2-enamide;

2-[(5-chloro-2-thienyl)sulfonyl-ethyl-amino]-N-[[2-dimethylamino-6-[4-(trifluoromethyl)phenyl]-4-pyridyl]methyl]prop-2-enamide;

2-[ethyl-(4-fluorophenyl)sulfonyl-amino]-N-[[2-methoxy-6-[4-(trifluoromethyl)phenyl]-4-pyridyl]methyl]prop-2-enamide;

N-[[2-dimethylamino-6-[4-(trifluoromethyl)phenyl]-4-pyridyl]methyl]-2-(ethyl(2-thienylsulfonyl)amino)prop-2-enamide;

2-[ethyl-(4-fluorophenyl)sulfonyl-amino]-N-[[2-morpholino-6-[4-(trifluoromethyl)phenyl]-4-pyridyl]methyl]prop-2-enamide;

2-[(5-chloro-2-thienyl)sulfonyl-ethyl-amino]-N-[[2-morpholino-6-[4-(trifluoromethyl)phenyl]-4-pyridyl]methyl]prop-2-enamide;

2-[ethyl-(4-fluorophenyl)sulfonyl-amino]-N-[[2-isopropoxy-6-[4-(trifluoromethyl)phenyl]-4-pyridyl]methyl]prop-2-enamide;

N-[[2-dimethylamino-6-[4-(trifluoromethyl)phenyl]-4-pyridyl]methyl]-1-[ethyl-(4-fluorophenyl)sulfonyl-amino]cyclopropanecarboxamide;

1-[(5-chloro-2-thienyl)sulfonyl-ethyl-amino]-N-[[2-[4-(trifluoromethyl)phenyl]-4-pyridyl]methyl]cyclopropanecarboxamide;

1-[(5-chloro-2-thienyl)sulfonyl-ethyl-amino]-N-[[3-[4-(trifluoromethoxy)phenyl]phenyl]methyl]cyclopropanecarboxamide;

1-[ethyl-(4-fluorophenyl)sulfonyl-amino]-N-[[2-methoxy-6-[4-(trifluoromethyl)phenyl]-4-pyridyl]methyl]cyclopropanecarboxamide;

1-[ethyl-(4-fluorophenyl)sulfonyl-amino]-N-[[2-isopropoxy-6-[4-(trifluoromethyl)phenyl]-4-pyridyl]methyl]cyclopropanecarboxamide;

1-[(5-chloro-2-thienyl)sulfonyl-ethyl-amino]-N-[[2-methoxy-6-[4-(trifluoromethyl)phenyl]-4-pyridyl]methyl]cyclopropanecarboxamide;

1-[ethyl-(4-fluorophenyl)sulfonyl-amino]-N-[[2-pyrrolidin-1-yl-6-[4-(trifluoromethyl)phenyl]-4-pyridyl]methyl]cyclopropanecarboxamide;

N-[[2-ethoxy-6-[4-(trifluoromethyl)phenyl]-4-pyridyl]methyl]-1-[ethyl-(4-fluorophenyl)sulfonyl-amino]cyclopropanecarboxamide;

1-[(5-chloro-2-thienyl)sulfonyl-ethyl-amino]-N-[[2-ethoxy-6-[4-(trifluoromethyl)phenyl]-4-pyridyl]methyl]cyclopropanecarboxamide;

2-[ethyl-(4-fluorophenyl)sulfonyl-amino]-N-[[1-oxido-2-[4-(trifluoromethyl)phenyl]pyridin-1-ium-4-yl]methyl]prop-2-enamide;

2-[(5-chloro-2-thienyl)sulfonyl-ethyl-amino]-N-[[3-[4-(trifluoromethoxy)phenyl]phenyl]methyl]prop-2-enamide;

2-[(4-fluorophenyl)sulfonyl-methyl-amino]-N-[[2-[4-(trifluoromethyl)phenyl]-4-pyridyl]methyl]prop-2-enamide;

1-[(4-fluorophenyl)sulfonyl-methyl-amino]-N-[[3-[4-(trifluoromethoxy)phenyl]phenyl]methyl]cyclopropanecarboxamide;

1-[(4-fluorophenyl)sulfonyl-methyl-amino]-N-[[3-[4-(trifluoromethyl)phenyl]phenyl]methyl]cyclopropanecarboxamide;

1-[(5-chloro-2-thienyl)sulfonyl-ethyl-amino]-N-[[3-[4-(trifluoromethyl)phenyl]phenyl]methyl]cyclopropanecarboxamide;

1-[ethyl-(4-fluorophenyl)sulfonyl-amino]-N-[[4-[4-(trifluoromethyl)phenyl]-2-pyridyl]methyl]cyclopropanecarboxamide;

1-[ethyl-(4-fluorophenyl)sulfonyl-amino]-N-[[2-pyrrolidin-1-yl-6-[4-(trifluoromethoxy)phenyl]-4-pyridyl]methyl]cyclopropanecarboxamide;

1-[ethyl-(4-fluorophenyl)sulfonyl-amino]-N-[[2-morpholino-6-[4-(trifluoromethyl)phenyl]-4-pyridyl]methyl]cyclopropanecarboxamide;

N-[[2-[4-(cyclopropylmethyl)piperazin-1-yl]-6-[4-(trifluoromethoxy)phenyl]-4-pyridyl]methyl]-2-[ethyl-(4-fluorophenyl)sulfonyl-amino]prop-2-enamide;

N-[[2-[4-(cyclopropylmethyl)piperazin-1-yl]-6-[4-(trifluoromethyl)phenyl]-4-pyridyl]methyl]-1-[ethyl-(4-fluorophenyl)sulfonyl-amino]cyclopropanecarboxamide; 1-[(5-chloro-2-thienyl)sulfonyl-ethyl-amino]-N-[[2-[4-(cyclopropylmethyl)piperazin-1-yl]-6-[4-(trifluoromethyl)phenyl]-4-pyridyl]methyl]cyclopropanecarboxamide;

N-[[2-(4-cyclohexylpiperazin-1-yl)-6-[4-(trifluoromethyl)phenyl]-4-pyridyl]methyl]-1-[ethyl-(4-fluorophenyl)sulfonyl-amino]cyclopropanecarboxamide;

1-[(5-chloro-2-thienyl)sulfonyl-ethyl-amino]-N-[[2-(4-cyclohexylpiperazin-1-yl)-6-[4-(trifluoromethyl)phenyl]-4-pyridyl]methyl]cyclopropanecarboxamide.

8. A pharmaceutical composition comprising one or more compounds of claim 1 as the active ingredient and a pharmaceutically acceptable carrier.

9. A method of inhibiting TRPA1 receptors in a cell wherein the method comprises administering at least one of the compounds of claim 1 or a pharmaceutically acceptable salt thereof to the cell.

10. A method of treating pain, asthma, chronic cough or COPD in a human suffering therefrom, wherein the method comprises administering at least one of the compounds of claim 1 or a pharmaceutically acceptable salt thereof to the human.

11. The compound according to claim 2 wherein each $Y_1$, $Y_2$ are CH and $Y_3$ is N.

12. The compound according to claim 3 wherein each $Y_1$, $Y_2$ are CH and $Y_3$ is N.

13. The compound according to claim 2 wherein each $Y_1$, $Y_2$ and $Y_3$ are CH.

14. The compound according to claim 3 wherein each $Y_1$, $Y_2$ and $Y_3$ are CH.

15. The compound according to claim 5 wherein:

$Ar_1$ is:
i) phenyl substituted with one substituent $R_a$; where $R_a$ is halo, or —$C_{1-4}$alkyl; ii) a thienyl ring optionally substituted with one substituents $R_a$: where $R_a$ is halo;

$Ar_2$ is:
i) phenyl substituted with 1 substituent $R_b$; where $R_b$ is —$OC_{0-4}$alkyl$CF_3$;

$R_1$ is H or $C_{1-4}$ alkyl optionally substituted with halo;

$R_2$, $R_3$, $R_4$, and $R_5$ are each independently H, or —$C_{1-4}$alkyl;

$R_6$ is:
i) H;
ii) 1-pyrrolidinyl;
iii) phenyl optionally substituted with —$CF_3$ or —$OCF_3$;
iv) morpholin-yl.

* * * * *